United States Patent
Moulton et al.

(10) Patent No.: US 11,236,329 B2
(45) Date of Patent: *Feb. 1, 2022

(54) COMPOUND AND METHOD FOR TREATING MYOTONIC DYSTROPHY

(71) Applicant: Sarepta Therapeutics, Inc., Corvallis, OR (US)

(72) Inventors: Hong M. Moulton, Corvallis, OR (US); Ryszard Kole, Corvallis, OR (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/261,120

(22) Filed: Apr. 24, 2014

(65) Prior Publication Data

US 2015/0080311 A1 Mar. 19, 2015

Related U.S. Application Data

(63) Continuation of application No. 13/219,401, filed on Aug. 26, 2011, now Pat. No. 8,741,863, which is a
(Continued)

(51) Int. Cl.
*C12N 15/113* (2010.01)
*A61K 47/64* (2017.01)
(Continued)

(52) U.S. Cl.
CPC ........ *C12N 15/113* (2013.01); *A61K 31/7088* (2013.01); *A61K 47/64* (2017.08);
(Continued)

(58) Field of Classification Search
CPC .. C12N 15/87; C12N 15/113; C12N 2310/11; C12N 2810/40; A61K 31/7088; A61K 47/48246; A61K 47/64; C07K 2319/33
See application file for complete search history.

(56) References Cited

U.S. PATENT DOCUMENTS

| 5,087,617 A | 2/1992 | Smith |
| 5,525,465 A | 6/1996 | Haralambidis et al. |

(Continued)

FOREIGN PATENT DOCUMENTS

| CA | 2834128 A1 | 11/2012 |
| EP | 1 938 802 A1 | 7/2008 |

(Continued)

OTHER PUBLICATIONS

Ge et al., Antimicrobial Agents and Chemotherapy, vol. 50(11):3724-3733 (Sep. 11, 2006).*

(Continued)

*Primary Examiner* — Randall L Beane
(74) *Attorney, Agent, or Firm* — Lathrop GPM LLP; Brian C. Trinque; Alan W. Steele

(57) ABSTRACT

An antisense compound for use in treating myotonic dystrophy DM1 or DM2, a method of enhancing antisense targeting to heart and quadricep muscles, and a method for treating DM1 or DM2 in a mammalian subject are disclosed. The oligonucleotide has 8-30 bases, with at least 8 contiguous bases being complementary to the polyCUG or polyCCUG repeats in the 3'UTR region of dystrophia myotonica protein kinase (DMPK) mRNA in DM1 or DM2, respectively. Conjugated to the oligonucleotide is a cell-penetrating peptide having the sequence $(RXRR(B/X)R)_2XB$, where R is arginine; B is β-alanine; and each X is $—C(O)—(CH_2)_n—NH—$, where n is 4-6. The antisense compound is effective to selectively block the sequestration of muscleblind-like 1 protein (MBNL1) and/or CUGBP, in heart and quadricep muscle in a myotonic dystrophy animal model.

11 Claims, 35 Drawing Sheets

Specification includes a Sequence Listing.

Related U.S. Application Data continuation of application No. 12/493,140, filed on Jun. 26, 2009, now abandoned, which is a continuation-in-part of application No. 12/217,040, filed on Jun. 30, 2008, now abandoned.

(60) Provisional application No. 60/937,725, filed on Jun. 29, 2007.

(51) Int. Cl.
  *A61K 31/7088* (2006.01)
  *C12N 15/87* (2006.01)

(52) U.S. Cl.
  CPC .......... *C12N 15/87* (2013.01); *C07K 2319/33* (2013.01); *C12N 2310/11* (2013.01); *C12N 2810/40* (2013.01)

(56) References Cited

U.S. PATENT DOCUMENTS

| | | | |
|---|---|---|---|
| 5,686,564 A | 11/1997 | Brandish et al. | |
| 5,747,641 A | 5/1998 | Frankel et al. | |
| 5,849,727 A | 12/1998 | Porter et al. | |
| 6,159,946 A | 12/2000 | Zalewski et al. | |
| 6,303,573 B1 | 10/2001 | Rouslahti et al. | |
| 6,306,993 B1 | 10/2001 | Rothbard et al. | |
| 6,329,501 B1 | 12/2001 | Smith et al. | |
| 6,365,351 B1 | 4/2002 | Iversen | |
| 6,495,663 B1 | 12/2002 | Rothbard et al. | |
| 6,559,279 B1 | 5/2003 | Manoharan et al. | |
| 6,593,292 B1 | 7/2003 | Rothbard et al. | |
| 6,645,974 B2 | 11/2003 | Hutchinson et al. | |
| 6,669,951 B2* | 12/2003 | Rothbard | A61K 31/155 424/436 |
| 7,138,238 B2 | 11/2006 | Vodyanoy et al. | |
| 7,169,814 B2 | 1/2007 | Rothbard et al. | |
| 7,456,146 B2 | 11/2008 | Yu et al. | |
| 7,468,418 B2 | 12/2008 | Iversen et al. | |
| 7,482,016 B2 | 1/2009 | Doerr et al. | |
| 7,507,196 B2 | 3/2009 | Stein et al. | |
| 7,524,829 B2 | 4/2009 | Stein et al. | |
| 7,582,615 B2 | 9/2009 | Neuman et al. | |
| 7,585,834 B2 | 9/2009 | Wender et al. | |
| 7,786,151 B2 | 8/2010 | Hagiwara et al. | |
| 7,790,694 B2 | 9/2010 | Geller et al. | |
| 7,855,283 B2 | 12/2010 | Iversen | |
| 7,888,012 B2* | 2/2011 | Iversen | C12N 15/1136 435/6.16 |
| 7,943,762 B2 | 5/2011 | Weller et al. | |
| 7,973,015 B2 | 7/2011 | van Ommen et al. | |
| 7,989,608 B2 | 8/2011 | Mourich et al. | |
| 8,008,469 B2 | 8/2011 | Mourich et al. | |
| 8,030,291 B2 | 10/2011 | Stein et al. | |
| 8,030,292 B2 | 10/2011 | Stein et al. | |
| 8,053,420 B2 | 11/2011 | Iversen et al. | |
| 8,067,571 B2 | 11/2011 | Weller et al. | |
| 8,084,433 B2 | 12/2011 | Iversen et al. | |
| 8,129,352 B2 | 3/2012 | Iversen et al. | |
| 8,168,604 B2 | 5/2012 | Stein et al. | |
| 8,741,863 B2* | 6/2014 | Moulton | C12N 15/87 514/44 A |
| 8,785,410 B2* | 7/2014 | Iversen | C12N 15/1136 514/44 A |
| 8,835,402 B2 | 9/2014 | Kole et al. | |
| 8,865,883 B2* | 10/2014 | Sazani | C12N 15/111 435/325 |
| 8,871,918 B2* | 10/2014 | Sazani | C12N 15/111 536/23.1 |
| 9,068,185 B2* | 6/2015 | Iversen | C12N 15/1138 |
| 9,161,948 B2 | 10/2015 | Hanson et al. | |
| 10,006,031 B2* | 6/2018 | Iversen | C07H 21/00 |
| 10,626,396 B2* | 4/2020 | Iversen | A61K 47/645 |
| 2001/0021700 A1 | 9/2001 | Moore et al. | |
| 2002/0045736 A1 | 4/2002 | Yu et al. | |
| 2002/0127198 A1 | 9/2002 | Rothbard et al. | |
| 2003/0022831 A1 | 1/2003 | Rothbard et al. | |
| 2003/0031655 A1 | 2/2003 | Woolf | |
| 2003/0045488 A1 | 3/2003 | Brown et al. | |
| 2003/0087861 A1 | 5/2003 | Iversen | |
| 2003/0185788 A1 | 10/2003 | Rothbard et al. | |
| 2003/0228348 A1 | 12/2003 | Hirayama et al. | |
| 2004/0170955 A1 | 9/2004 | Arap et al. | |
| 2004/0247614 A1 | 12/2004 | Dorr et al. | |
| 2004/0265879 A1* | 12/2004 | Iversen | A61K 47/48246 435/6.16 |
| 2005/0171026 A1 | 8/2005 | Hagiwara et al. | |
| 2006/0014712 A1 | 1/2006 | Neuman | |
| 2006/0063150 A1* | 3/2006 | Iversen | C12N 15/111 435/5 |
| 2006/0078542 A1 | 4/2006 | Mah et al. | |
| 2006/0127981 A1 | 6/2006 | Bergman et al. | |
| 2006/0148747 A1 | 7/2006 | Stein et al. | |
| 2006/0276425 A1 | 12/2006 | Mourich et al. | |
| 2007/0004661 A1 | 1/2007 | Stein et al. | |
| 2007/0066556 A1 | 3/2007 | Stein et al. | |
| 2007/0122821 A1* | 5/2007 | Iversen | C07H 21/00 435/6.16 |
| 2007/0129323 A1 | 6/2007 | Stein et al. | |
| 2007/0265214 A1 | 11/2007 | Stein et al. | |
| 2008/0194463 A1* | 8/2008 | Weller | A61K 48/00 514/1.1 |
| 2008/0267978 A1 | 10/2008 | Zutter | |
| 2009/0075377 A1 | 3/2009 | Lu et al. | |
| 2009/0082547 A1 | 3/2009 | Iversen et al. | |
| 2009/0088562 A1 | 4/2009 | Weller et al. | |
| 2009/0099066 A1 | 4/2009 | Moulton et al. | |
| 2009/0110689 A1 | 4/2009 | Mourich et al. | |
| 2009/0180958 A1 | 7/2009 | Koivistoinen et al. | |
| 2009/0318676 A1 | 12/2009 | Manoharan et al. | |
| 2010/0016215 A1 | 1/2010 | Moulton et al. | |
| 2010/0021456 A1 | 1/2010 | Miossec et al. | |
| 2010/0063133 A1 | 3/2010 | Neuman et al. | |
| 2010/0130591 A1 | 5/2010 | Sazani et al. | |
| 2010/0184670 A1 | 7/2010 | Mourich et al. | |
| 2010/0184833 A1 | 7/2010 | De Kimpe et al. | |
| 2010/0190689 A1 | 7/2010 | Thornton et al. | |
| 2010/0234280 A1 | 9/2010 | Geller et al. | |
| 2010/0234281 A1 | 9/2010 | Weller et al. | |
| 2011/0118334 A1 | 5/2011 | Iversen | |
| 2011/0269665 A1 | 11/2011 | Kole | |
| 2011/0289608 A1 | 11/2011 | Schnell et al. | |
| 2011/0306550 A1 | 12/2011 | Vitek et al. | |
| 2012/0058946 A1 | 3/2012 | Moulton et al. | |
| 2012/0141463 A1 | 6/2012 | Wu et al. | |
| 2012/0148622 A1 | 6/2012 | tenOever | |
| 2012/0289457 A1 | 11/2012 | Hanson | |
| 2013/0005792 A1 | 1/2013 | Haining et al. | |
| 2013/0045202 A1 | 2/2013 | Irving et al. | |
| 2013/0089517 A1 | 4/2013 | Brady et al. | |
| 2013/0131312 A1 | 5/2013 | Iversen et al. | |
| 2015/0141321 A1 | 5/2015 | Kole et al. | |
| 2015/0152415 A1* | 6/2015 | Sazani | C12N 15/111 514/44 A |

FOREIGN PATENT DOCUMENTS

| | | |
|---|---|---|
| JP | 2002-511885 A | 4/2002 |
| JP | 2003-504417 A | 2/2003 |
| JP | 2007-536253 A | 12/2007 |
| JP | 2011-505846 A | 3/2011 |
| WO | 94/04686 A1 | 3/1994 |
| WO | 99/05302 A1 | 2/1999 |
| WO | 00/44897 A1 | 8/2000 |
| WO | 00/71706 A1 | 11/2000 |
| WO | 01/62297 A1 | 8/2001 |
| WO | 02/38764 A2 | 5/2002 |
| WO | 03/068942 A2 | 8/2003 |
| WO | 2004/097017 A2 | 11/2004 |
| WO | 2005/010044 A2 | 2/2005 |
| WO | 2005/030799 A1 | 4/2005 |
| WO | 2005/072527 A2 | 8/2005 |
| WO | 2005/089247 A2 | 9/2005 |

(56) References Cited

FOREIGN PATENT DOCUMENTS

| | | |
|---|---|---|
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/083183 A1 | 8/2006 |
| WO | 2006/086667 A2 | 8/2006 |
| WO | 2006/088833 A2 | 8/2006 |
| WO | 2007/009094 A2 | 1/2007 |
| WO | 2007/030576 A2 | 3/2007 |
| WO | 2007/030691 A2 | 3/2007 |
| WO | 2007/056466 A2 | 5/2007 |
| WO | 2007/103529 A2 | 9/2007 |
| WO | 2008/005002 A1 | 1/2008 |
| WO | 2008/008113 A1 | 1/2008 |
| WO | 2008/025025 A2 | 2/2008 |
| WO | 2008/036127 A2 | 3/2008 |
| WO | 2009/005793 A2 | 1/2009 |
| WO | 2009/026412 A1 | 2/2009 |
| WO | 2009/079790 A1 | 7/2009 |
| WO | 2009/086469 A2 | 7/2009 |
| WO | 2009/144481 A2 | 12/2009 |
| WO | 2010/048586 A1 | 4/2010 |
| WO | 2010/054267 A1 | 5/2010 |
| WO | 2010/072405 A1 | 7/2010 |
| WO | 2010/080554 A1 | 7/2010 |
| WO | 2011/143608 A1 | 11/2011 |

OTHER PUBLICATIONS

Image Integrity, Nature.com, 6 pages, Apr. 28, 2017) (Year: 2017).*
Dagher et al., Rhabdomyosarcoma: an overview, Oncologist, vol. 4(1):34-44 (1999) (Year: 1999).*
Hilton-Jones, D., Diagnosis and Treatment of Inflammatory Muscle Diseases, Journal of Neurology, Neurosurgery & Psychiatry, vol. 74:ii25-ii31 (Jun. 1, 2003) (Year: 2003).*
Davies MJ, The cardiomyopathies: an overview, Heart vol. 83:469-474(Apr. 1, 2000) (Year: 2000).*
Cadavid et al., Infection and Inflammation in Skeletal Muscle from Nonhuman Primates Infected with Different Genospecies of the Lyme Disease Spirochete Borrelia burgdorferi, Infection and Immunity, vol. 71(12)7087-7098 (Nov. 2003) (Year: 2003).*
Giorgio et al., Lung cancer and skeletal muscle metastases, Ann Thorac Surg. vol. 78(2):709-11 (Aug. 2004) (Year: 2004).*
Taketani et al., Change of c-Myc Expression and Cardiac Hypertrophy in Patients With Aortic Valve Replacement, Ann Thorac Surg, vol. 71:1154-9 (2001) (Year: 2001).*
Kaihatsu et al., Recognition of Chromosomal DNA by PNAs, Chemistry & Biology, vol. 11:749-758 (Jun. 2004) (Year: 2004).*
Corey et al., Recognition of Chromosomal DNA in Human Cells by Peptide Nucleic Acids and Small Duplex RNAs, Ann. N.Y. Acad. Sci. 1058:16-25 (2005) (Year: 2005).*
Wilton et al., "Antisense Oligonucleotide-induced Exon Skipping Across the Human Dystrophin Gene Transcript," *Molecular Therapy* 15(7): 1288-1296, Jul. 2007.
EMBL/GenBank/DDBJ database (DESHAZER), Sequence CH899747.1, retrieved from the Internet, URL=http://www.ebi.ac.uk/sgibin/emblfetch?style+html&id+CH899747, download date May 26, 2007, 196 pages.
International Preliminary Examination Report for PCT/US2004/013660, dated Nov. 4, 2005, 8 pgs.
International Search Report, dated Feb. 21, 2005, for PCT/US2004/013660, 7 pages.
International Search Report and Written Opinion for International Application No. PCT/US2005/018213, dated Sep. 26, 2007, 8 pgs.
International Preliminary Report on Patentability for International Application No. PCT/US2005/018213, dated Oct. 23, 2007, 7 pages.
International Preliminary Report on Patentability for corresponding International Application No. PCT/US2008/008168, dated Oct. 12, 2009, 10 pgs.
International Search report and Written Opinion, dated Mar. 19, 2009, for PCT/US08/08168, 13 pages.
PubChem (online), 6-Aminocaproic Acid—Compound Summary (CID 5460263), retrieved from URL=http://pubchem.ncbi.nlm.nih.gov/summary/summary.cgi?cid=5460263&loc=ec_res, download date Jun. 3, 2010, 3 pages.
Abes et al., "Arginine-rich cell penetrating peptides: Design, structure-activity, and applications to alter pre-mRNA splicing by steric-block oligonucleotides," *Journal of Peptide Science* 74:455-460, 2008.
Abes et al., "Vectorization of morpholino oligomers by the (R-Ahx-R)$_4$ peptide allows efficient splicing correction in the absence of endosomolytic agents," *Journal of Controlled Release* 116:304-313, 2006.
Abes et al., "Delivery of steric block morpholino oligomers by (R-X-R)$_4$ peptides: structure-activity studies," *Nucleic Acids Research* 36(20): 6343-6354, 2008.
Alter et al., "Systemic delivery of morpholino oligonucleotide restores dystrophin expression bodywide and improves dystrophic pathology," *Nature Medicine* 12(2):175-177, Feb. 2006.
Arora et al., "Bioavailability and Efficacy of Antisense Morpholino Oligomers Targeted to c-myc and Cytochrome P-450 3A2 Following Oral Administration in Rats," *Journal of Pharmaceutical Sciences* 91(4): 1009-1018, Apr. 2002,.
Astriab-Fisher et al., "Antisense Inhibition of P-glycoprotein Expression Using Peptide-Oligonucleotide Conjugates," *Biochemical Pharmacology* 60:83-90, 2000.
Astriab-Fisher et al., "Conjugates of Antisense Oligonucleotides with the Tat and Antennapedia Cell-Penetrating Peptides: Effects on Cellular Uptake, Binding to Target Sequences, and Biologic Actions," *Pharmaceutical Research* 19(6):744-754, 2002.
Burrer et al., "Antiviral Effects of Antisense Morpholino Oligomers in Murine Coronavirus Infection Models," *Journal of Virology* 81(11):5637-5648, Jun. 2007.
Carlson et al., "In vitro-differentiated TH17 cells mediate lethal acute graft-versus-host disease with severe cutaneous and pulmonary pathologic mainifestations," *Blood* 113(6): 1365-1374, 2009.
Chen et al., "A Concise Method for the Preparation of Peptide and Arginine-Rich Peptide-Conjugated Antisense Oligonucleotide," *Bioconjugate Chem.* 14:532-538, 2003.
Đapić et al., "Biophysical and biological properties of quadruplex oligodeoxyribonucleotides," *Nucleic Acids Research* 31(8):2097-2107, 2003.
Derossi et al., "Trojan peptides: the penetratin system for intracellular delivery," *Trends in Cell Biology* 8(2):84-87, 1998.
Devi, "Prostate cancer: Status of current treatments and emerging antisense-based therapies," *Current Opinion in Molecular Therapeutics* 4(2):138-148, 2002.
Devi et al., "Inhibition of Human Chorionic Gonadotropin β-Subunit Modulates the Mitogenic Effect of c-myc in Human Prostate Cancer Cells," *The Prostate* 53:200-210, 2002.
Egholm et al., "PNA hybridizes to complementary oligonucleotides obeying the Watson-Crick hydrogen-bonding rules," *Nature* 365:566-568, 1993.
Eriksson et al., "Cell Permeabilization and Uptake of Antisense Peptide-Peptide Nucleic Acid (PNA) into *Escherichia coli*," *Journal of Biological Chemistry* 277(9):7144-7147, Mar. 1, 2002.
Gebski et al., "Morpholino antisense oligonucleotide induced dystrophin exon 23 skipping in mdx mouse muscle," *Human Molecular Genetics* 12(15):1801-1811, 2003.
Ghosh et al., "Intracellular Delivery Strategies for Antisense Phosphorodiamidate Morpholino Oligomers," *Antisense & Nucleic Acid Drug Development* 10:263-274, 2000.
Heineke et al., "Genetic Deletion of Myostatin From the Heart Prevents Skeletal Muscle Atrophy in Heart Failure," *Circulation* 121:419-425, 2010.
Hudziak et al., "Resistance of Morpholino Phosphorodiamidate Oligomers to Enzymatic Degradation," *Antisense & Nucleic Acid Drug Development* 6:267-272, 1996.
Iversen, "Phosphorodiamidate Morpholino Oligomers," in Crooke (ed.), *Antisense Drug Technology*, Marcel Dekker, Inc., New York, 2001, pp. 235-238, 17 pages.

(56) References Cited

OTHER PUBLICATIONS

Iversen, "Phosphorodiamidate morpholino oligomers: Favorable properties for sequence-specific gene inactivation," *Current Opinion in Molecular Therapeutics* 3(3):235-238, 2001.
Jearawiriyapaisarn et al., "Sustained Dystrophin Expression Induced by Peptide-conjugated Morpholino Oligomers in the Muscles of mdx Mice," *Mol. Ther.* 16(9): 1624-1629, Sep. 2008.
Kang et al., "Up-Regulation of Luciferase Gene Expression with Antisense Oligonucleotides: Implications and Applications in Functional Assay Development," *Biochemistry* 37:6235-6239, 1998.
Knapp et al., "Resistance to chemotherapeutic drugs overcome by c-Myc inhibition in a Lewis lung carcinoma murine model," *Anti-Cancer Drugs* 14:39-47, 2003.
Kolonin et al., "Synchronous selection of homing peptides for multiple tissues by in vivo phage display," *The FASEB Journal* 20(7):979-981, 2006.
Lebleu et al., "Cell penetrating peptide conjugates of steric block oligonucleotides," *Advanced Drug Delivery Reviews* 60:517-529, 2008.
Marshall et al., "Arginine-rich cell-penetrating peptides facilitate delivery of antisense oligomers into murine leukocytes and alter pre-mRNA splicing," *Journal of Immunological Methods* 325:114-126, 2007.
Matsui et al., "Protein Therapy: In Vivo Protein Transduction by Polyarginine (11R) PTD and Subcellular Targeting Delivery," *Current Protein and Peptide Science* 4:151-157, 2003.
Meade et al., "Exogenous siRNA delivery using peptide transduction domains/cell penetrating peptides," *Advanced Drug Delivery Reviews* 59:134-140, 2007.
Mizutani et al., "Enhancement of Sensitivity of Urinary Bladder Tumor Cells to Cisplatin by c-myc Antisense Oligonucleotide," *Cancer* 74:2546-2554, 1994.
Moskophidis et al., "Resistance of Lymphocytic Choriomeningitis Virus to Alpha/Beta Interferon and to Gamma Interferon," *Journal of Virology* 68(3):1951-1955, Mar. 1994.
Moskophidis et al., "Role of virus and host variables in virus persistence or immunopathological disease caused by a non-cytolytic virus," *Journal of General Virology* 76:381-391, 1995.
Moulton et al., "Cellular Uptake of Antisense Morpholino Oligomers Conjugated to Arginine-Rich Peptides," *Bioconjugate Chem.* 15:290-299, 2004.
Moulton et al., "HIV Tat Peptide Enhances Cellular Delivery of Antisense Morpholino Oligomers," *Antisense & Nucleic Acid Drug Development* 13:31-43, 2003.
Mourich et al., "Antisense compound and method for selectively killing activated T cells," U.S. Appl. No. 60/505,418, filed Sep. 23, 2003, 60 pgs.
Nasevicius et al., "Effective targeted gene 'knockdown' in zebrafish," *Nature Genetics* 26:216-220, Oct. 2000.
Park et al., "Peroxisome Proliferator-Activated Receptor γ Agonist Down-Regulates IL-17 Expression in a Murine Model of Allergic Airway Inflammation," *The Journal of Immunology* 183:3259-3267, 2009.
Qin et al., "In Vivo Evaluation of a Morpholino Antisense Oligomer Directed Against Tumor Necrosis Factor-α," *Antisense & Nucleic Acid Drug Development* 10:11-16, 2000.
Rangachari et al., "T-bet negatively regulates autoimmune myocarditis by suppressing local production of interleukin 17," *The Journal of Experimental Medicine* 203(8):2009-2019, 2006.
Richard et al., "Cell-penetrating Peptides. A Reevaluation of the Mechanism of Cellular Uptake," *Journal of Biological Chemistry* 278(1):585-590, Jan. 3, 2003.
Ricker et al., "c-myc antisense oligonucleotide treatment ameliorates murine ARPKD," *Kidney International* 61:S125-S131, 2002.
Rothbard et al., "Arginine-Rich Molecular Transporters for Drug Delivery: Role of Backbone Spacing in Cellular Uptake," *J. Med. Chem.* 45:3612-3618, 2002.
Samoylova et al., "Elucidation of Muscle-Binding Peptides by Phage Display Screening," *Muscel & Nerve* 22(4):460-466, Apr. 1999.
Shafer et al., "Biological Aspects of DNA/RNA Quadruplexes," *Biopolymers* 56(3):209-227, 2001.
Spence et al., "Generation of cellular immunity to lymphocytic choriomeningitis virus is independent of CD1d1 expression," *Immunology* 104:168-174, 2001.
Stein et al., "Inhibition of Vesivirus Infections in Mammalian Tissue Culture with Antisense Morpholino Oligomers," *Antisense & Nucleic Acid Drug Development* 11:317-325, 2001.
Summerton, "Morpholino antisense oligomers: the case for an RNase H-independent structural type," *Biochimica et Biophysica Acta* 1489:141-158, 1999.
Summerton et al., "Morpholino Antisense Oligomers: Design, Preparation, and Properties," *Antisense & Nucleic Acid Drug Development* 7:187-195, 1997.
Vanin et al., "Synthesis and Application of Cleavable Photoactivable Heterobifunctional reagents," *Biochemistry* 20:6754-6760, 1981.
Vivés et al., "TAT Peptide Internalization: Seeking the Mechanism of Entry," *Current Protein and Peptide Science* 4:125-132, 2003.
Wender et al., "Oligocarbamate Molecular Transporters: Design, Synthesis, and Biological Evaluation of a New Class of Transporters for Drug Delivery," *J. Am. Chem. Soc.* 124:13382-13383, 2002.
Wender et al., "The design, synthesis, and evaluation of molecules that enable r enhance cellular uptake: Peptoid molecular transporters," *PNAS* 97(24): 13003-13008, Nov. 21, 2000.
Wright et al., "The Human IL-17F/IL-17A Heterodimeric Cytokine Signals through the IL-17RA/IL-17RC Receptor Complex," *The Journal of Immunology* 181:2799-2805, 2008.
Wu et al., "Cell-penetrating peptides as transporters for morpholino oligomers: effects of amino acid composition on intracellular delivery and cytotoxicity," *Nucleic Acids Research* 35(15):5182-5191, Aug. 2007.
Yauch et al., "Mouse models of dengue virus infection and disease," *Antiviral Research* 80:81-93, 2008.
Yin et al., "Effective Exon Skipping and Restoration of Dystrophin Expression by Peptide Nucleic Acid Antisense Oligonucleotides in mdx Mice," *Molecular Therapy* 16(1):38-45, Jan. 2008.
Yoo et al., "PAMAM Dendrimers as Delivery Agents for Antisense Oligonucleotides," *Pharmaceutical Research* 16 (12):1799-1804, 1999.
Youngblood et al., "Stability of Cell-Penetrating Peptide-Morpholino Oligomer Conjugates in Human Serum and in Cells," *Bioconjugate Chem.* 18:50-60, 2007.
Zhang et al., "Construction of a novel chimera consisting of a chelator-containing Tat peptide conjugated to a morpholino antisense oligomers for technetium-99m labeling and accelerating cellular kinetics," *Nuclear Medicine and Biology* 33:263-269, 2006.
Zhou et al., "IL-17A versus IL-17F induced intracellular signal transduction pathways and modulation by IL-17RA and IL-17RC RNA interference in AGS gastric adenocarcinoma cells," *Cytokine* 38:157-164, 2007.
Zubin et al., "Oligonucleotide-peptide conjugates as potential antisense agents," *FEBS Letters* 456:59-62, 1999.
Andreasen et al., "Expression and Functional Importance of Collagen-Binding Integrins, α2β1 and α2β1, on Virus-Activated T Cells," *The Journal of Immunology* 171:2804-2811, 2003.
Blattman et al., "Therapeutic use of IL-2 to enhance antiviral T-cell responses in vivo," *Nature Medicine* 9(5):540-547, May 2003.
NCBI, "Predicted Protein [Nematostella Vectensis]," NCBI Reference Sequence: XP_0011635778.1, retrieved from http://www.ncbi.nlm.nih.gov/protein/156391881, on Dec. 9, 2014, 1 page.
Wherry et al., "Viral Persistence Alters CD8 T-Cell Immunodominance and Tissue Distribution and Results in Distinct Stages of Functional Impairment," *Journal of Virology* 77(8):4911-4927, Apr. 2003.
Weller et al., "Antibacterial Antisense Oligonucleotide and Method," U.S. Appl. No. 14/977,451, filed Dec. 21, 2015, 157 pages.
Sazani et al. (2002) "Systemically delivered antisense oligomers upregulate gene expression in mouse tissues," Nature Biotechnology, 20:1228-1233.
Extended European Search Report for European Application No. 18180179.6, dated Jan. 21, 2019.
McClorey et al., (2006) "Induced dystrophin exon skipping in human muscle explants," Neuromuscular Disorders, 16:583-590.

(56) References Cited

OTHER PUBLICATIONS

McClorey et al., (2006) "Antisense oligonucleotide-induced exon skipping restores dystrophin expression in vitro in a canine model of DMD," Gene Therapy, 13:1373-1381.

* cited by examiner

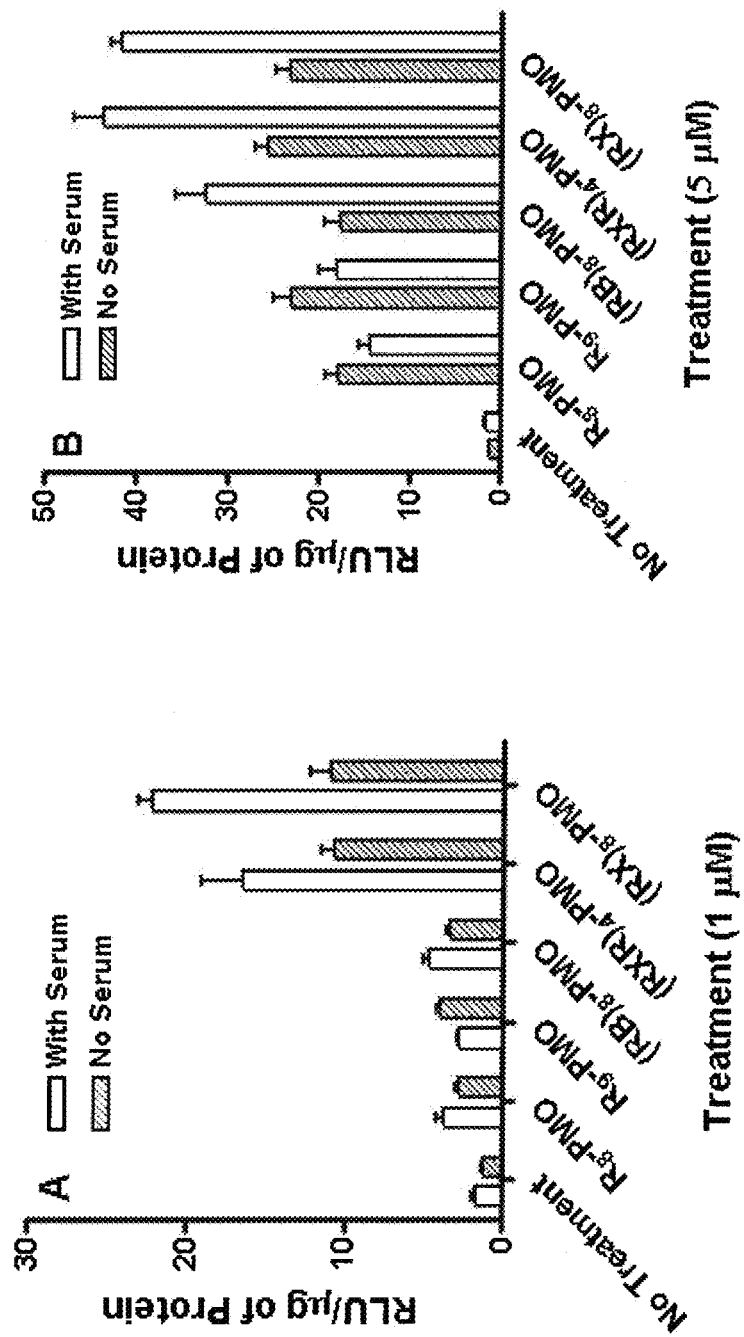
Figs. 3A-B

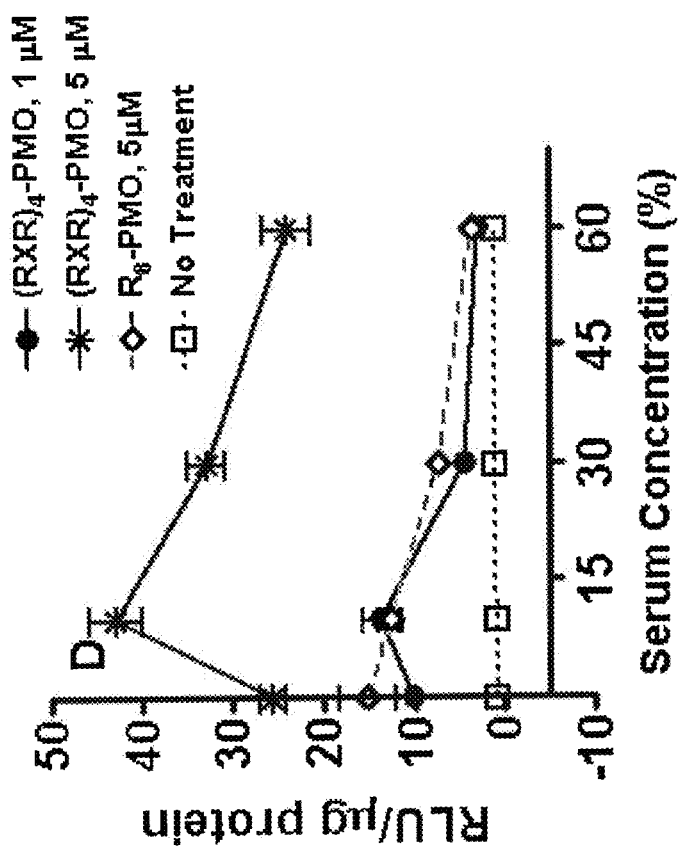
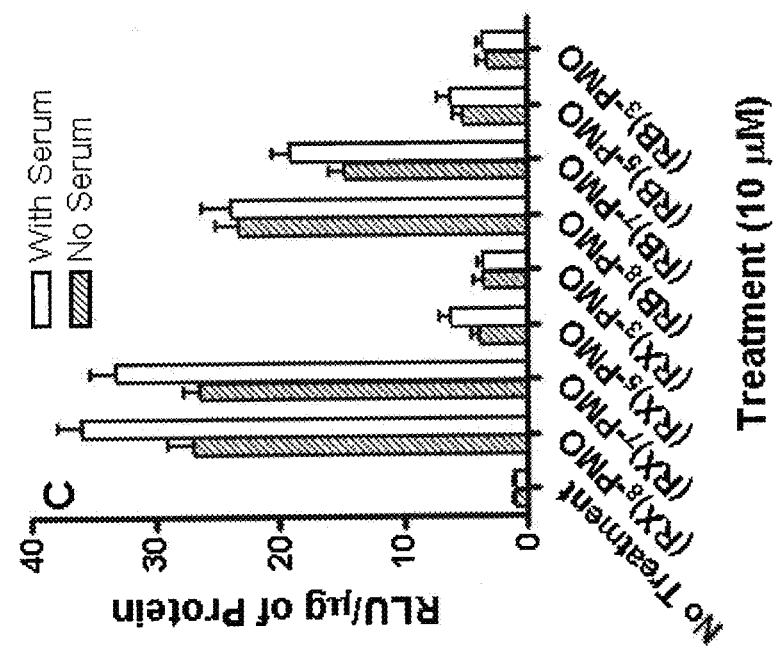
Figs. 3C-D

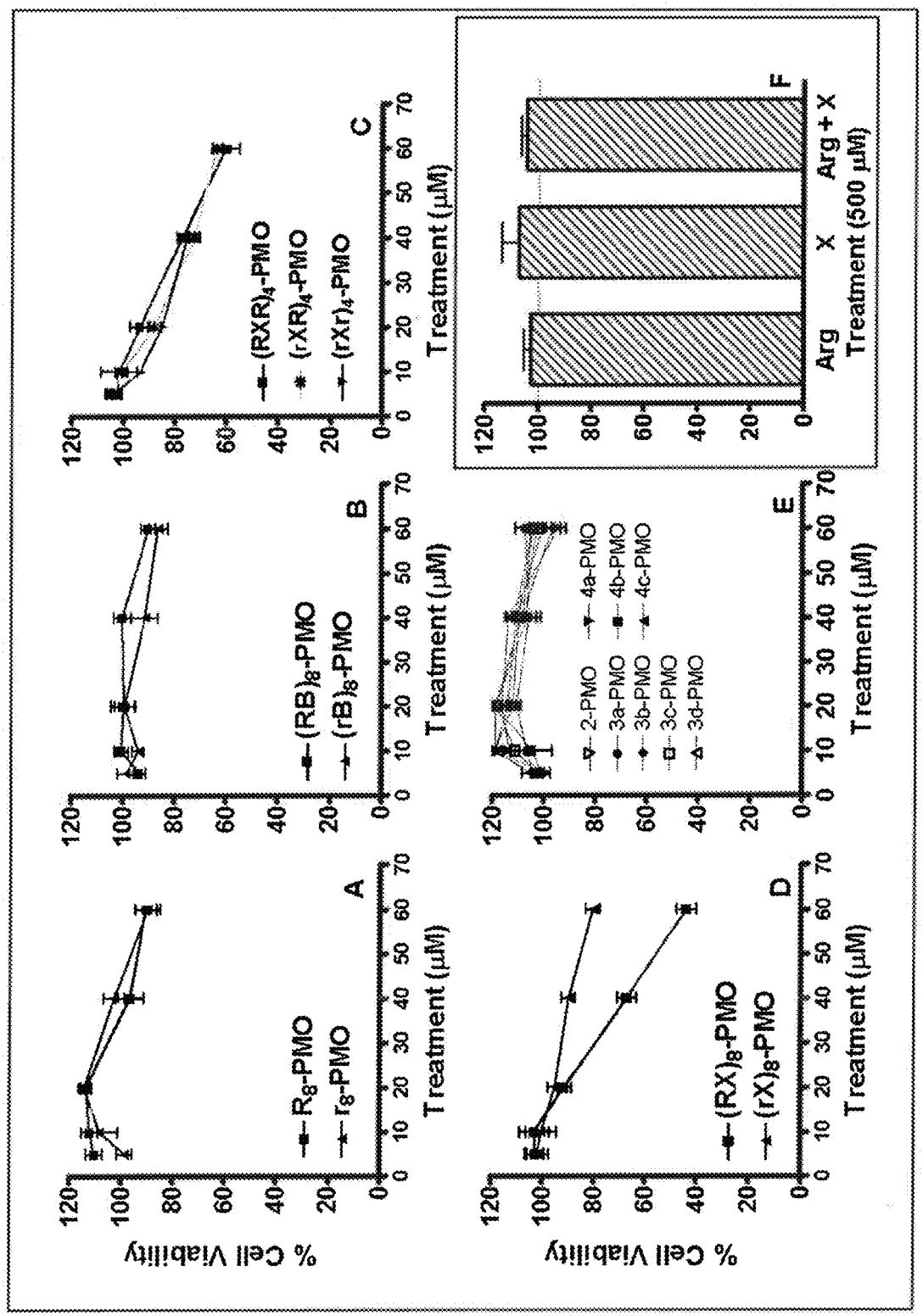
Figs. 5A-F

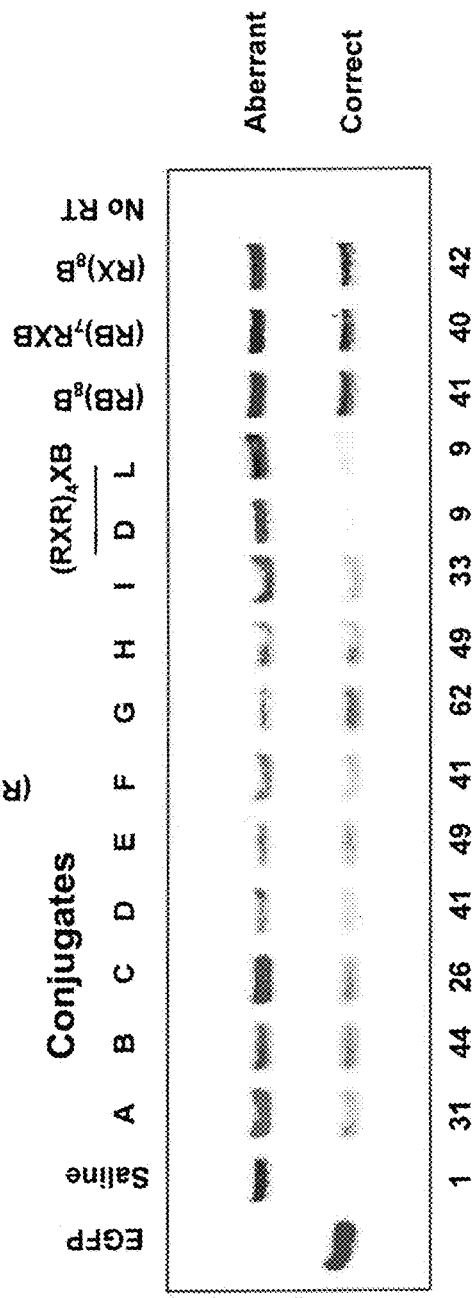
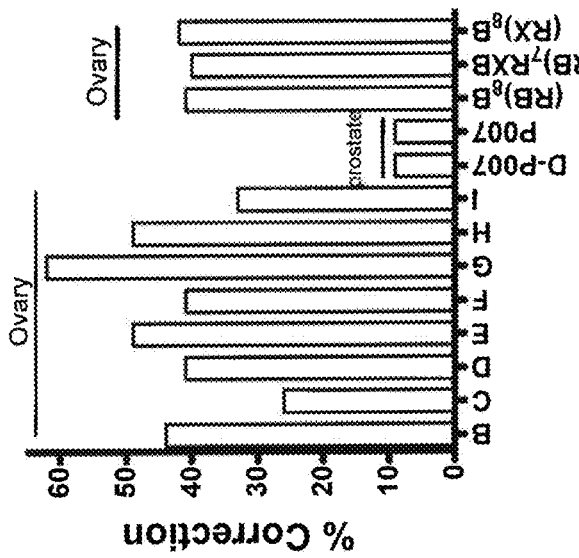

Fig. 7C

A = R$_9$ (SEQ ID NO. 3)
B = (RXRRBR)$_2$XB (SEQ ID NO. 19)
C = (RXR)$_3$RBRXB (SEQ ID NO. 26)
D = (RB)$_5$RXRBRXB (SEQ ID NO. 20)
E = (RBRBRBRX)$_2$X (SEQ ID NO. 21)
F = X(RB)$_3$RX(RB)$_3$RX (SEQ ID NO. 22)
G = (RBRX)$_4$B (SEQ ID NO. 23)
H = (RB)$_4$(RX)$_4$B (SEQ ID NO. 24)
I = RX(RB)$_2$RX(RB)$_3$RX (SEQ ID NO. 25)
D-P007 = (rXr)$_4$XB (SEQ ID NO. 13)
P007 = (RXR)$_4$XB (SEQ ID NO. 11)
(RB)$_8$ (SEQ ID NO. 14)
(RB)$_7$RXB (SEQ ID NO. 27)
(RX)$_8$B (SEQ ID NO. 6)

Note: All samples are from ovary, except D- and L-(RXR)$_4$XB which are from prostate gland.

Fig. 7F
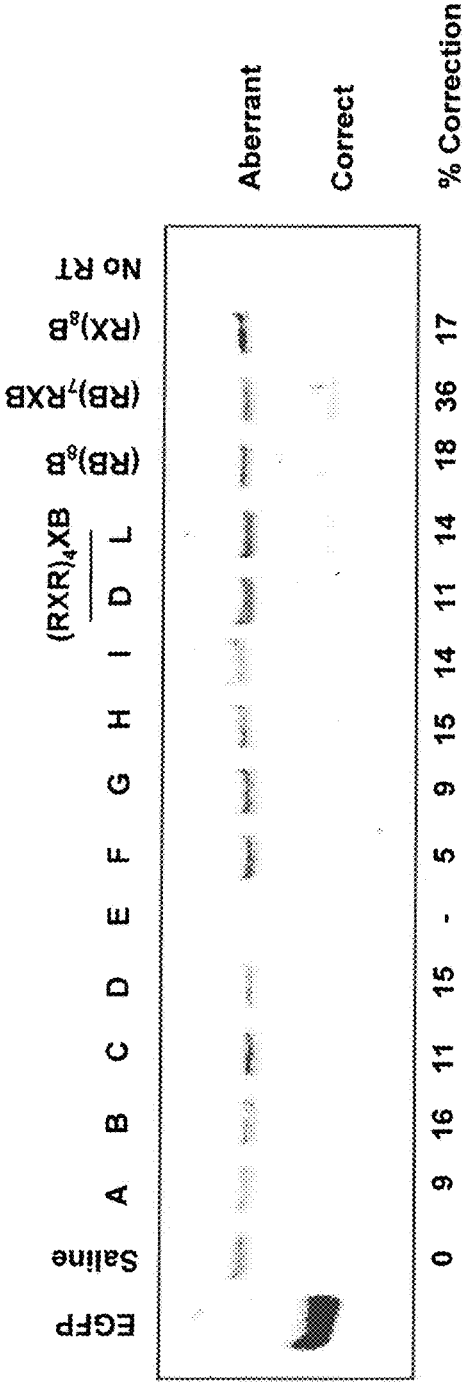
A = R₉ (SEQ ID NO. 3)
B = (RXRRBR)₂XB (SEQ ID NO. 19)
C = (RXR)₃RBRXB (SEQ ID NO. 26)
D = (RB)₅RXRBRXB (SEQ ID NO. 20)
E = (RBRBRBRX)₂X (SEQ ID NO. 21)
F = X(RB)₃RX(RB)₃RX (SEQ ID NO. 22)
G = (RBRX)₄B (SEQ ID NO. 23)
H = (RB)₄(RX)₄B (SEQ ID NO. 24)
I = RX(RB)₂RX(RB)₃RX (SEQ ID NO. 25)
D-P007 = (rXr)₄XB (SEQ ID NO. 13)
P007 = (RXR)₄XB (SEQ ID NO. 11)
(RB)₆B (SEQ ID NO. 14)
(RB)₇RXB (SEQ ID NO. 27)
(RX)₈B (SEQ ID NO. 6)
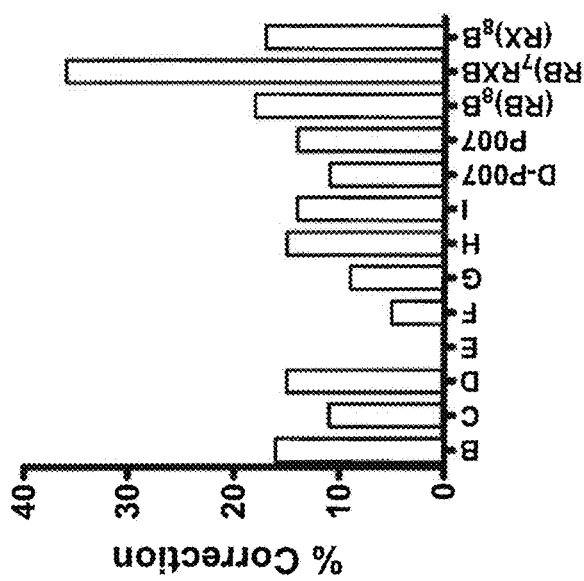

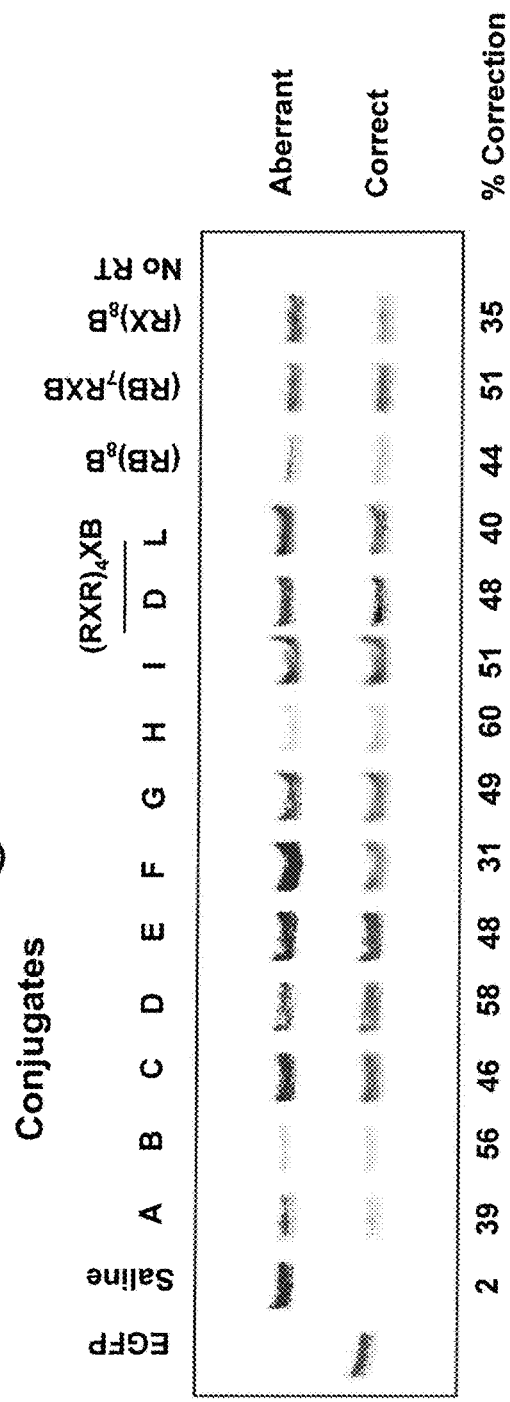
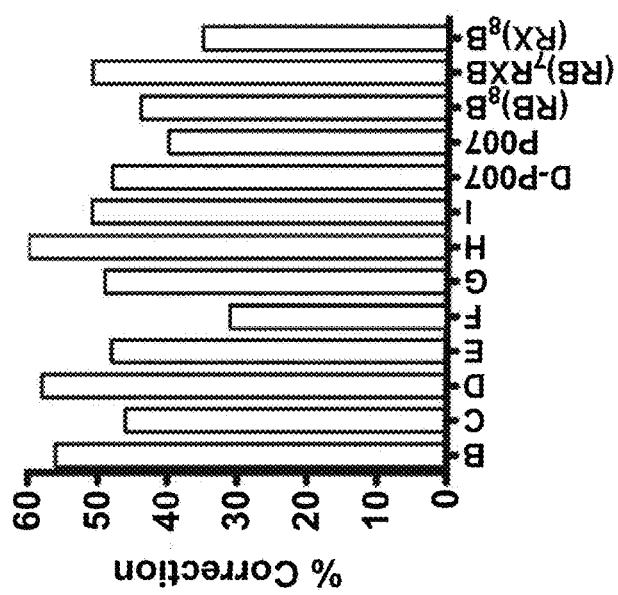
Fig. 7G
A = R8 (SEQ ID NO. 3)
B = (RXRRBR)2XB (SEQ ID NO. 19)
C = (RXR)3RBRXB (SEQ ID NO. 26)
D = (RB)5RXRBRXB (SEQ ID NO. 20)
E = (RBRBRBRX)2X (SEQ ID NO. 21)
F = X(RB)3RX(RB)3RX (SEQ ID NO. 22)
G = (RBRX)4B (SEQ ID NO. 23)
H = (RB)4(RX)4B (SEQ ID NO. 24)
I = RX(RB)2RX(RB)3RX (SEQ ID NO. 25)
D-P007 = (rXr)4XB (SEQ ID NO. 13)
P007 = (RXR)4XB (SEQ ID NO. 11)
(RB)8 (SEQ ID NO. 14)
(RB)7RXB (SEQ ID NO. 27)
(RX)8B (SEQ ID NO. 6)

Fig. 7I
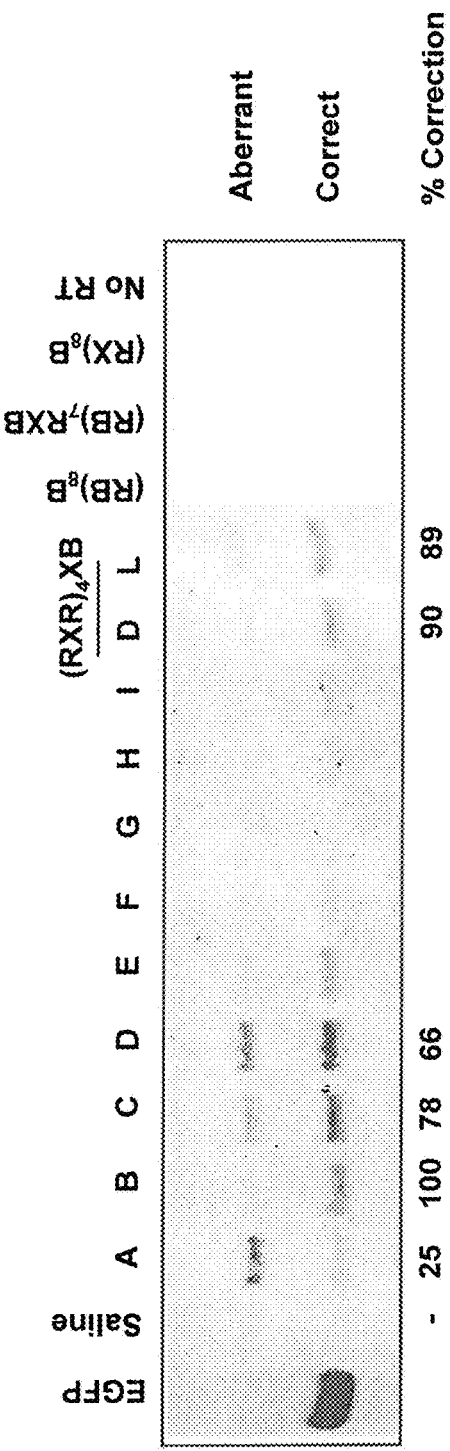
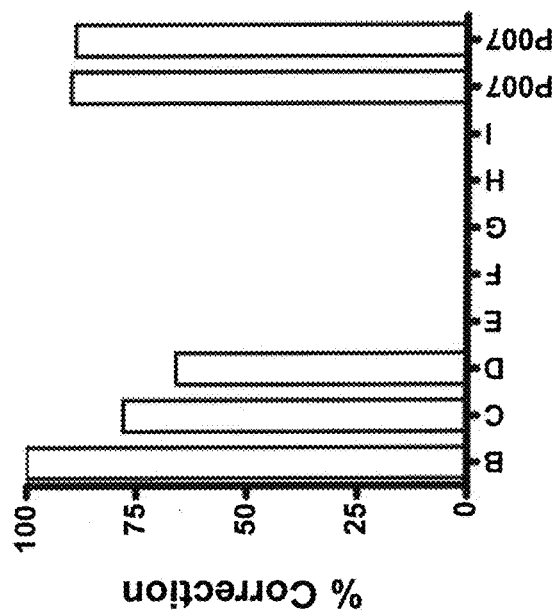
A = R₈ (SEQ ID NO. 3)
B = (RXRRBR)₂XB (SEQ ID NO. 19)
C = (RXR)₃RBRXB (SEQ ID NO. 26)
D = (RB)₅RXRBRXB (SEQ ID NO. 20)
E = (RBRBRBRX)₂X (SEQ ID NO. 21)
F = X(RB)₃RX(RB)₃RX (SEQ ID NO. 22)
G = (RBRX)₄B (SEQ ID NO. 23)
H = (RB)₄(RX)₄B (SEQ ID NO. 24)
I = RX(RB)₂RX(RB)₃RX (SEQ ID NO. 25)
D-P007 = (rXr)₄XB (SEQ ID NO. 13)
P007 = (RXR)₄XB (SEQ ID NO. 11)
(RB)₈ (SEQ ID NO. 14)
(RB)₇RXB (SEQ ID NO. 27)
(RX)₈B (SEQ ID NO. 6)

Fig. 7J
A = R₈ (SEQ ID NO. 3)
B = (RXRRBR)₂XB (SEQ ID NO. 19)
C = (RXR)₃RBRXB (SEQ ID NO. 26)
D = (RB)₅RXRBRXB (SEQ ID NO. 20)
E = (RBRBRBRX)₂X (SEQ ID NO. 21)
F = X(RB)₃RX(RB)₃RX (SEQ ID NO. 22)
G = (RBRX)₄B (SEQ ID NO. 23)
H = (RB)₄(RX)₄B (SEQ ID NO. 24)
I = RX(RB)₂RX(RB)₃RX (SEQ ID NO. 25)
D-P007 = (rXr)₄XB (SEQ ID NO. 13)
P007 = (RXR)₄XB (SEQ ID NO. 11)
(RB)₈B (SEQ ID NO. 14)
(RB)₇RXB (SEQ ID NO. 27)
(RX)₈B (SEQ ID NO. 6)
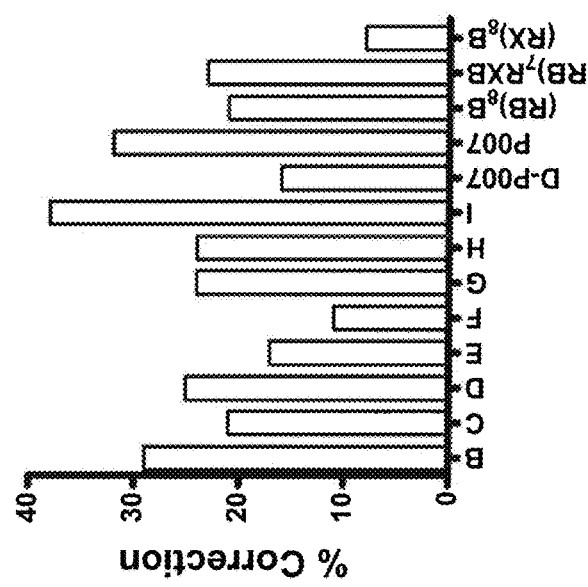
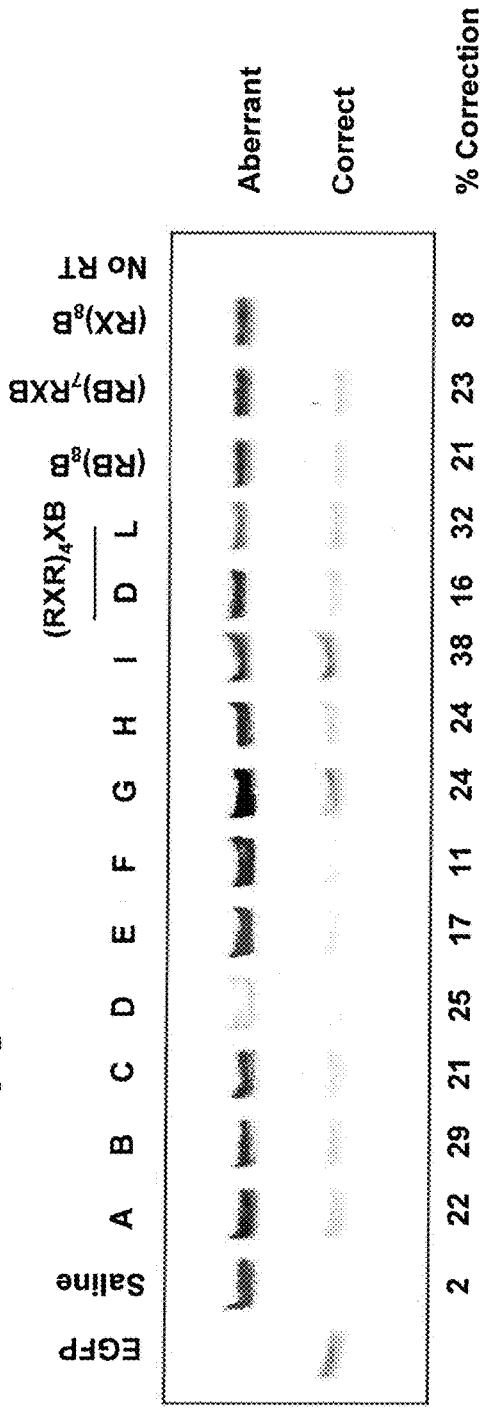

Fig. 7K
A = R$_8$ (SEQ ID NO. 3)
B = (RXRRBR)$_2$XB (SEQ ID NO. 19)
C = (RXR)$_3$RBRXB (SEQ ID NO. 26)
D = (RB)$_5$RXRBRXB (SEQ ID NO. 20)
E = (RBRBRBRX)$_2$X (SEQ ID NO. 21)
F = X(RB)$_3$RX(RB)$_3$RX (SEQ ID NO. 22)
G = (RBRX)$_4$B (SEQ ID NO. 23)
H = (RB)$_4$(RX)$_4$B (SEQ ID NO. 24)
I = RX(RB)$_2$RX(RB)$_3$RX (SEQ ID NO. 25)
D-P007 = (rXr)$_4$XB (SEQ ID NO. 13)
P007 = (RXR)$_4$XB (SEQ ID NO. 11)
(RB)$_8$ (SEQ ID NO. 14)
(RB)$_7$RXB (SEQ ID NO. 27)
(RX)$_8$B (SEQ ID NO. 6)
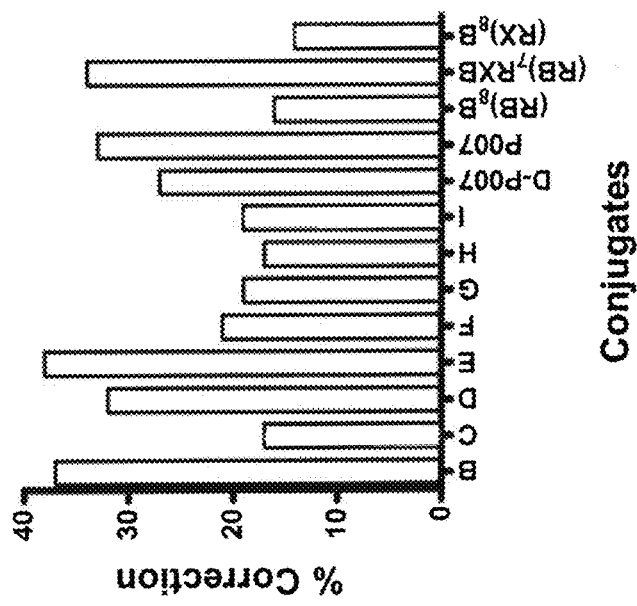
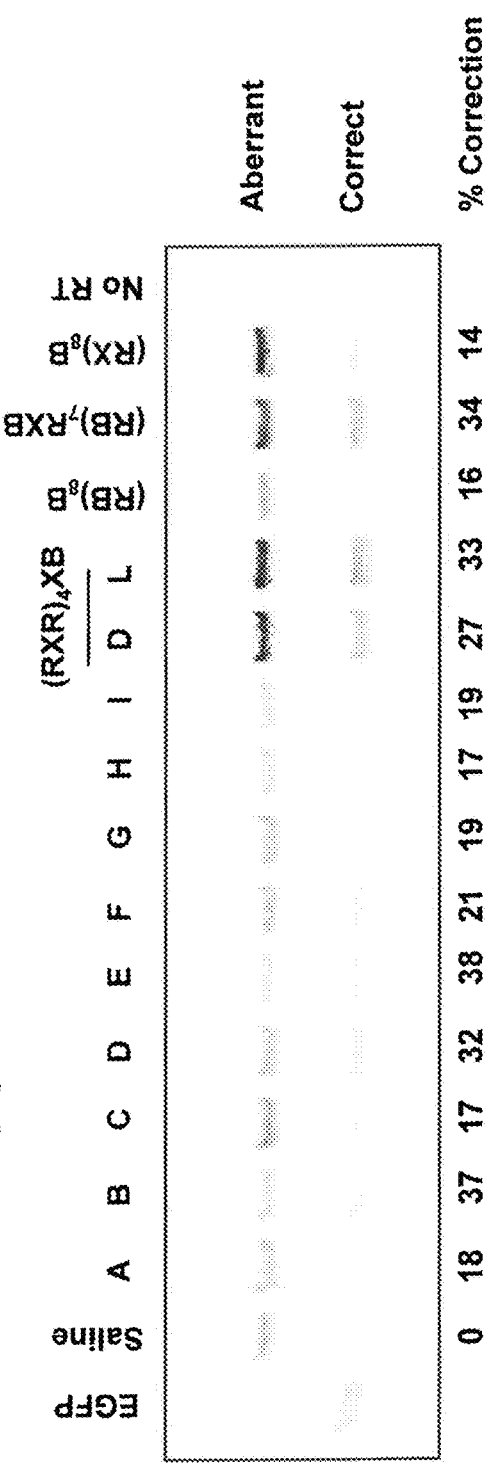

Fig. 7L
A = $R_8$ (SEQ ID NO. 3)
B = $(RXRRBR)_2XB$ (SEQ ID NO. 19)
C = $(RXR)_3RBRXB$ (SEQ ID NO. 26)
D = $(RB)_5RXRBRXB$ (SEQ ID NO. 20)
E = $(RBRBRBRX)_2X$ (SEQ ID NO. 21)
F = $X(RB)_3RX(RB)_3RX$ (SEQ ID NO. 22)
G = $(RBRX)_4B$ (SEQ ID NO. 23)
H = $(RB)_4(RX)_4B$ (SEQ ID NO. 24)
I = $RX(RB)_2RX(RB)_3RX$ (SEQ ID NO. 25)
D-P007 = $(rXr)_4XB$ (SEQ ID NO. 13)
P007 = $(RXR)_4XB$ (SEQ ID NO. 11)
$(RB)_8B$ (SEQ ID NO. 14)
$(RB)_7RXB$ (SEQ ID NO. 27)
$(RX)_8B$ (SEQ ID NO. 6)
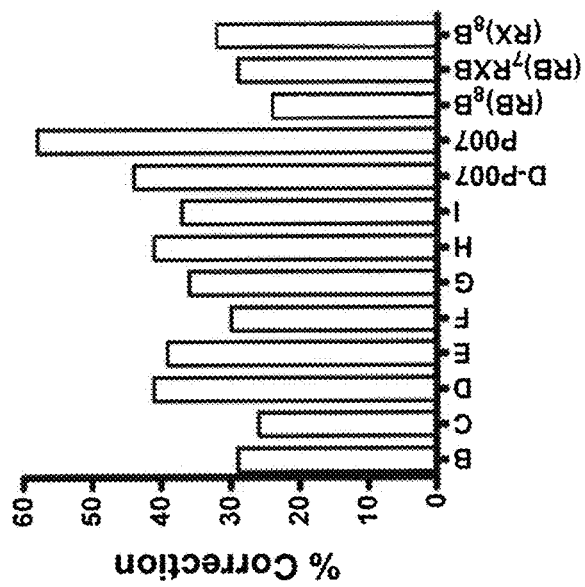
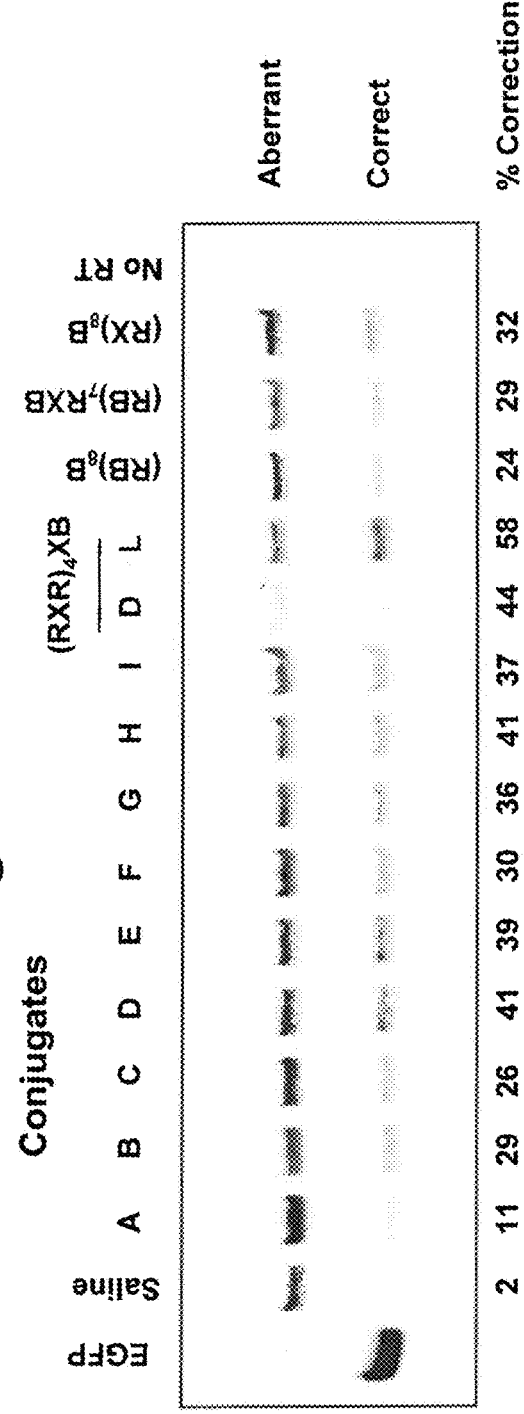

Fig. 7M
A = R₈ (SEQ ID NO. 3)
B = (RXRRBR)₂XB (SEQ ID NO. 19)
C = (RXR)₃RBRXB (SEQ ID NO. 26)
D = (RB)₅RXRBRXB (SEQ ID NO. 20)
E = (RBRBRBRX)₂X (SEQ ID NO. 21)
F = X(RB)₃RX(RB)₃RX (SEQ ID NO. 22)
G = (RBRX)₄B (SEQ ID NO. 23)
H = (RB)₄(RX)₄B (SEQ ID NO. 24)
I = RX(RB)₂RX(RB)₃RX (SEQ ID NO. 25)
D-P007 = (rXr)₄XB (SEQ ID NO. 13)
P007 = (RXR)₄XB (SEQ ID NO. 11)
(RB)₈B (SEQ ID NO. 14)
(RB)₇RXB (SEQ ID NO. 27)
(RX)₈B (SEQ ID NO. 6)
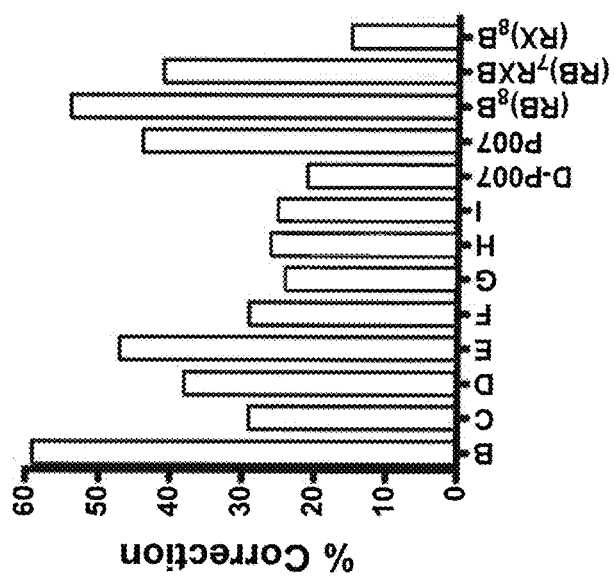
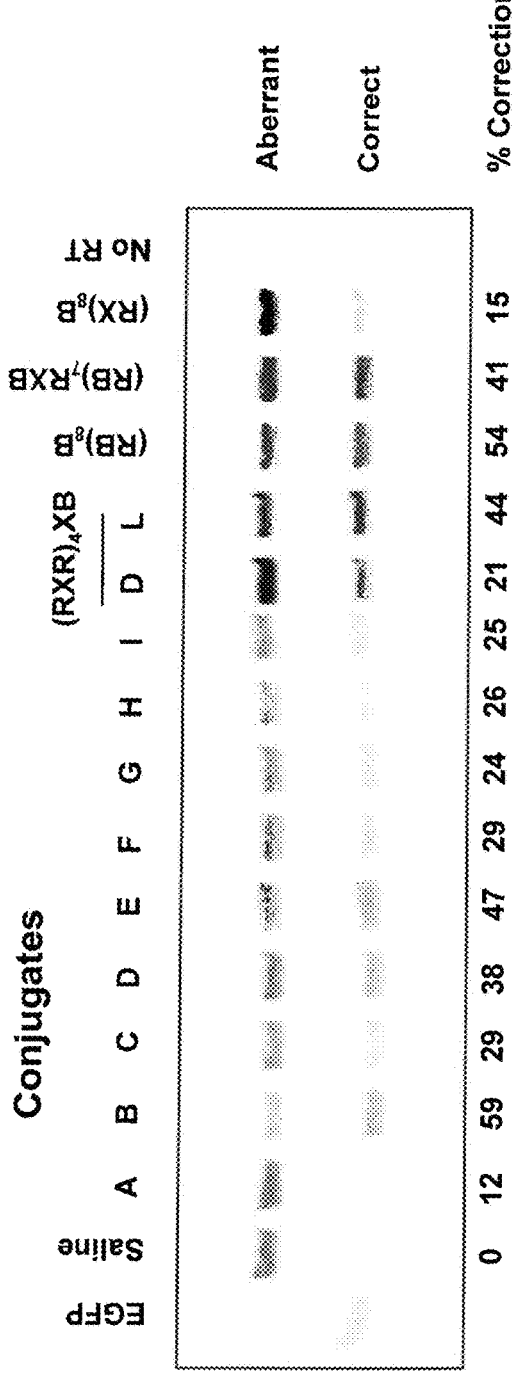

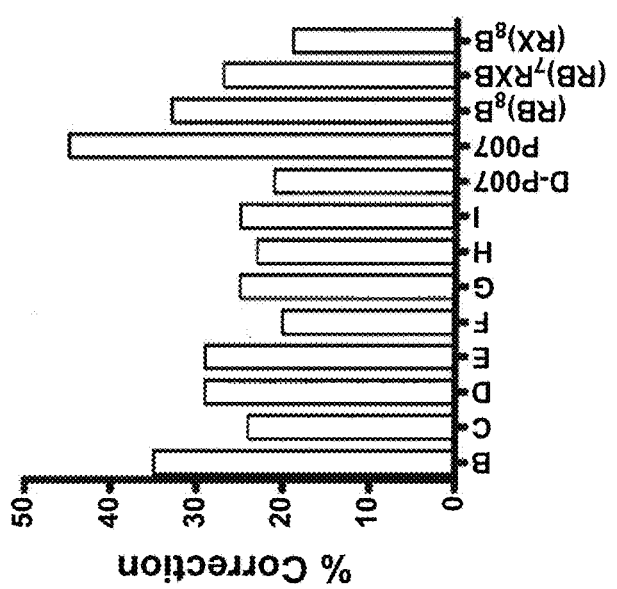
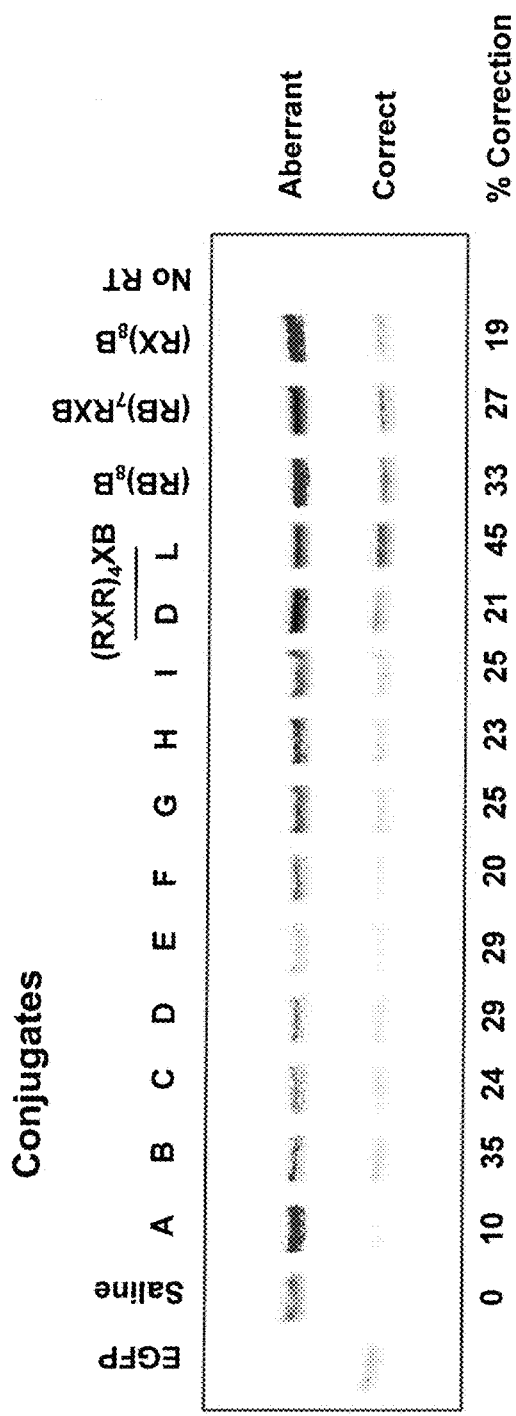
Fig. 7N
A = R$_6$ (SEQ ID NO. 3)
B = (RXRRBR)$_2$XB (SEQ ID NO. 19)
C = (RXR)$_3$RBRXB (SEQ ID NO. 26)
D = (RB)$_5$RXRBRXB (SEQ ID NO. 20)
E = (RBRBRBRX)$_2$X (SEQ ID NO. 21)
F = X(RB)$_3$RX(RB)$_3$RX (SEQ ID NO. 22)
G = (RBRX)$_4$B (SEQ ID NO. 23)
H = (RB)$_4$(RX)$_4$B (SEQ ID NO. 24)
I = RX(RB)$_2$RX(RB)$_3$RX (SEQ ID NO. 25)
D-P007 = (rXr)$_4$XB (SEQ ID NO. 13)
P007 = (RXR)$_4$XB (SEQ ID NO. 11)
(RB)$_8$ (SEQ ID NO. 14)
(RB)$_7$RXB (SEQ ID NO. 27)
(RX)$_8$B (SEQ ID NO. 6)

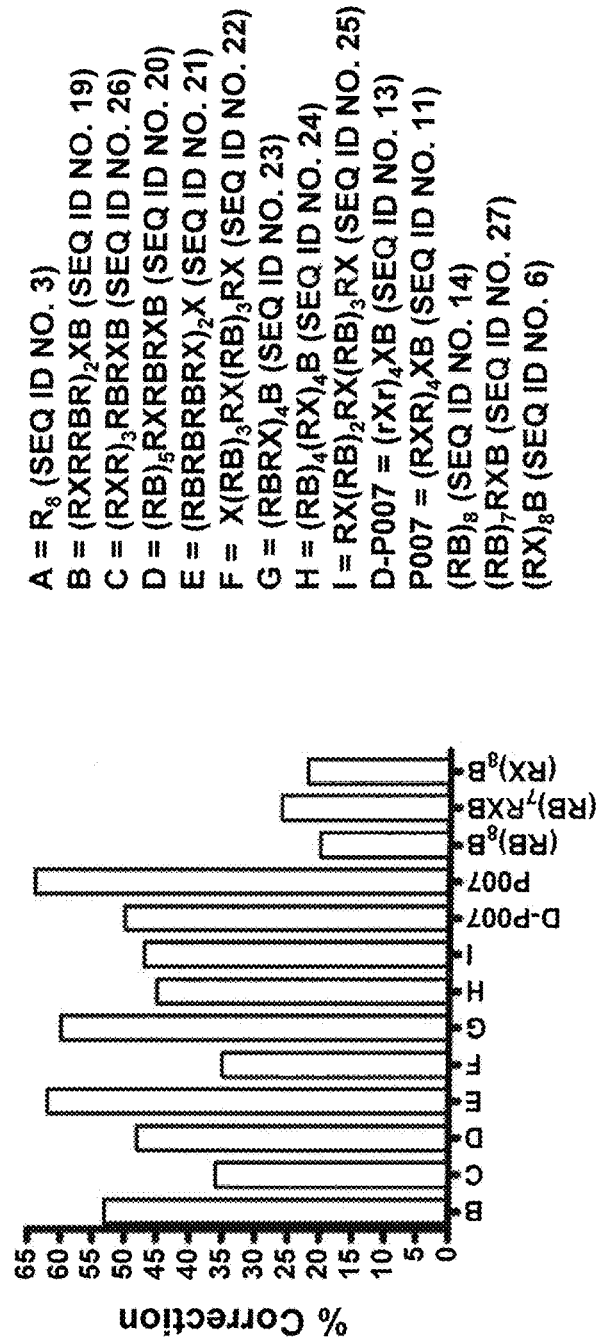
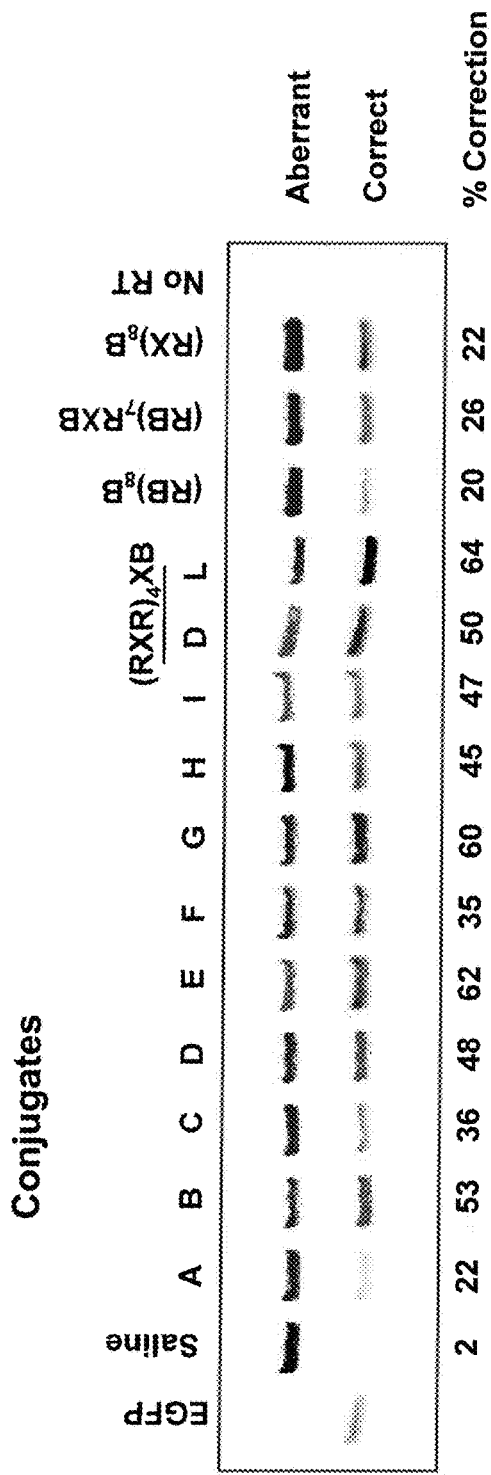
Fig. 7O

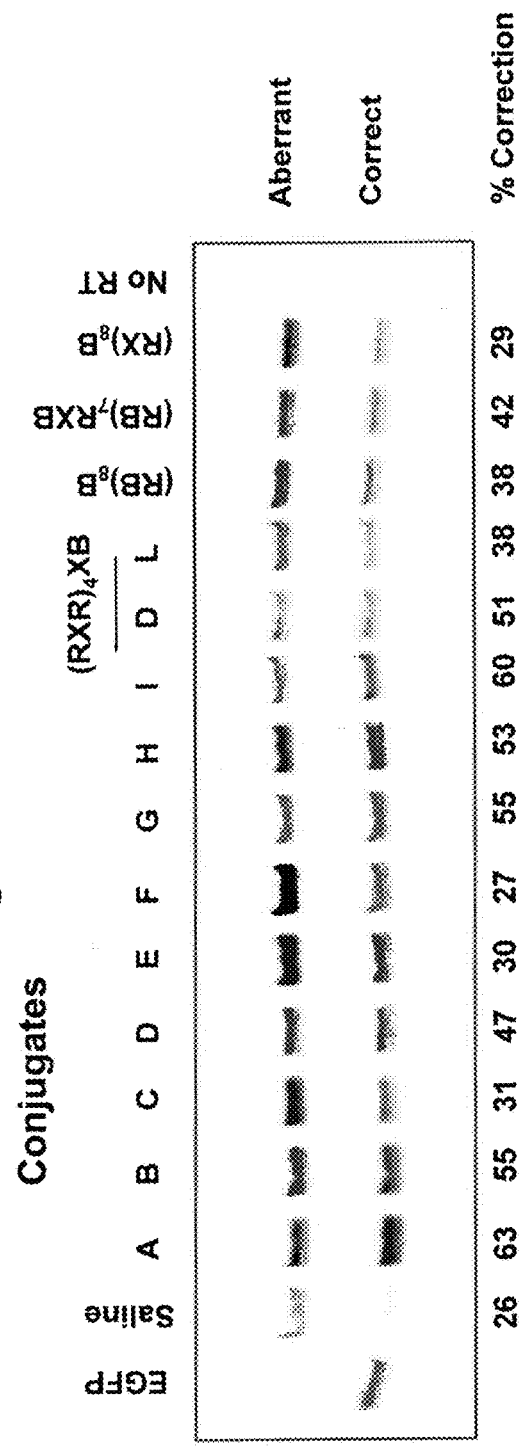
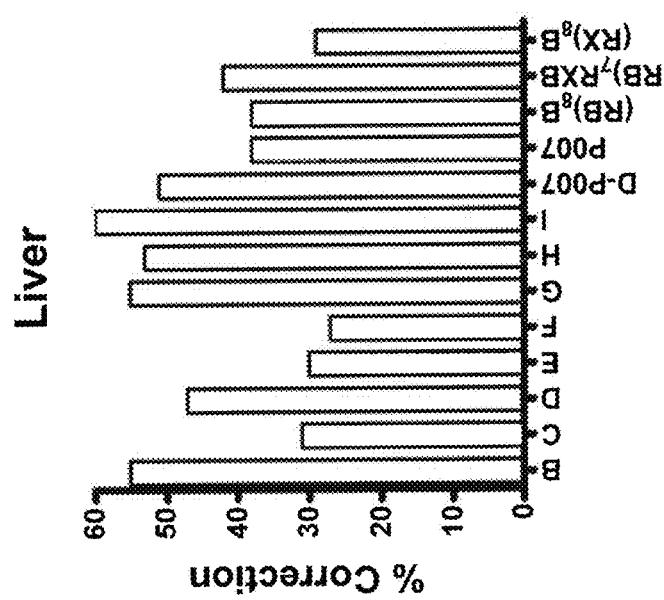
Fig. 7P

Structures of PMO and PPMO (A) and restoration of dystrophin in muscles of mdx mice (aged 4–5 weeks) after a single i.v. injection of 30 mg/kg of M23d-CP06062 PPMO Wu B. et al. PNAS 2008;105:14814-14819

Restoration of dystrophin in bodywide muscles of mdx mice (age 4-5 weeks) after six i.v. injections of 30 mg/kg of M23d-CP06062 PPMO at biweekly intervals Wu B. et.al. PNAS 2008;105:14814-14819

Restoration of dystrophin in skeletal and smooth muscles after six cycles of 30-mg/kg M23d-CP06062 PPMO injection Wu B. et.al. PNAS 2008;105:14814-14819

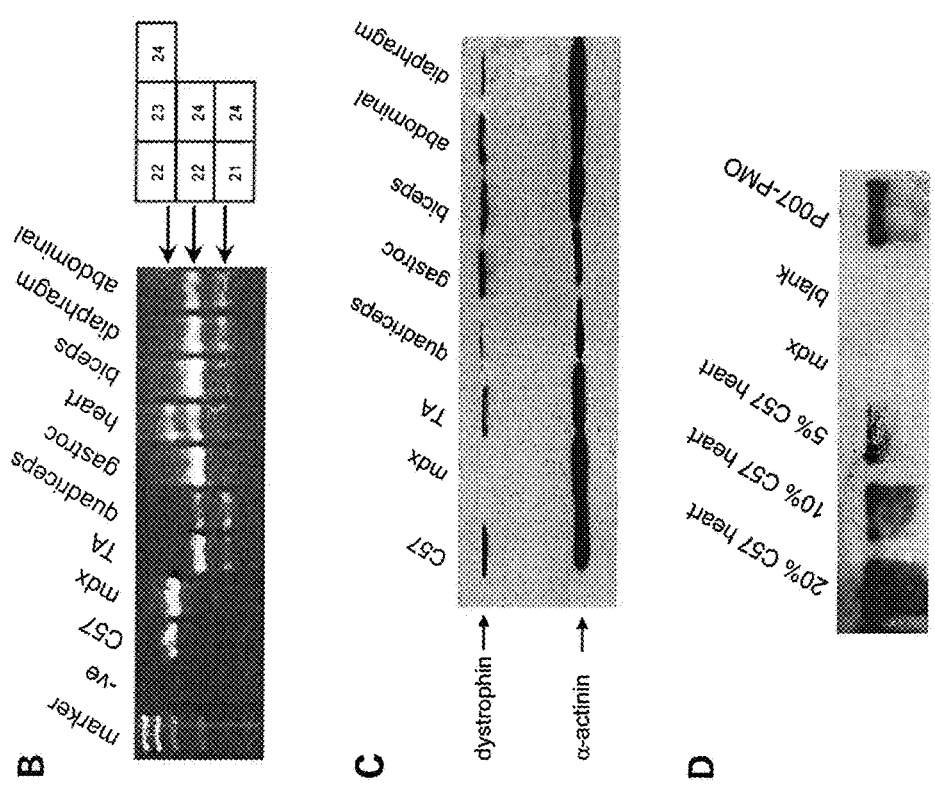
Fig. 13B-D

COMPOUND AND METHOD FOR TREATING MYOTONIC DYSTROPHY

CROSS-REFERENCE TO RELATED APPLICATIONS

This application is a continuation of U.S. patent application Ser. No. 13/219,401, filed Aug. 26, 2011, now U.S. Pat. No. 8,741,863, which is a continuation of U.S. patent application Ser. No. 12/493,140, filed Jun. 26, 2009, which is a continuation-in-part of U.S. patent application Ser. No. 12/217,040, filed Jun. 30, 2008, which claims the benefit of U.S. Provisional Application No. 60/937,725, filed Jun. 29, 2007; these applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 583023_SPT-8083CON2_ST25.txt. The text file is 20,642 bytes, was created on Feb. 7, 2020, and is being submitted electronically via EFS-Web.

FIELD OF THE INVENTION

The invention relates to an antisense compound and method for treating myotonic dystrophy DM1 and DM2.

REFERENCES

Abes, S., H. M. Moulton et al. (2006). "Vectorization of morpholino oligomers by the (R-Ahx-R)$_4$ peptide allows efficient splicing correction in the absence of endosomolytic agents." *J Control Release* 116(3): 304-13.

Arap, W. et al. (2004). "Human and mouse targeting peptides identified by phage display." U.S. Appn. Pubn. No. 20040170955.

Behlke, M. A. (2006). "Progress towards in vivo use of siRNAs." *Mol Ther* 13(4): 644-70.

Alter, J., F. Lou et al. (2006). "Systemic delivery of morpholino oligonucleotide restores dystrophin expression bodywide and improves dystrophic pathology." *Nat Med* 12(2): 175-7.

Chen, C. P., L. R. Zhang et al. (2003). "A concise method for the preparation of peptide and arginine-rich peptide-conjugated antisense oligonucleotide." *Bioconjug Chem* 14(3): 532-8.

Gebski, B. L., C. J. Mann et al. (2003). "Morpholino antisense oligonucleotide induced dystrophin exon 23 skipping in mdx mouse muscle." *Hum Mol Genet* 12(15): 1801-11.

Jearawiriyapaisarn, Moulton et al. (2008). "Sustained dystrophin expression induced by peptide-conjugated morpholino oligomers in the muscles of mdx mice." *Mol Therapy*, Jun. 10, 2008 (advance online publication).

Kang, S. H., M. J. Cho et al. (1998). "Up-regulation of luciferase gene expression with antisense oligonucleotides: implications and applications in functional assay development." *Biochemistry* 37(18): 6235-9.

Kolonin, M. G., J. Sun et al. (2006). "Synchronous selection of homing peptides for multiple tissues by in vivo phage display." *FASEB J* 20(7): 979-81.

Meade, B. R. and S. F. Dowdy (2007). "Exogenous siRNA delivery using peptide transduction domains/cell penetrating peptides." *Adv Drug Deliv Rev* 59(2-3): 134-40.

Richard, J. P., K. Melikov et al. (2003). "Cell-penetrating peptides. A reevaluation of the mechanism of cellular uptake." *J Biol Chem* 278(1): 585-90.

Rothbard, J. B., E. Kreider et al. (2002). "Arginine-rich molecular transporters for drug delivery: role of backbone spacing in cellular uptake." *J Med Chem* 45(17): 3612-8.

Samoylova, T. I. and B. F. Smith (1999). "Elucidation of muscle-binding peptides by phage display screening." *Muscle Nerve* 22(4): 460-6.

Sazani, P., F. Gemignani et al. (2002). "Systemically delivered antisense oligomers upregulate gene expression in mouse tissues." *Nat Biotechnol* 20(12): 1228-33.

Sontheimer, E. J. (2005). "Assembly and function of RNA silencing complexes." *Nat Rev Mol Cell Biol* 6(2): 127-38.

Vodyanoy, V. et al. (2003). "Ligand sensor devices and uses thereof." U.S. Appn. Pubn. No. 20030640466.

Wu, R. P., D. S. Youngblood et al. (2007). "Cell-penetrating peptides as transporters for morpholino oligomers: effects of amino acid composition on intracellular delivery and cytotoxicity." *Nucleic Acids Res.* 35(15):5182-91. (Epub 2007 Aug. 1.)

Youngblood, D. S., S. A. Hatlevig et al. (2007). "Stability of cell-penetrating peptide-morpholino oligomer conjugates in human serum and in cells." *Bioconjug Chem* 18(1): 50-60.

BACKGROUND OF THE INVENTION

The practical utility of many drugs having potentially useful biological activity is often hindered by problems in delivering such drugs to their targets. The delivery of drugs and other compounds into cells generally occurs from an aqueous cellular environment and entails penetration of a lipophilic cell membrane to gain cell entry.

Oligonucleotides and their analogs are one class of potentially useful drugs whose practical utility has been impeded due to insufficient cellular uptake, and it has been proposed heretofore to enhance uptake of oligonucleotides through conjugation of arginine-rich peptides containing non-α amino acids (see, for example, Chen, Zhang et al. 2003; Abes, Moulton et al. 2006; Youngblood, Hatlevig et al. 2007; and Wu et al. 2007). The use of arginine-rich peptides has been reported for the transport of therapeutic drugs, more generally (see, for example, Rothbard, Kreider et al. 2002).

Studies by the inventors and others (Chen, Zhang et al. 2003; Abes, Moulton et al. 2006; Youngblood, Hatlevig et al. 2007) have established that incorporation of unnatural amino acids can confer enhanced stability to peptide carriers and enhanced antisense activity to conjugated oligomers, and therefore improve the potential of CPPs (cell penetrating peptides) to deliver therapeutic macromolecules.

Parent U.S. application Ser. No. 12/217,040 discloses studies showing that two of the CPPs reported in the application are effective in selectively targeting oligonucleotides to muscle tissue, particularly heart muscle, but also including quadricep (skeletal) muscle. These two peptides have the generic sequence (RXRR(B/X)R)$_2$XB, where R is arginine; B is β-alanine; and each X is —C(O)—(CH$_2$)$_n$—NH—, where n is 4-6. Additional studies reported herein confirm the ability of these two CPPs to enhance the uptake and functioning in muscles of oligonucleotide antisense compounds conjugated to one of the CCPs.

The parent application disclosed and claimed the use of these two CPPs for targeting antisense oligonucleotides to muscle tissue, in treating certain muscle pathologies. For example, in treating Duchenne muscular dystrophy (DMD), an oligonucleotide designed to promote exon skipping in a mutated dystrophin pre-mRNA (for purposes of restoring the proper reading frame in a mutated dystrophin mRNA), is conjugated to one of the CPPs, for enhanced uptake and functioning the oligonucleotide in muscle tissue, including both skeletal and heart muscle. In treating DMD, it is advantageous to effectively target and treat heart muscle, since improvement in skeletal muscle function alone can place a DMD-compromised heart under even greater stress.

The present invention applies this strategy additionally to the treatment of myotonic dystrophy MD1 and MD2 in muscle tissue, including skeletal and heart muscle tissue. This condition is associated with long polyCUG (MD1) and polyCCUG (MD2) repeats in the 3'-UTR regions of the transcript dystrophia myotonica protein kinase (DMPK). While normal individuals have as many as 30 CTG repeats, DM1 patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP). Several RNA-BP have been implicated in the disease, including muscleblind-like (MBNL) proteins and CUG-binding protein (CUGBP). MBNL proteins are homologous to *Drosophila* muscleblind (Mbl) proteins necessary for photoreceptor and muscle differentiation. MBNL and CUGBP have been identified as antagonistic splicing regulators of transcripts affected in DM1 such as cardiac troponin T (cTNT), insulin receptor (IR) and muscle-specific chloride channel (C1C-1).

MD1 and MD2 are associated with a variety of serious pathologies including muscle abnormalities and weakness, and in the heart, conduction abnormalities.

SUMMARY OF THE INVENTION

The invention includes, in one aspect, an antisense compound for use in treating myotonic dystrophy DM1 or DM2. The compound is composed of an antisense oligonucleotide having 8-30 bases, with at least 8 contiguous bases being complementary to polyCUG or polyCCUG repeats, e.g., SEQ ID NOs: 49 and 50, respectively, in the 3'UTR region of dystrophia myotonica protein kinase (DMPK) mRNA in DM1 or DM2, respectively, and conjugated to the oligonucleotide, a cell-penetrating peptide having the sequence (RXRR(B/X)R)$_2$XB, where R is arginine; B is β-alanine; and each X is —C(O)—(CH$_2$)$_n$—NH—, where n is 4-6. The compound is effective to selectively block the sequestration of muscleblind-like 1 protein (MBNL1) and/or CUGBP in heart and quadricep muscle in a myotonic dystrophy animal model. Exemplary oligonucleotide sequences for MD1 include SEQ ID NOs: 44-47. An exemplary oligonucleotide sequence for MD2 includes SEQ ID NO: 48.

In one general embodiment, the cell penetrating peptide has the form (RXRRBR)$_2$XB (SEQ ID NO: 19) and X is —C(O)—(CH$_2$)$_6$—NH—, and the oligonucleotide is a phosphorodiamidate oligonucleotide (PMO) having between 12-30 bases, and at least 12 contiguous bases that are complementary to (i) the polyCUG repeats in the 3'UTR region of dystrophia myotonica protein kinase (DMPK) mRNA in DM1, or (ii) the polyCCUG repeats in the 3'UTR region of dystrophia myotonica protein kinase (DMPK) mRNA in DM2.

In another general embodiment, the cell penetrating peptide has the form (RXRRXR)$_2$XB (SEQ ID NO: 11) and X is —C(O)—(CH$_2$)$_6$—NH—, and the oligonucleotide is a phosphorodiamidate oligonucleotide (PMO) having between 12-30 bases, and at least 12 contiguous bases that are complementary to (i) the polyCUG repeats in the 3'UTR region of dystrophia myotonica protein kinase (DMPK) mRNA in DM1, or (ii) the polyCCUG repeats in the 3'UTR region of dystrophia myotonica protein kinase (DMPK) mRNA in DM2.

The compound may further include a homing peptide which is selective for muscle tissue, conjugated to the cell-penetrating peptide. Exemplary homing peptides have one of the sequences identified as SEQ ID NOs: 51-60, particularly SEQ ID NO:51. The compound preferably has the form cell-penetrating peptide-homing peptide-antisense oligomer.

In another aspect, the invention includes a method of targeting a systemically administered antisense oligonucleotide to heart tissue in a mammalian subject, where the oligonucleotide is directed against the polyCUG or polyCCUG repeats in the 3'UTR region of dystrophia myotonica protein kinase (DMPK) mRNA in DM1 or DM2, respectively. The method includes conjugating to the oligonucleotide, a cell-penetrating peptide having the sequence (RXRR(B/X)R)$_2$XB, where R is arginine; B is β-alanine; and each X is independently a neutral linear amino acid —C(O)—(CH$_2$)$_n$—NH—, where n is 4-6. In various general embodiments, preferred compounds formed by the conjugation are as given above.

In still another aspect, the invention includes a method of treating mytonic dystrophy DM1 or DM2 in a mammalian subject. The method includes, administering to the subject, an antisense compound comprising an antisense oligonucleotide having 8-30 bases, with at least 8 contiguous bases being complementary to the polyCUG or polyCCUG repeats in the 3'UTR region of dystrophia myotonica protein kinase (DMPK) mRNA in DM1 or DM2, respectively, and conjugated to the oligonucleotide, a cell-penetrating peptide having the sequence (RXRR(B/X)R)$_2$XB, where R is arginine; B is β-alanine; and each X is —C(O)—(CH$_2$)$_n$—NH—, where n is 4-6, and repeating said administering at least once every week to once every 3 months.

The cell penetrating peptide may have the form (RXRRBR)$_2$XB, or (RXRRXR)$_2$XB, where X is —C(O)—(CH$_2$)$_6$—NH—, and the oligonucleotide may be a phosphorodiamidate oligonucleotide (PMO) having between 12-30 bases, and at least 12 contiguous bases that are complementary to the polyCUG or polyCCUG repeats in the 3'UTR region of dystrophia myotonica protein kinase (DMPK) mRNA in DM1 or DM2, respectively.

The compound may be administered by intravenous or subcutaneous injection to the subject, at a dose between 1-5 mg/kg body weight antisense compound, and the administering step may be continued at regular intervals of every two weeks to three months. The subject may be monitored during the treatment for improvement in muscle performance, heart conduction properties, and/or for a reduction in serum creatine kinase.

In still other aspects, the invention includes methods and compounds for treating DMD and muscle atrophy, in accordance with methods and compositions detailed below.

These and other objects and features of the invention will become more fully apparent when the following detailed description of the invention is read in conjunction with the accompanying drawings.

BRIEF DESCRIPTION OF THE FIGURES

FIGS. 3A-D show the nuclear antisense activity of carrier peptide-PMO conjugates in the presence or absence of 10% serum (A-C) or in the presence of up to 60% serum (D).

The peptides 0, 2, 3a, 3b, 3c, 3d, 4a, 4b, 4c, 5 and 8, corresponding to the number of X residues in the peptide, are shown in Table 1 as SEQ ID NOs: 14, 20, 22, 19, 21, 25, 24, 23, 26, 11 and 3, respectively.

FIGS. 5A-F show the relative toxicity of carrier peptide-PMO conjugates, as measured by MTT assay.

FIGS. 6A-D show the relative toxicity of carrier peptide-PMO conjugates as measured by PI exclusion (A-C) and hemolysis (D) assays.

Figure 7A:
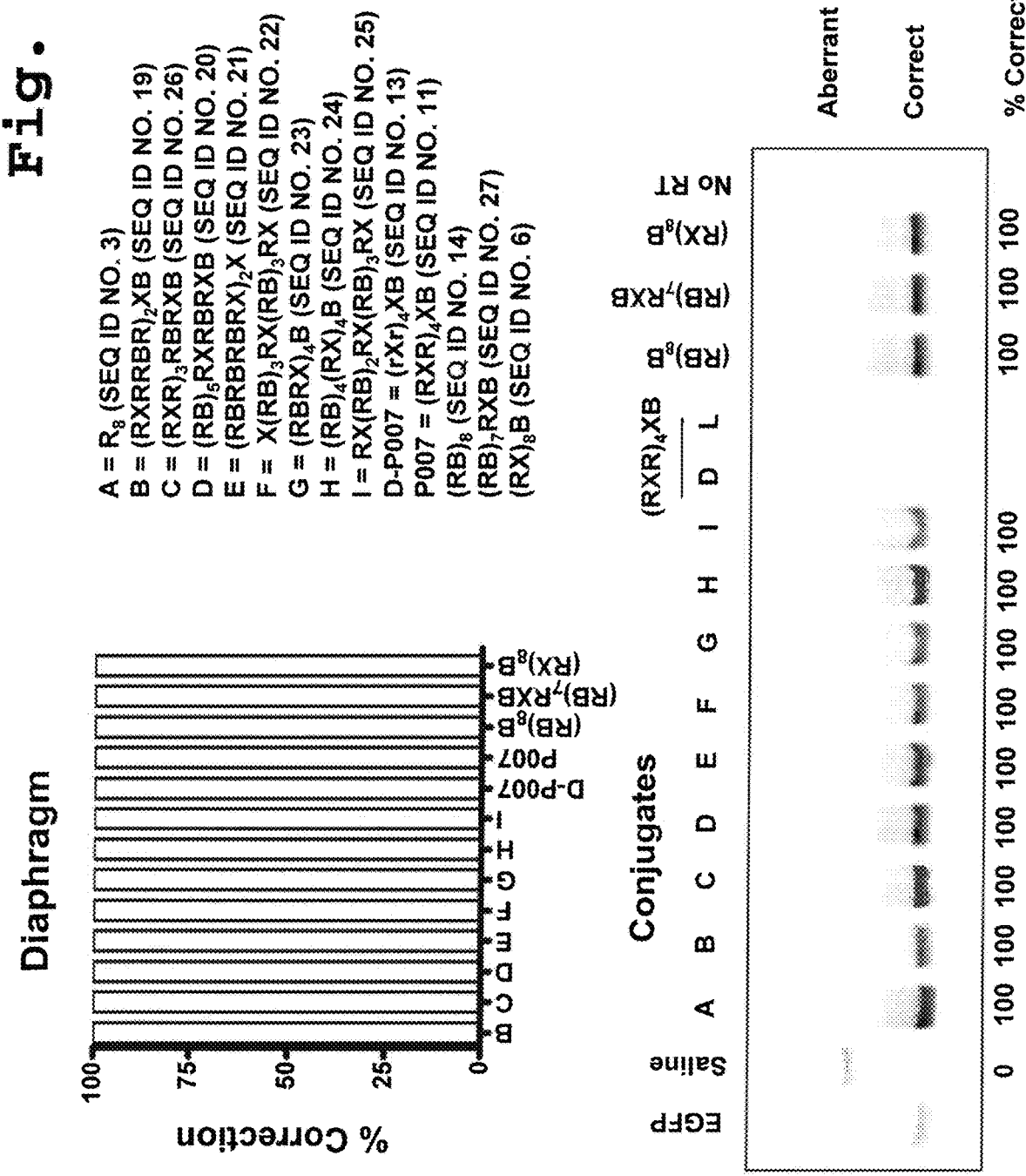
Figure 7B:
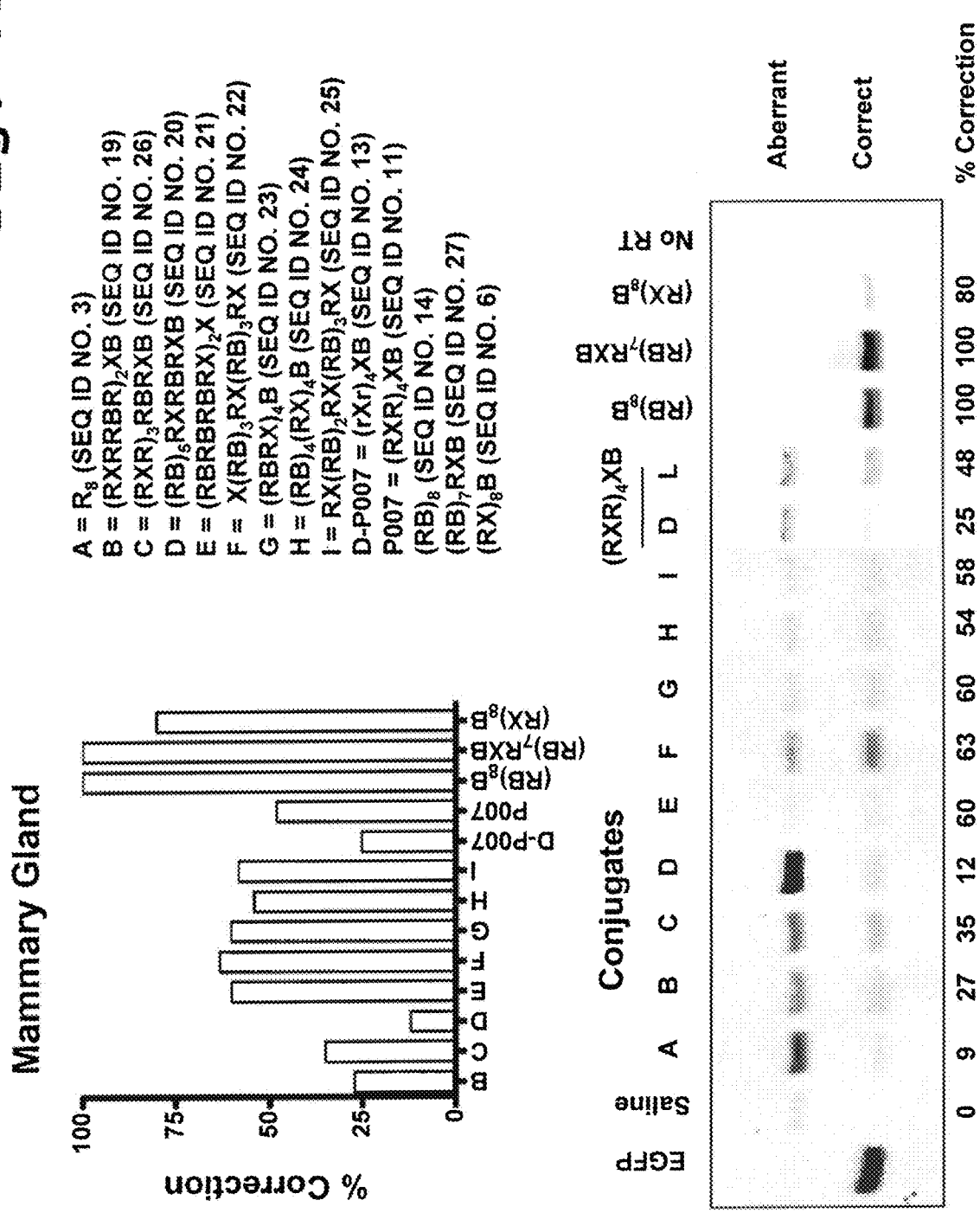
Figure 7D:
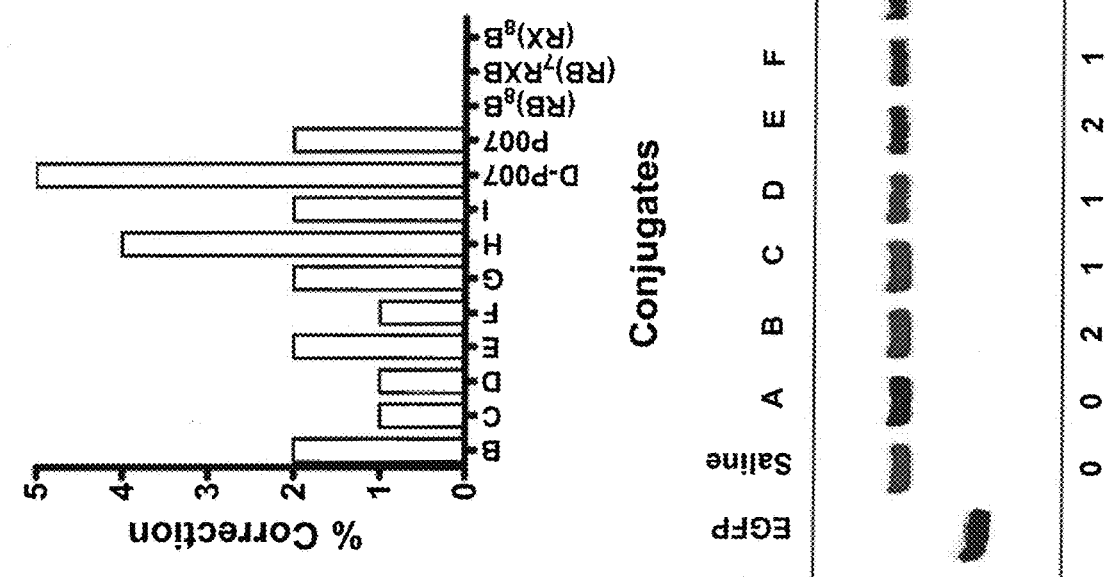
Figure 7E:
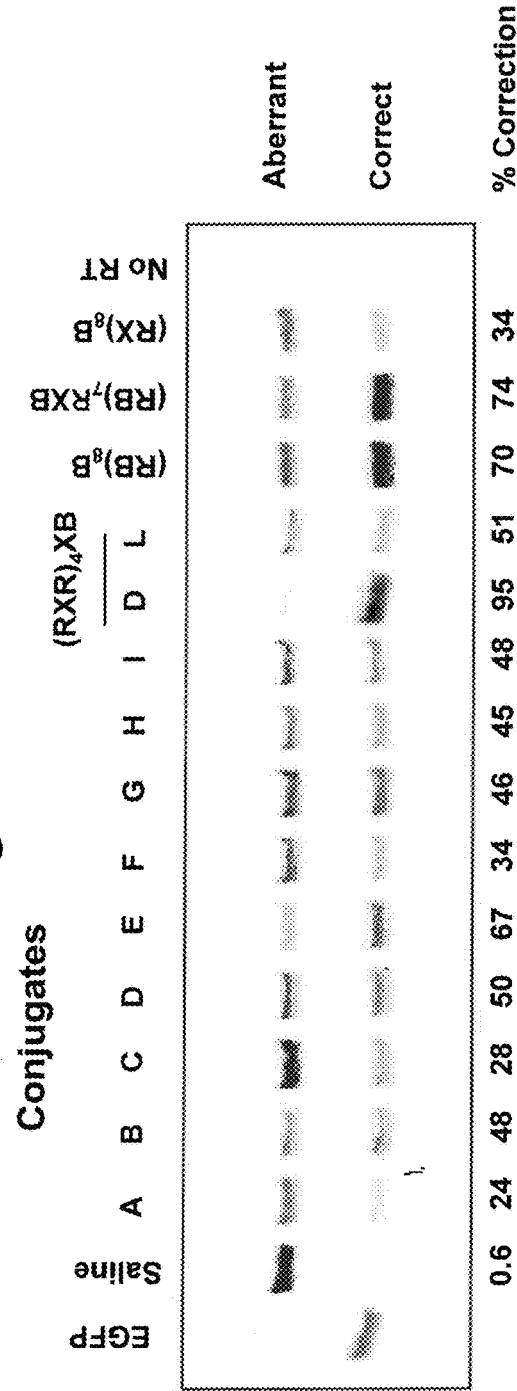
Figure 7H:
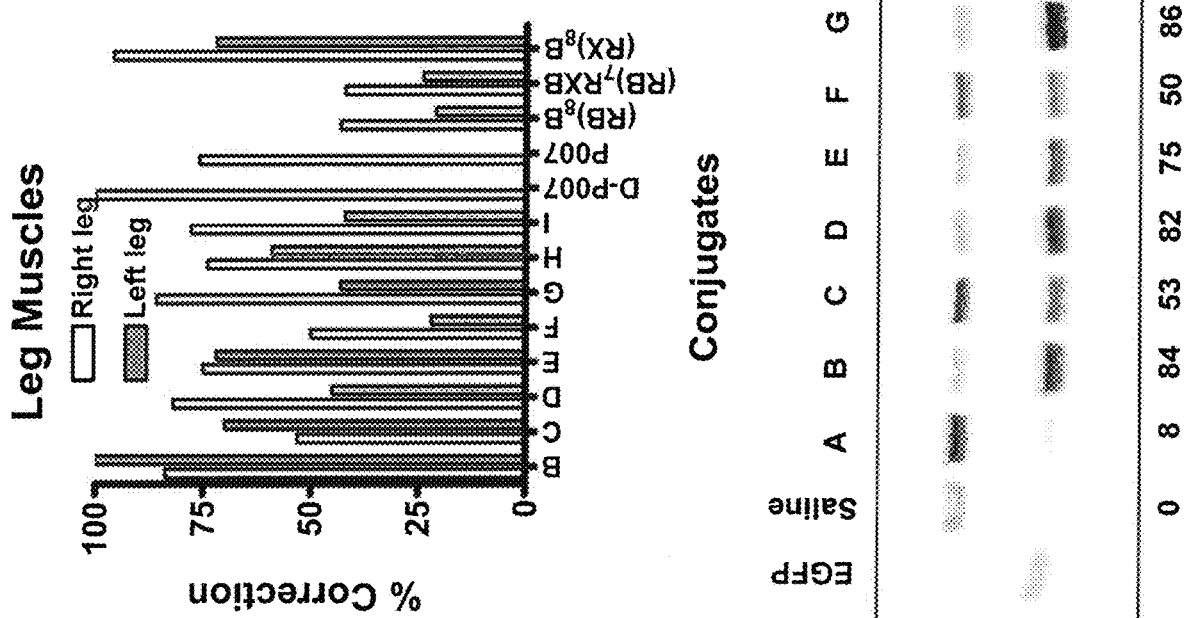

FIGS. 7A-P show the splice-correction activity in various organs from EGFP-654 transgenic mice treated with various EGFP-654-targeted cell penetrating peptide-PMO conjugates (SEQ ID NOs: 2, 6, 11, 13, 14 and 19-27) as measured in diaphragm (FIG. 7A), mammalian gland (FIG. 7B), ovary and prostate (FIG. 7C), brain (FIG. 7D), kidney (FIG. 7E), bone marrow (FIG. 7F), colon (FIG. 7G), muscle (FIG. 7H), skin (FIG. 7I), spleen (FIG. 7J), stomach (FIG. 7K), thymus (FIG. 7L), heart (FIG. 7M), lungs (FIG. 7N), small intestine (FIG. 7O), and liver (FIG. 7P).

Figure 8:
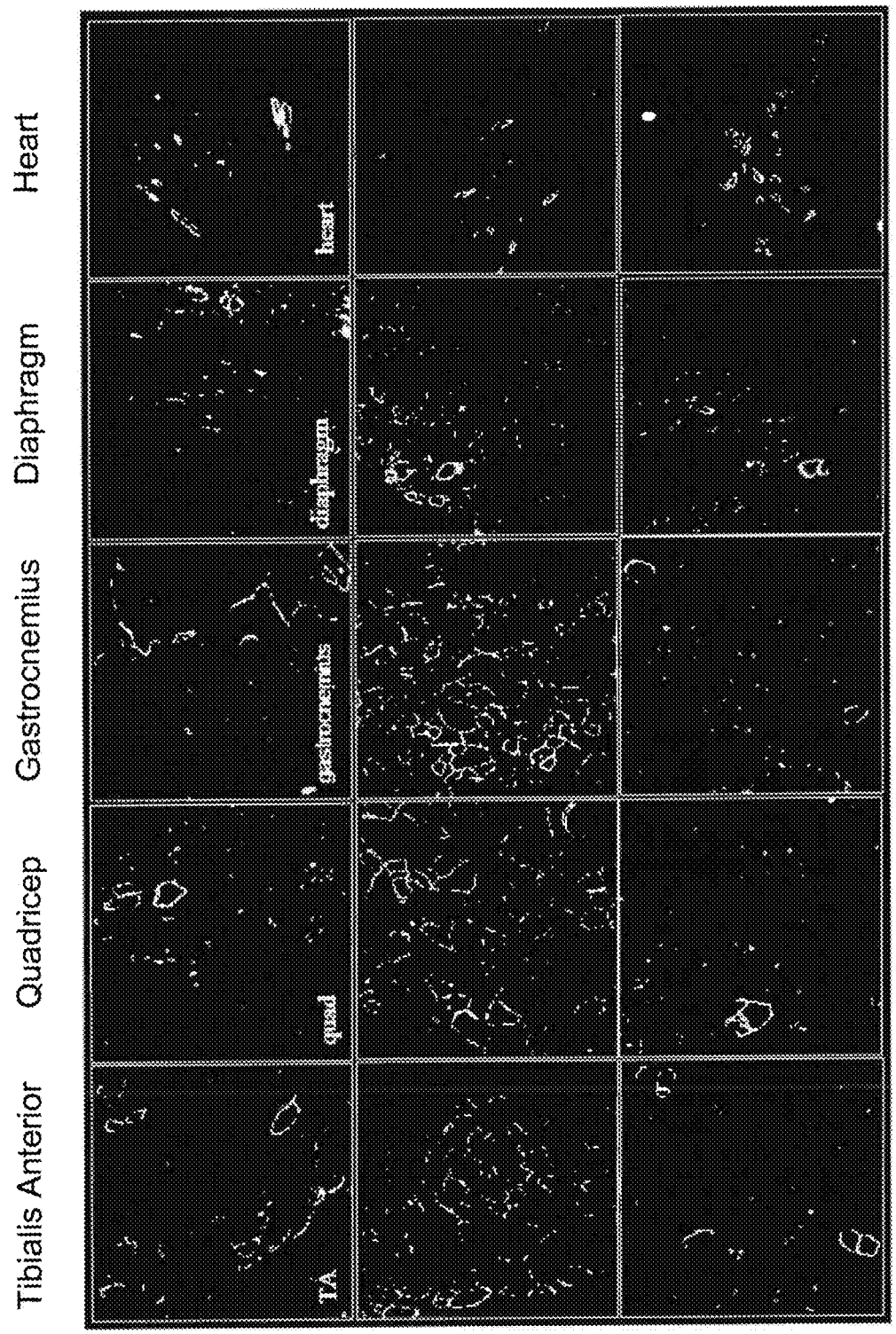

FIG. 8 shows the effect of conjugating an antisense oligomer with a muscle-specific cell penetrating peptide (SEQ ID NO: 19; referred to herein as peptide "B" and also designated CP06062) in combination with a muscle specific homing peptide (MSP), as measured by restoration of full-length dystrophin in the MDX mouse model.

Figure 9:
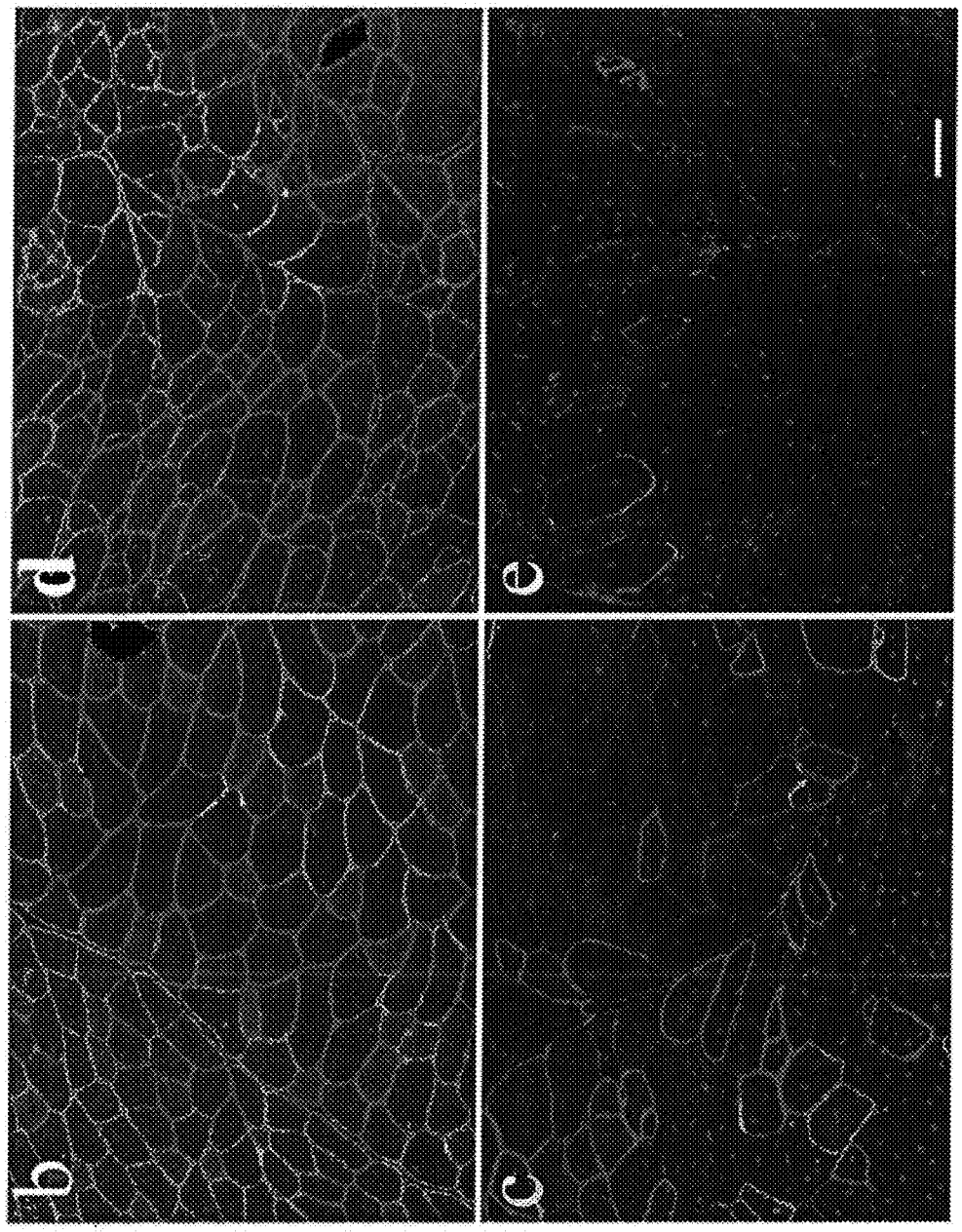

FIG. 9 shows a comparison of dystrophin induction in TA muscles with M23d PMO (SEQ ID NO: 37) and M23d-CP06062 PPMO (SEQ ID NO: 37 conjugated to SEQ ID NO: 19) by intramuscular injections. The muscles of adult MDX mice were injected with 2 micrograms of each antisense composition and examined by immunohistochemistry with rabbit polyclonal antibody P7 against dystrophin 2 weeks after the injection. Muscle from normal C57BL mouse (b) and mdx mouse injected with 2 micrograms M23d PMO (c), 2 micrograms M23d-CP06062 PPMO (d), and 2 micrograms scrambled PPMO (e). Eighty-five percent of the muscle fibers were induced to express dystrophin after M23d-CP06062 PPMO treatment (d), compared with only 14% of fibers after M23d PMO treatment (c). Only a few revertant fibers were detected in the muscle treated with the scrambled PPMO (e). Nuclear staining with DAPI. (Scale bar, 50 μm.)

Figure 10:
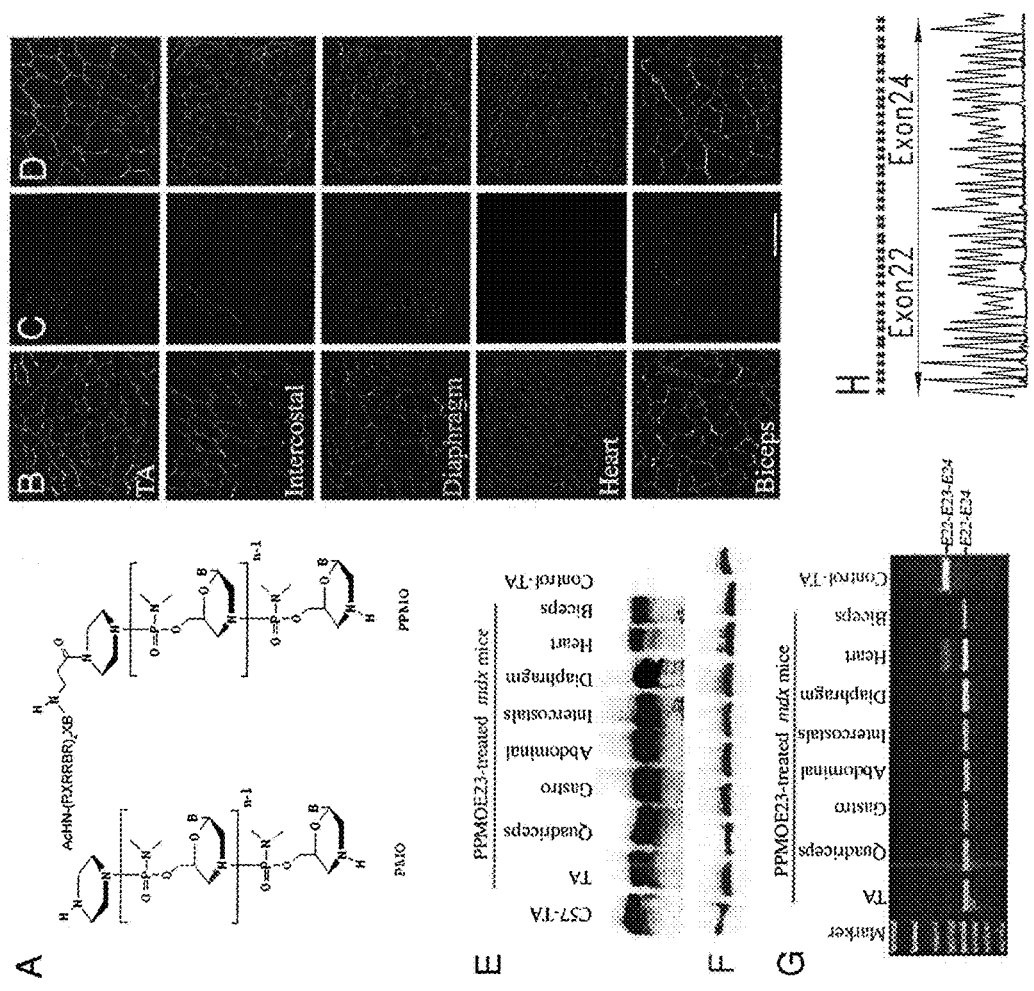

FIG. 10 shows the structures of PMO and PPMO (A) and restoration of dystrophin in muscles of mdx mice (aged 4-5 weeks) after a single i.v. injection of 30 mg/kg of M23d-CP06062 PPMO. The muscles were examined 2 weeks after injection. (B-D) Detection of dystrophin by immunohistochemistry with rabbit polyclonal antibody P7 against dystrophin. Nuclear staining with DAPI. (Scale bar, 100 μm.) Muscles from normal C57BL mice (B), scrambled PPMO-treated mdx mice (C), and M23d-CP06062 PPMO-treated mdx mice (D). Dystrophin was homogenously expressed in all muscle fibers from the M23d-CP06062 PPMO-treated mice. (E) Western blot demonstrated dystrophin in all muscles detected with the NCL-DYS1 monoclonal antibody. C57-TA, tibialis anterior muscle from normal C57BL; Gastro, gastrocnemius; Control-TA, muscle from the scrambled PPMO-treated mdx mouse. (F) Western blot for α-actin as protein loading control. (G) Detection of exon 23-skipped dystrophin mRNA by RT-PCR. The upper 1,093-bp bands (indicated by E22-E23-E24) correspond to the normal mRNA, and the lower 880-bp bands (indicated by E22-E24) correspond to the mRNA with exon 23 skipped. Sequencing of the 880-bp RT-PCR product confirmed the skipping of the exon 23 (H).

Figure 11:
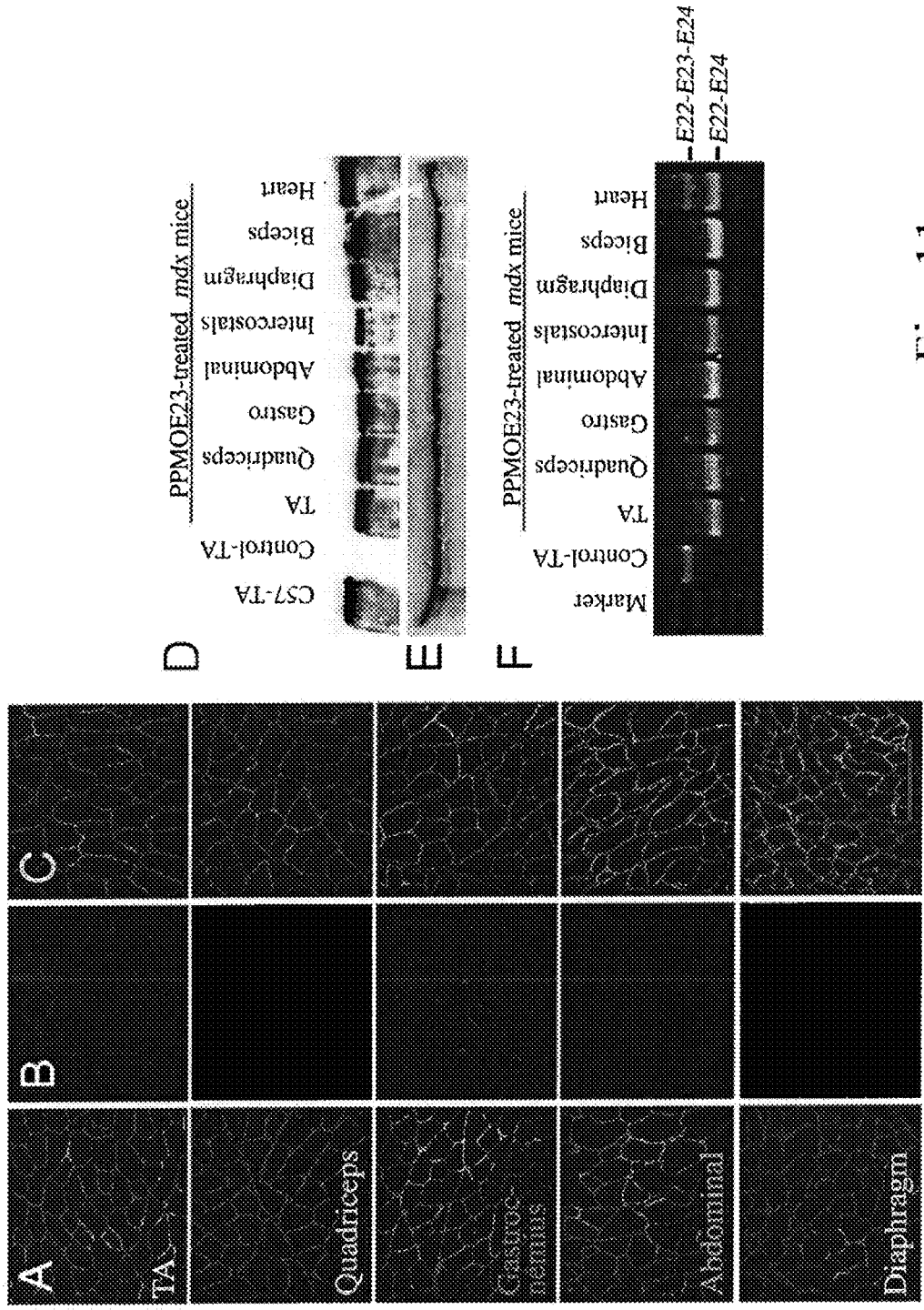

FIG. 11 shows the restoration of dystrophin in bodywide muscles of mdx mice (age 4-5 weeks) after six i.v. injections of 30 mg/kg of M23d-CP06062 PPMO at biweekly intervals. Muscles were examined 2 weeks after the last injection. Muscles from normal C57BL mice (A), scrambled PPMO-treated mdx mice (B), and M23d-CP06062 PPMO-treated mdx mice (C). Nuclear staining with DAPI. Dystrophin was expressed homogenously in all muscle fibers from the M23d-CP06062 PPMO-treated mdx mice. (Scale bar, 100 μm) (D) Western blot demonstrated near-normal levels of dystrophin in all muscles detected with the NCL-DYS1 monoclonal antibody. C57-TA, TA muscle from normal C57BL mouse; Control-TA, TA muscle from scrambled PPMO-treated mdx mouse; Gastro, gastrocnemius. (E) Western blot for α-actin as protein loading control. (F) Detection of exon 23 skipping by RT-PCR. Total RNA of 100 ng from each sample was used for amplification of dystrophin mRNA from exon 20 to exon 26. Control-TA, TA muscle from scrambled PPMO-treated mdx mouse. The upper 1,093-bp bands (indicated by E22-E23-E24) correspond to the normal dystrophin mRNA, and the lower 880-bp bands (indicated by E22-E24) correspond to the mRNA with exon 23 skipped.

Figure 12:
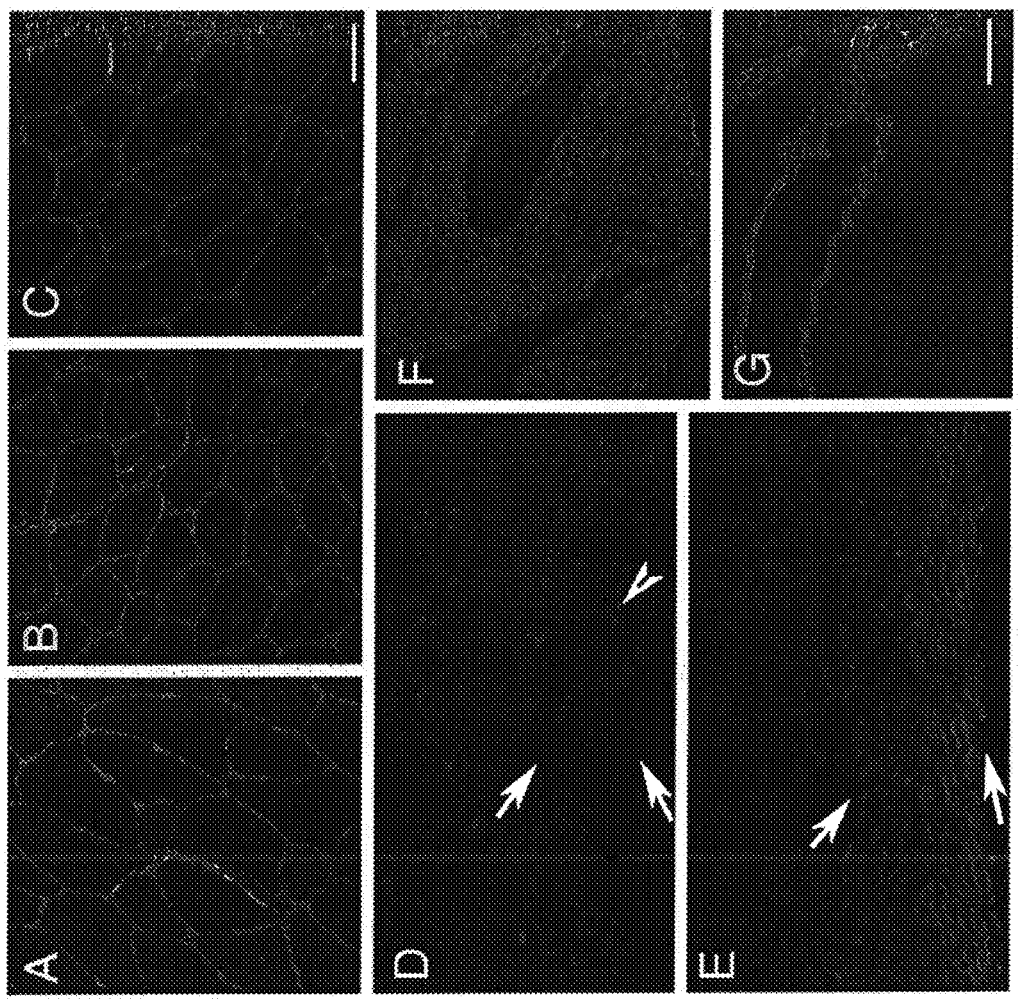

FIG. 12 shows the restoration of dystrophin in skeletal and smooth muscles after six cycles of 30-mg/kg M23d-CP06062 PPMO injection. Back thoracic and lumbar muscle (A), digital muscle (B), flexor muscle (C). Smooth muscles (layers between the two arrows) in small intestine of untreated mdx mouse (D) and M23d-CP06062 PPMO-treated mdx mouse (E). Arrowhead indicates a revertant fiber. Dystrophin expression in the smooth muscle of aorta and vena cava (F) and arteries and other vessels in the lung (G). Dystrophin was detected by immunostaining with rabbit polyclonal antibody P7. Nuclear staining with DAPI. (Scale bars: A-E, 50 μm; F and G, 120 μm.)

FIGS. 13A-13D show restoration of muscle and cardiac dystrophin expression in mdx mice. Restoration of dystrophin expression following single 25 mg/kg intravenous injections of the P007-M23d PPMO (SEQ ID NO: 37 conjugated to SEQ ID NO: 11) conjugate in adult mdx mice. (A) Immunostaining of muscle tissue cross-sections to detect dystrophin protein expression and localization in C57BL6 normal control mice (top panel), untreated mdx mice (middle panel) and P007-M23d PPMO-treated mdx mice (lower panel), showing near normal levels of dystrophin expression in the treated mice. Muscle tissues analysed were from tibialis anterior (TA), gastrocnemius, quadriceps, biceps, abdominal wall, diaphragm and heart muscles (scale bar=200 microns). (B) RT-PCR to detect exon skipping efficiency at the RNA level demonstrated almost complete exon 23 skipping in the peripheral skeletal muscles indicated and 50% exon skipping in heart in treated mdx mice. This is shown by shorter exon-skipped bands (indicated by the boxed numbered 22-24—for exon 23 skipping). Truncated transcripts deleted for both exons 22 and 23 were also seen as indicated by the box 21-24. (C) Western blot for dystrophin expression in peripheral skeletal muscles showed 100% dystrophin restoration in all skeletal muscles except the diaphragm and with P007-M23d PPMO conjugate treatment compared with levels found in normal C57BL6 mice. Equal loading of 10 µg protein is shown for each sample with -actinin expression detected as a loading control. (D) Western blot to detect dystrophin expression in heart tissue from normal C57BL6 heart (20, 10 and 5% of normal levels shown), untreated mdx heart and P007-M23d PPMO treated heart. Data shows dystrophin protein restoration to 15% of normal levels in P007-M23d PPMO treated mdx heart tissue.

DETAILED DESCRIPTION

I. Definitions

The terms below, as used herein, have the following meanings, unless indicated otherwise:

The terms "cell penetrating peptide" or "CPP" are used interchangeably and refer to cationic cell penetrating peptides, also called transport peptides, carrier peptides, or peptide transduction domains. The peptides, as shown herein, have the capability of inducing cell penetration within 100% of cells of a given cell culture population and allow macromolecular translocation within multiple tissues in vivo upon systemic administration.

The terms "antisense oligomer" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits are based on ribose or another pentose sugar or, in a preferred embodiment, a morpholino group (see description of morpholino oligomers below). The oligomer may have exact or near sequence complementarity to the target sequence; variations in sequence near the termini of an oligomer are generally preferable to variations in the interior.

In one aspect of the invention, for the treatment of MD1 or MD2, the antisense oligonucleotide is complementary to at least 8, typically 9-12 or more, e.g., 15-30 contiguous bases in polyCUG repeats or polyCCUG repeats within the 3' UTR regions of the transcript for dystrophia myotonica protein kinase (DMPK) in muscle cells, and is designed to bind by hybridization to these repeats, blocking binding of splice-associated proteins, such as one or more muscleblind family proteins, e.g., MBNL1, or CUGBP to the transcript. The oligonucleotide may be said to be "directed to" or "targeted against" 3'UTR polyCUG or polyCCUG repeats with which it hybridizes. The target sequence may include a polyCUG or polyCCUG region of at least 8 contiguous bases, preferably at least 9-25, and up to 40 bases or more. SEQ ID NOs: 49, 50 define polyCUG and polyCCUG repeat sequences of 39 and 40 bases, respectively.

In another aspect, for the treatment of DMD, the antisense oligonucleotide is complementary to at least 8, typically 9-12 or more e.g., 15-30 contiguous bases in a splice-junction site or exon recognition sequence of a dystrophin pre-MRNA, where binding of the oligonucleotide to the target pre-mRNA sequence is effective to promote skipping of one or more exons in a mutated dystrophin gene, with the result that the normal reading frame of the processed mRNA is restored. Exemplary targeting sequences includes one from SEQ ID NOs: 28-38.

In still another aspect, for treatment of muscle atrophy, the antisense oligonucleotide is complementary to at least 8, typically 9-12 or more, e.g., 15-30 bases, in an AUG region of myostatin mRNA or a splice-junction site of a myostatin pre-mRNA, effective to inhibit expression of a functional myostatin protein in muscle cells. Exemplary targeting sequences includes one from SEQ ID NOs: 39-43.

Figure 1A:
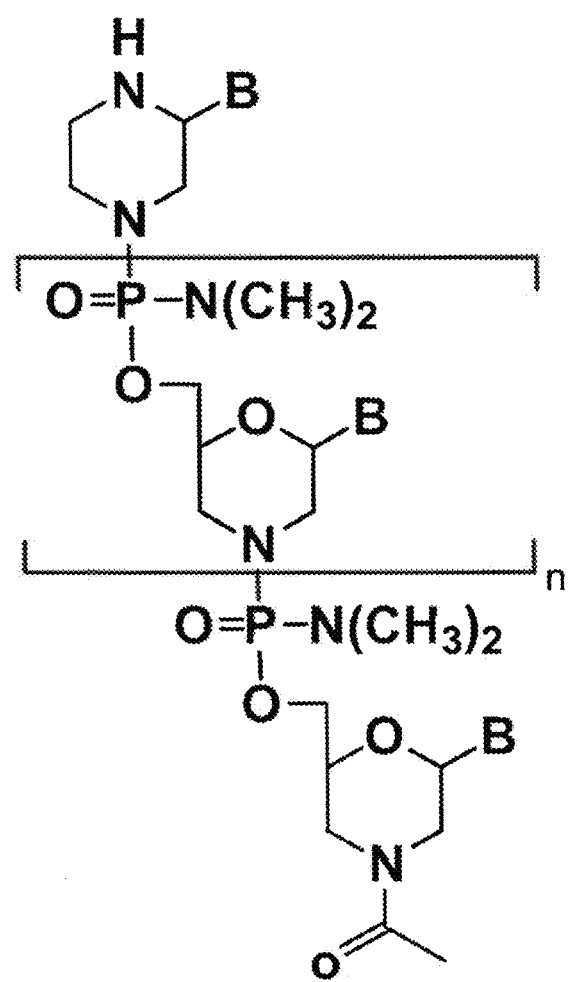
FIGS. 1A-C show exemplary structures of a phosphorodiamidate-linked morpholino oligomer (PMO), a peptide-conjugated PMO (PPMO), and a peptide-conjugated PMO having cationic intersubunit linkages (PPMO+), respectively. (Though multiple cationic linkage types are illustrated in FIG. 1C, a PMO+ or PPMO+ oligomer will typically include just one type of cationic linkage.)

The terms "morpholino oligomer" or "PMO" (phosphoramidate- or phosphorodiamidate morpholino oligomer) refer to an oligonucleotide composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide. See, for example, the structure in FIG. 1A, which shows a preferred phosphorodiamidate linkage type. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Pubn. No. WO 2008036127 (cationic linkages), all of which are incorporated herein by reference.

An "amino acid subunit" or "amino acid residue" can refer to an α-amino acid residue (—CO—CHR—NH—) or a β- or other amino acid residue (e.g. —CO—$(CH_2)_n$CHR—NH—), where R is a side chain (which may include hydrogen) and n is 1 to 6, preferably 1 to 4.

The term "naturally occurring amino acid" refers to an amino acid present in proteins found in nature. The term "non-natural amino acids" refers to those amino acids not present in proteins found in nature, examples include beta-alanine (β-Ala), 6-aminohexanoic acid (Ahx) and 6-aminopentanoic acid.

A "marker compound" refers to a detectable compound attached to a transport peptide for evaluation of transport of the resulting conjugate into a cell. The compound may be visually or spectrophotometrically detected, e.g. a fluorescent compound or fluorescently labeled compound, which may include a fluorescently labeled oligomer. Preferably, the marker compound is a labeled or unlabeled antisense oligomer. In this case, detection of transport involves detection of a product resulting from modulation of splicing and/or transcription of a nucleic acid by an antisense oligomeric compound. Exemplary methods, such as a splice correction assay or exon skipping assay, are described in Materials and Methods below.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

An "antisense compound" or "compound" or "conjugate compound" refers to a compound formed by conjugating the $(RXRR(X/B)R)_2XB$ cell-penetrating peptides to an oligonucleotide targeted against a muscle-protein gene, e.g., a region of polyCUG or polyCCUG repeats.

"Systemic administration" of a compound refers to administration, such as intravenous (iv) subcutaneous (subQ), intramuscular (IM), and intraperitoneal (IP) that delivers the compound directly into the bloodstream.

A systemically administered antisense oligonucleotide is targeted to heart muscle tissue by conjugation to the CPP $(RXRRBR)_2XB$, if the compound, when administered systemically to a MD1 or MD2 subject in accordance with the method herein, produces a measurable improvement in heart muscle performance and/or improvement in conduction properties of the heart, as measured by known methods.

II. Structural Features of Transport Peptides

The two cell-penetrating peptides employed in the invention are in a class of a transport peptide having 8 to 30 amino acid residues in length and consisting of subsequences selected from the group consisting of RXR, RX, RB, and RBR; where R is arginine (which may include D-arginine, represented in the sequences herein by r), B is β-alanine, and each X is independently $—C(O)—(CHR^1)_n—NH—$, where n is 4-6 and each $R^1$ is independently H or methyl, such that at most two $R^1$'s are methyl. Preferably, each $R^1$ is hydrogen. The two peptides have the generic formula $(RXRR(B/X)R)_2XB$, where R is arginine; B is β-alanine; and each X is $—C(O)—(CH_2)_n—NH—$, where n is 4-6, preferably 6, and include both $(RXRRBR)_2XB$ (SEQ ID NO: 19) and $(RXRRXR)_2XB$ (SEQ ID NO: 11) and where R is arginine; B is β-alanine; and each X is $—C(O)—(CH_2)_n—NH—$, where n is 4-6. As discussed in Section V below, these two peptides have been discovered to selectively target an oligonucleotide, including a PMO, to muscle tissue, including, importantly, heart muscle tissue.

Table 1 below shows the sequences of various transport peptides in this class that were evaluated, in conjugation with suitable antisense oligonucleotides, for their ability to selectively target various tissues, including heart and skeletal muscle. The peptides were evaluated for cellular uptake (Section III), as determined by flow cytometry; for antisense activity (Section IV), as determined by a splice correction assay (Kang, Cho et al. 1998); and for cellular toxicity, as determined by MTT cell viability, propidium iodide membrane integrity and hemolysis assays, and microscopic imaging, and their uptake and functional activity in muscle tissue relative to a variety of non-muscle tissue were compared (Section V). As will be seen in Section IV, the $(RXRRXR)_2XB$ (SEQ ID NO: 11) peptide was among the most active in antisense activity, as determined by the splice correction assay (the $(RXRRBR)_2XB$ (SEQ ID NO: 19) peptide was not tested in this assay), both in the presence and absence of added serum. As will be seen in Section V, both $(RXRR(B/X)R)_2XB$ (SEQ ID NO: 68) peptides were effective in selectively targeting oligonucleotides to heart and skeletal tissue, while showing relatively low-level targeting to a variety of other tissues, including mammary gland tissue, ovary/prostate (particularly $(RXRRXR)_2XB$) (SEQ ID NO: 11), and brain.

TABLE 1

Cell-Penetrating Peptides

| Name (Designation) | Sequence | SEQ ID NO.[a] |
|---|---|---|
| Oligoarginines | | |
| $R_8$-XB (A; 8) | RRRRRRRR-XB | 3 |
| $r_8$-XB | rrrrrrrr-XB | 4 |
| $R_9$-XB | RRRRRRRRR-XB | 5 |
| Oligo (RX), (RXR), and (RB) series, including D-arginine | | |
| $(RX)_8$-B | RXRXRXRXRXRXRXRX-B | 6 |
| $(rX)_8$-B | rXrXrXrXrXrXrXrX-B | 7 |
| $(RX)_7$-B | RXRXRXRXRXRXRX-B | 8 |
| $(RX)_5$-B | RXRXRXRXRX-B | 9 |
| $(RX)_3$-B | RXRXRX-B | 10 |
| $(RXR)_4$-XB (P007; 5) | RXRRXRRXRRXR-XB | 11 |
| $(rXR)_4$-XB | rXRrXRrXRrXR-XB | 12 |
| $(rXr)_4$-XB (D-P007) | rXrrXrrXrrXr-XB | 13 |
| $(RB)_8$-B (O) | RBRBRBRBRBRBRBRB-B | 14 |
| $(rB)_8$-B | rBrBrBrBrBrBrBrB-B | 15 |
| $(RB)_7$-B | RBRBRBRBRBRBRB-B | 16 |
| $(RB)_5$-B | RBRBRBRBRB-B | 17 |
| $(RB)_3$-B | RBRBRB-B | 18 |
| (RX), (RXR), (RB), and (RBR) mixed series | | |
| $(RXRRBR)_2$-XB (B; 3b; CP06062) | RXRRBRRXRRBR-XB | 19 |
| $(RXR)_3RBR$-XB (C; 4c) | RXRRXRRXRRBR-XB | 26 |
| $(RB)_5RXBR$-XB (D; 2) | RBRBRBRBRBRXRBR-XB | 20 |
| $(RBRBRBRX)_2$-X (E; 3c) | RBRBRBRXRBRBRBRX-X | 21 |
| $X(RB)_3RX(RB)_3R$-X (F; 3a) | XRBRBRBRXRBRBRBR-X | 22 |
| $(RBRX)_4$-B (G; 4b) | RBRXRBRXRBRXRBRX-B | 23 |
| $(RB)_4(RX)_4$-B (H; 4a) | RBRBRBRBRXRXRXRX-B | 24 |
| $RX(RB)_2RX(RB)_3R$-X (I; 3d) | RXRBRBRXRBRBRBR-X | 25 |
| $(RB)_7RX$-B | RBRBRBRBRBRBRBRX-B | 27 |

[a]Sequences assigned to SEQ ID NOs do not include the linkage portion (X, B, or XB).

III. Cellular Uptake of Peptide-Oligomer Conjugates

Cellular uptake of peptide-PMO conjugates, where the PMO was a 3'-carboxy fluorescein-tagged PMO (PMOF), was investigated using flow cytometry. A treatment concentration of 2 µM was used because none of the conjugates caused any detectable cytotoxicity at this concentration, as demonstrated by MTT and PI uptake assays (below). After incubation with conjugate, cells were treated with trypsin (Richard, Melikov et al. 2003) to remove membrane-bound conjugate. To determine the effect of serum on cellular uptake of the various conjugates, uptake evaluation assays were carried out in medium containing various concentrations of serum.

Figure 2:
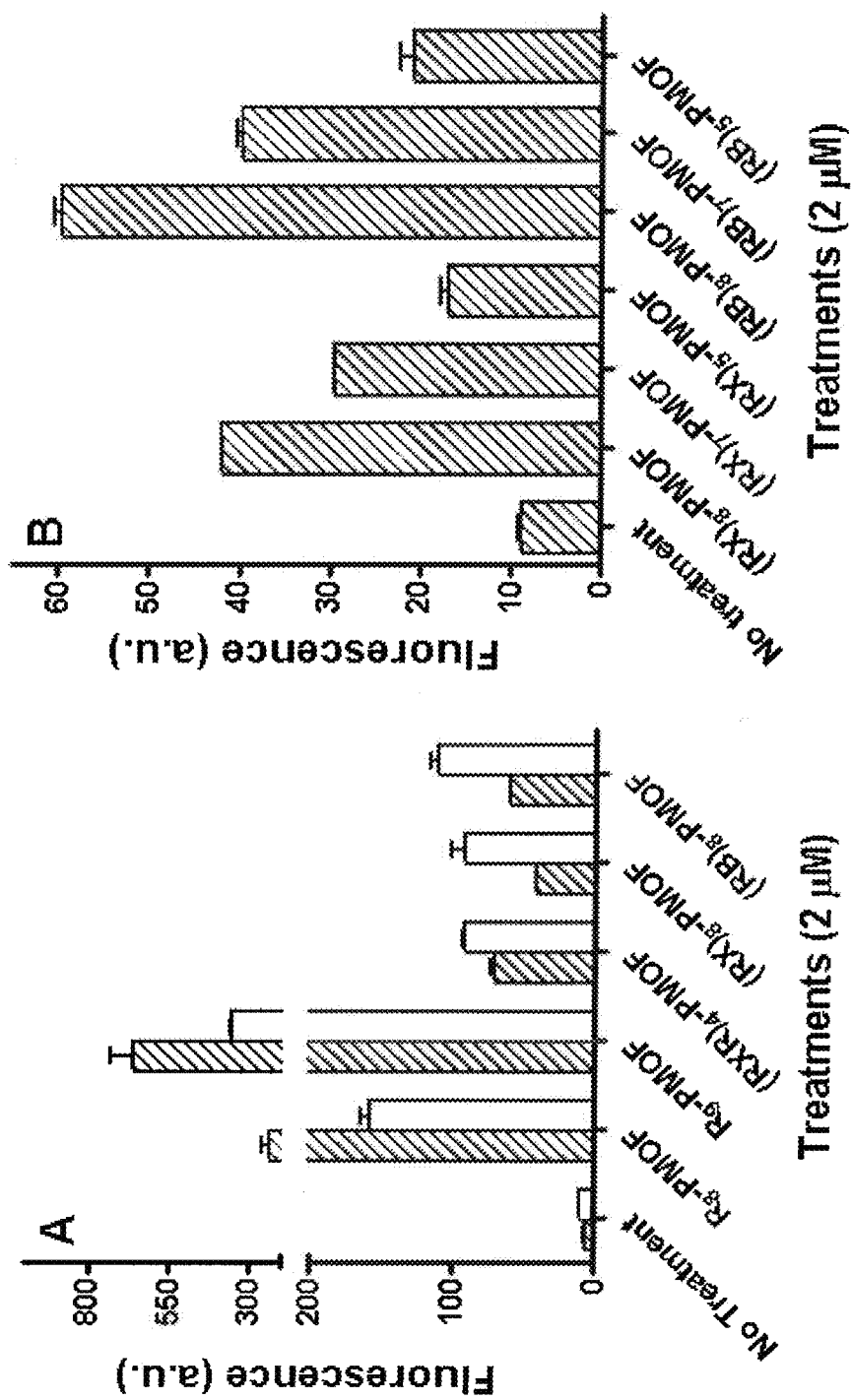
FIGS. 2A-B show the cellular uptake of conjugates of various cell penetrating peptides (CPPs) with carboxyfluorescein-labeled morpholino oligomers (PMOF) in pLuc705 cells.

As shown in FIGS. 2A-B, cellular uptake of the conjugates increased with the number of arginine residues in the transport peptide and generally decreased with X and/or B residue insertion. For example, the oligoarginine $R_9$-PMOF conjugate had a mean fluorescence (MF) value of 662, nearly 3-fold higher than that of $R_8$-PMOF. Insertion of an X or B residue in the $R_8$ sequence reduced uptake of the respective conjugates, as shown by MF values for conjugates of $R_8$ (234), $(RX)_8$ (42), $(RXR)_4$ (70), and $(RB)_8$ (60) (FIG. 2A). The number of RX or RB repeats also affected cellular uptake, with conjugates having fewer RX or RB repeats generating lower MF values (FIG. 2B).

While the addition of 10% serum to the medium caused a decrease in the uptake of the oligoarginine $R_8$- or $R_9$-PMOF conjugates, it increased uptake of conjugates containing RX, RB or RXR motifs (FIGS. 2A and 2C). For example, the presence of serum reduced the MF of $R_9$- and $R_8$-PMOF from 662 and 234 to 354 and 158, respectively, but it increased the MF of $(RX)_8$-, $(RXR)_4$-, and $(RB)_8$-PMOF from 41, 70 and 60 to 92, 92, and 111, respectively. These differences were statically significant (FIG. 2A). However, higher serum concentrations (30% and 60%) decreased the uptake of both $(RXR)_4$-PMOF and oligoarginine-PMOF.

Arginine stereochemistry (D vs. L) had little effect on uptake of the peptide-PMOF conjugates. Uptake as shown by MF values of $R_8$-, $(RB)_8$- and $(RX)_8$-PMOF conjugates was not significantly different from their respective D-isomer conjugates, $r_8$-, $(rB)_8$- and $(rX)_8$-PMOF (data not shown).

IV. In Vitro Nuclear Antisense Activity

The effectiveness of the subject peptides in transporting an attached molecule to the nucleus of a cell was determined in a splicing correction assay (Kang, Cho et al. 1998), where the attached compound is a steric-blocking antisense oligomer (AO), in this case a PMO. This assay utilizes the ability of the oligomer to block a splice site created by a mutation in order to restore normal splicing. Specifically, the luciferase coding sequence is interrupted by the human β-globin thalassemic intron 2, which carries a mutated splice site at nucleotide 705. HeLa cells were stably transfected with the resulting plasmid and designated pLuc705 cells. In the pLuc705 system, the oligomer must be present in the cell nucleus for splicing correction to occur. Advantages of this system include the positive readout and high signal-to-noise ratio. With this system, the relative efficiencies of various transport peptides to deliver an AO with sequence appropriate for splice-correction to cell nuclei can be easily compared.

As described below, the subject carrier peptide-PMO conjugates display higher activity in cell nuclei, and are less affected by serum and more stable in blood, than oligoarginine-PMO conjugates.

Oligoarginine, RX, RXR and RB panels (see Table 1). The peptide-PMO conjugates with the highest nuclear antisense activities in this series were found to be $(RXR)_4$- and $(RX)_8$-PMO (where, as noted above, R is arginine, and X in these peptides is 6-aminohexanoic acid). FIGS. 3A and 3B show luciferase activity normalized to protein of cells treated with various conjugates at 1 µM and 5 µM for 24 hr. At both concentrations, $(RX)_8$- and $(RXR)_4$-PMO were more effective than the other conjugates tested, with the difference more prominent in serum-containing medium at 1 µM than at 5 µM. Cells treated with 1 µM of either conjugate exhibited luciferase activity at a level 10-15 fold over background, while the remaining conjugates yielded about a 2-4 fold increase over background (FIG. 3A). At 5 µM, all conjugates generated higher luciferase activity than at 1 µM, with $(RX)_8$-PMO and $(RXR)_4$-PMO again the most effective, followed by $(RB)_8$-PMO (FIG. 3B).

FIG. 3C shows that, at 10 µM, the activity of RX or RB conjugates decreased as the number of RX or RB repeats (i.e. length) in the transport peptide decreased. The peptides with three or five RX or RB repeats generated much lower luciferase activity than those with seven or eight repeats.

Number and position of X residues. In order to investigate the effect of the number and position of X residues on the activity of conjugates, eleven peptide-PMO conjugates, where the peptide component contained 0, 2, 3, 4, 5, or 8 X (6-aminohexanoic acid) residues, were compared (SEQ ID NOs: 14, 20, 22, 19, 21, 25, 24, 23, 26, 11 and 3 as shown in Table 1). The data (shown as luciferase activity in the assay described above) is presented in FIG. 4.

Generally, peptides containing a higher number of X residues had higher transport activities. At 2 µM, $(RX)_8$-PMO (eight X residues) had the highest activity, followed by $(RXR)_4$-PMO (five X residues), and the conjugates with fewer X residues had lower activities.

At 5 µM, three conjugates containing three (I; SEQ ID NO: 25), four (C; SEQ ID NO: 26) and eight $((RX)_8)$ 6-aminohexanoic acid residues had the highest activities, suggesting that the position of X residues affects activity.

Serum effect on activity. The effect of serum on the antisense activity of the conjugates was dependent on the peptide sequences, as shown in FIGS. 3A-3D. Addition of 10% serum to the medium decreased the activity of oligoarginine-PMO conjugates ($R_8$-PMO and $R_9$-PMO) but increased activity of conjugates containing RXR, RX and RB repeats. The addition of 10% serum nearly doubled the luciferase activity of $(RXR)_4$-, $(RX)_8$- and $(RB)_8$-PMO at 5 µM (FIG. 3B). This effect was further investigated for $(RXR)_4$-PMO up to 60% serum (see FIG. 3D). While the activity almost doubled as the serum concentration increased from 0% to 10%, it gradually decreased as the serum concentration increased to 60%, at which activity was similar to that in 0% serum (which was still significantly above background). This "up and down" profile was also observed with the 1 µM $(RXR)_4$-PMO treatment. Unlike $(RXR)_4$-PMO, the luciferase activity of $R_8$-PMO or $R_9$-PMO consistently decreased as the serum concentration increased, with an approximately 30% reduction in 10% serum and no activity in 60% serum (FIG. 3D). $R_8$-PMO or $R_9$-PMO did not display any detectable activity at 1 µM, regardless of the serum concentration (FIG. 3A).

V. Tissue Selectivity for In Vivo Nuclear Antisense Activity

Various transport peptides were conjugated to PMO, and the resulting conjugates (P-PMOs) were tested for their ability to transport the PMO into various tissues, in accordance with the invention, as described further in Materials and Methods, below. Briefly, conjugates were administered for four consecutive days. The in vivo uptake of the P-PMOs was determined by targeting the PMO (SEQ ID NO: 1) to an aberrantly spliced mutated intron in the EGFP-654 gene in an EGFP-654 transgenic mouse model (Sazani, Gemignani et al. 2002). In this model, cellular uptake of the EGFP-654 targeted P-PMOs can be evaluated by RT-PCR detection of restored EGFP-654 mRNA splice product and functionally restored EGFP in tissues harvested after IP administration of P-PMO.

As shown in FIGS. 7A-P, P-PMOs containing various transport peptides displayed selective uptake by specific tissues. In particular, a conjugate containing the transport peptide (RXRRBR)$_2$-XB (SEQ ID NO: 19) displayed selective uptake into heart, and skeletal muscle, as well as lungs, lungs, small intestine, colon, stomach, skin, and bone marrow, while uptake into other organs, including mammary gland, ovary/prostate and brain, was greatly reduced in comparison. Similarly, the conjugate containing the peptide or (RXRRXR)$_2$-XB (SEQ ID NO: 11) displayed selective uptake into heart, muscle, liver, small intestine, stomach, and mammary gland, while uptake into other organs, including mammary gland, ovary/prostate and brain, was greatly reduced in comparison. Optimal tissue uptake (indicated by a *) for various transport peptides is summarized in Table 2 below.

conjugates generally showed low toxicity, with those containing (RX)$_8$ and (RXR)$_4$ having the highest levels of toxicity.

Figure 4:
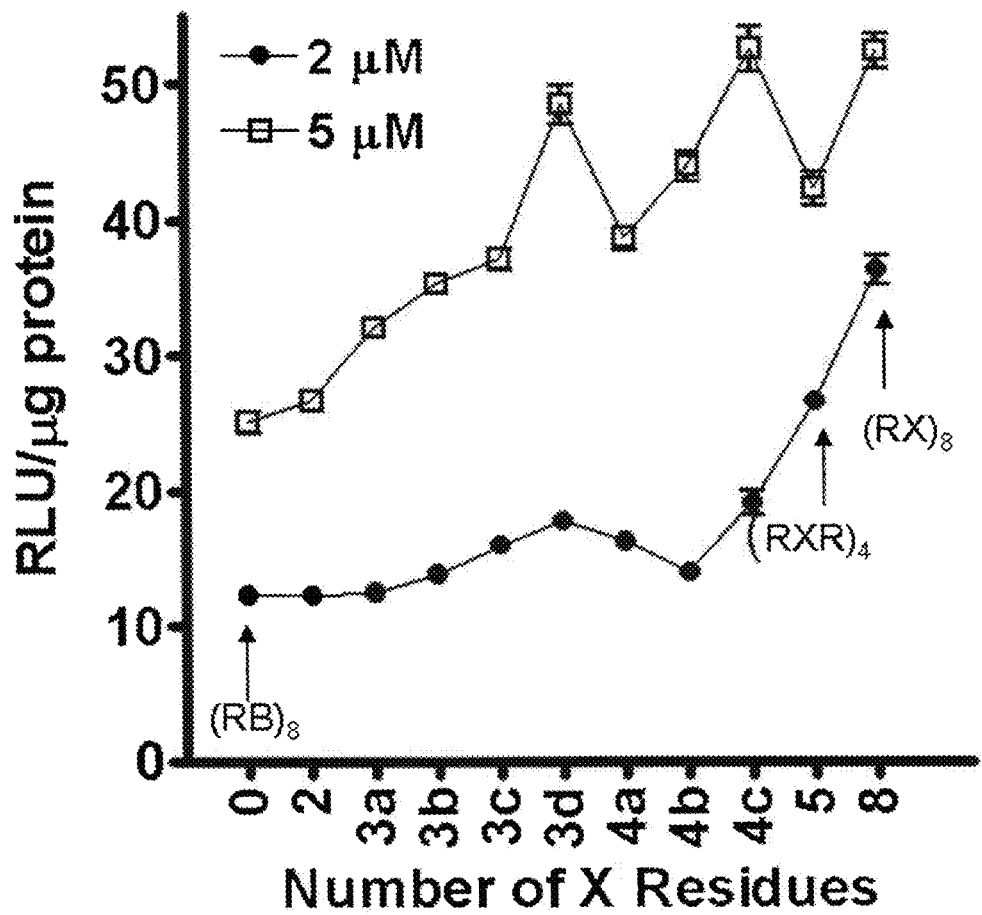
FIG. 4 shows the nuclear antisense activity of carrier peptide-PMO conjugates as a function of the number and position of 6-aminohexanoic acid (Ahx) residues in the peptides.

MTT assay (FIGS. 5A-F). pLuc705 cells were treated at concentrations ranging from 2-60 µM for 24 hr. As shown in FIG. 4, all conjugates, with the exception of those containing (RX)$_8$ (SEQ ID NO: 69) and (RXR)$_4$ (SEQ ID NO: 70) had no toxicity at up to 60 µM. The (RX)$_8$ (SEQ ID NO: 69) and (RXR)$_4$ (SEQ ID NO: 70) conjugates exhibited no toxicity up to 10 µM, while at higher concentrations they reduced cell viability in a concentration-dependent manner, with (RX)$_8$ (SEQ ID NO: 69) being more toxic than (RXR)$_4$ (SEQ ID NO: 70) (FIGS. 5C-D).

Replacement of L-arginine with D-arginine in R$_8$-, (RB)$_8$- and (RXR)$_4$-PMO did not change the viability profiles of these conjugates (FIGS. 5A-C). Surprisingly, the L→D replacement in (RX)$_8$-PMO decreased the toxicity (FIG. 5D).

The eight conjugates containing peptides with fewer than five X residues did not inhibit cell proliferation up to 60 µM (FIG. 5E). Monomers of R or X, individually or in combination, at 500 µM each, produced no inhibition of cell proliferation (FIG. 5F).

The toxicities of the conjugates (RXR)$_4$-PMO, RX(RB)$_2$RX(RB)$_3$RX-PMO (peptide SEQ ID NO: 25) and (RXR)$_3$RBR-PMO (peptide SEQ ID NO: 26) were also evaluated in a human liver HepG2 cells. Of these, only (RXR)$_4$-PMO caused dose-dependent inhibition of cell proliferation, while the other two conjugates had no toxicity up to 60 µM, the highest concentration tested in this study.

Microscopic images. Images of cells treated with 60 µM of the conjugates correlated well with the MTT cell viability data. Cells treated with (RX)$_8$-PMO and (RXR)$_4$-PMO

TABLE 2

| Tissue (Optimal % Correction) | Carrier Peptide Uptake in Tissue Optimal Tissue Targeting Peptides: SEQ ID NO: (see Table 1) |||||||||||||
|---|---|---|---|---|---|---|---|---|---|---|---|---|---|
| | 19 | 20 | 21 | 22 | 23 | 24 | 25 | 11 | 13 | 14 | 27 | 6 | 3 | 26 |
| Heart (>50%) | * | | | | | | | | * | | | | | |
| Leg muscles (>75%) | * | * | * | | * | | * | * | * | | | * | | |
| Liver (>50%) | * | | | * | * | * | | | | | | | * | |
| Kidney (>50%) | | * | | | | | | * | * | * | * | | | |
| Lungs (>30%) | * | | | | | | | * | | * | | | | |
| Sm. Int. (>50%) | * | | * | * | | | * | | | | | | | |
| Colon (>50%) | * | * | | | | * | * | | | * | | | | |
| Stomach (>30%) | * | * | * | | | | | * | | * | | | | |
| Mammary Gland (>75%) | | | | | | | | | * | * | * | | | |
| Thymus (>50%) | | | | | | | | * | | | | | | |
| Spleen (>30%) | | | | | | * | * | | | | | | | |
| Ovary (>50%) | | | | * | | | | | | | | | | |
| Skin (>75%) | * | | | | | | | * | * | | | | | * |
| Bone Marrow (>20%) | | | | | | | | | | * | | | | |
| Brain (>2%) | | | | | * | | | * | | | | | | |

VI. Cellular Toxicity of Carrier Peptide-PMO Conjugates

The cellular toxicity of the various peptide-PMO conjugates was determined by MTT-survival, propidium iodine (PI) exclusion, hemolysis assays, and microscopic imaging. The MTT and PI exclusion assays measure metabolic activity and membrane integrity of cells, respectively. The hemolysis assay determines compatibility with blood. Microscopic images were used to verify the MTT results and observe the general health of the cells. As detailed below, the appeared rounded and detached from the culture well, and appeared to have fewer live cells. Interestingly, cells treated with (rX)$_8$-PMO appeared to have normal morphology and cell density. The replacement of one X of (RXR)$_4$-PMO with one B reduced toxicity significantly; i.e., cells treated with (RXR)$_3$RBR-PMO (peptide SEQ ID NO: 26) had similar density and morphology to the vehicle-treated cells.

Propidium iodine exclusion assay. The effect of the conjugates on integrity of cell membranes was investigated by a propidium iodine (PI) exclusion assay. PI can permeate only unhealthy/damaged membranes; therefore, positive PI fluorescence indicates compromised cell membranes. Only (RXR)$_4$-PMO and (RX)$_8$-PMO conjugates were found to significantly affect membrane integrity at higher concentrations (up to 60 µM tested).

Figure 6A:
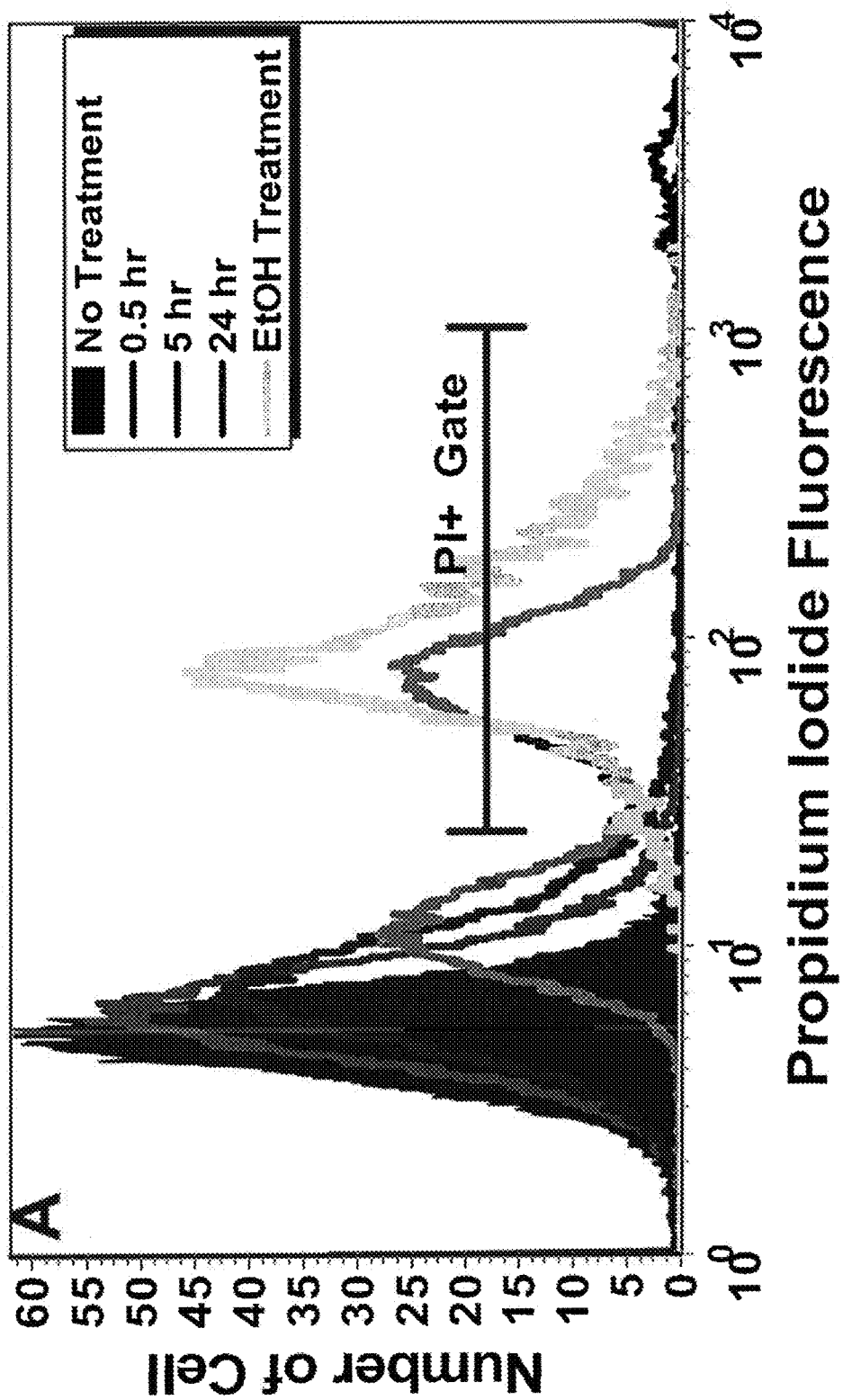

FIG. 6A shows the histograms of pLuc705 cells treated with (RXR)$_4$-PMO at 60 µM for 0.5, 5 and 24 hr. The PI positive (PI+) region was defined by the cells permeabilized with ethanol (positive control) as indicated by the gate in the histogram. The PI histogram shifts from the PI-negative region to PI-positive region in the longer incubations, indicating the conjugate caused membrane leakage in a time-dependent manner. The 0.5 hr- and 5 hr-treatments caused a slight shift towards the PI+ region, while the 24 hr-treatment produced a distinct peak which corresponds to 57% of cells that were in the PI+ region.

Figure 6B:
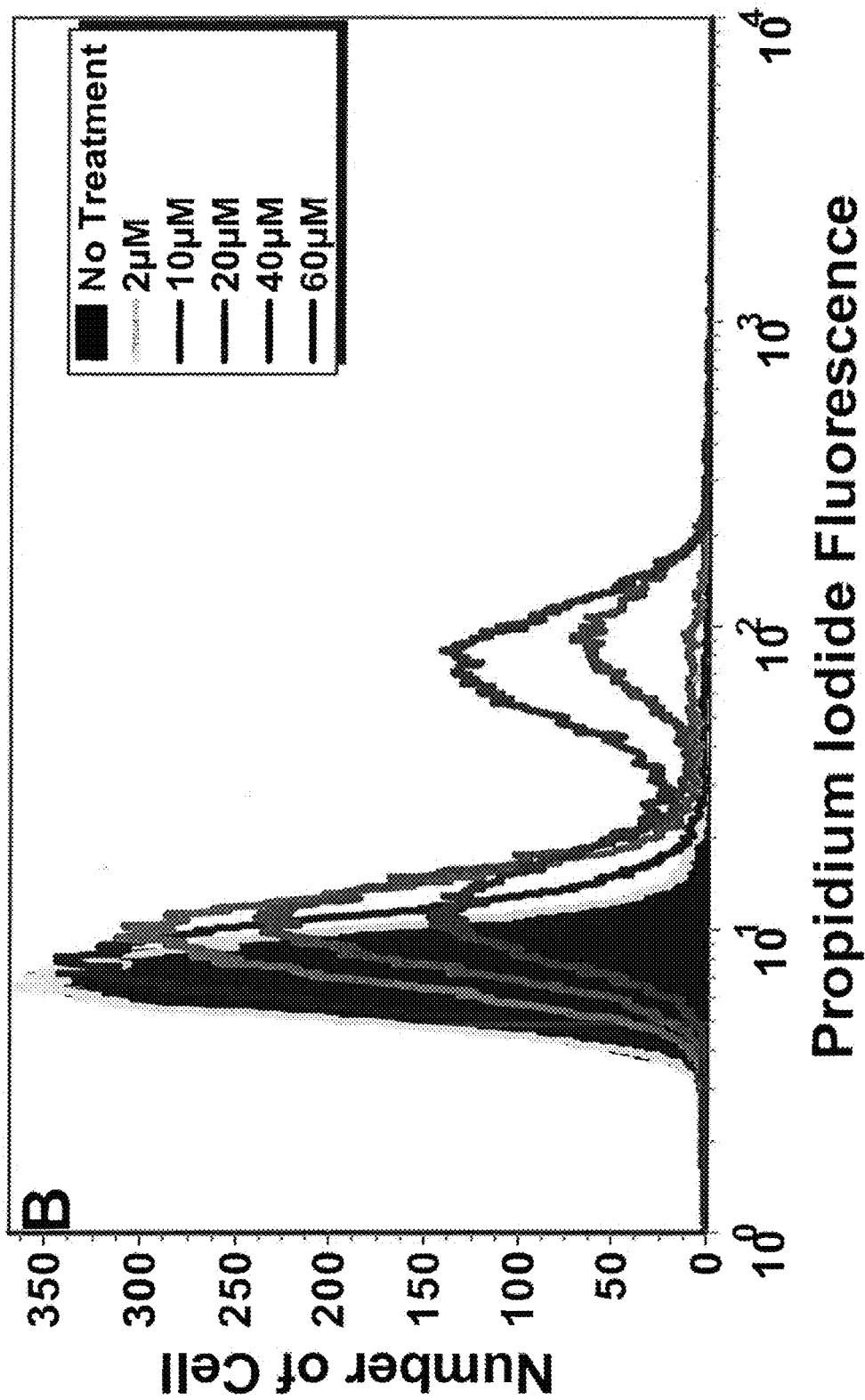
Figure 6C:
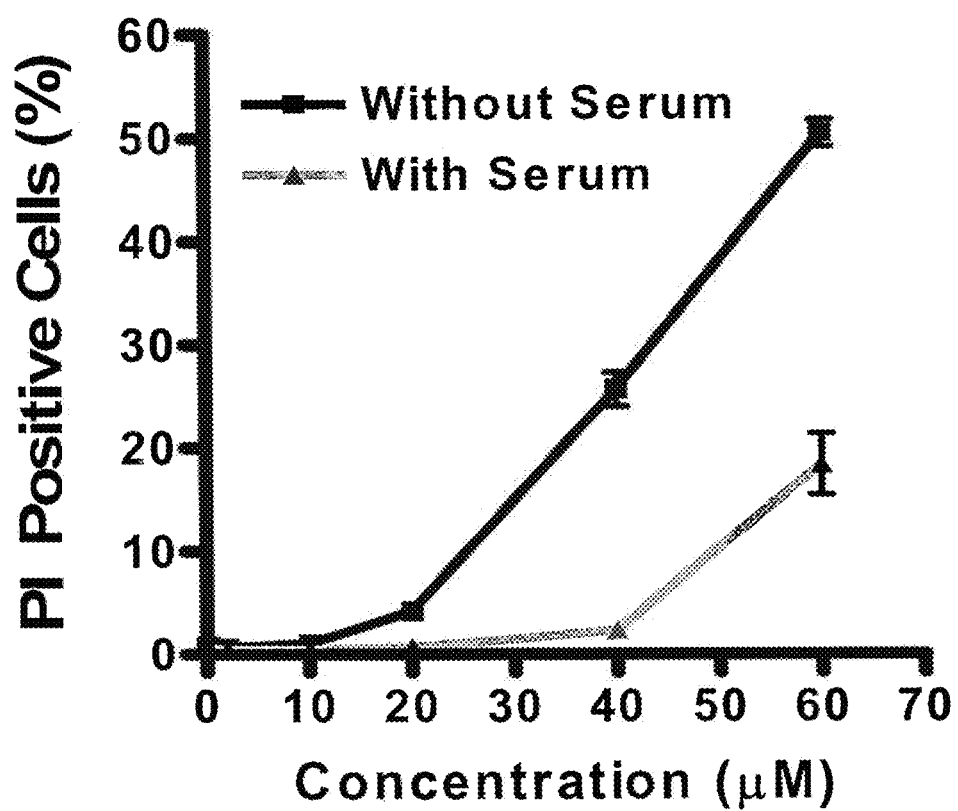

FIG. 6B shows the histograms of cells treated with (RXR)$_4$-PMO at concentrations of 2, 10, 20, 40 and 60 µM for 24 hr. There was no significant PI uptake at concentrations up to 20 µM. At higher concentrations, the PI+ population appeared, and the percentage of PI+ cells increased as the treatment concentration increased, indicating that there were more leaking cells at the higher treatment concentration. Similar concentration- and time-dependent PI uptake profiles were observed for (RX)$_8$-PMO, but not for (RB)$_8$-PMO and the remaining conjugates. Addition of 10% serum to the treatment medium significantly reduced membrane toxicity for the (RXR)$_4$- (FIG. 6C) and (RX)$_8$-PMO conjugates.

Figure 6D:
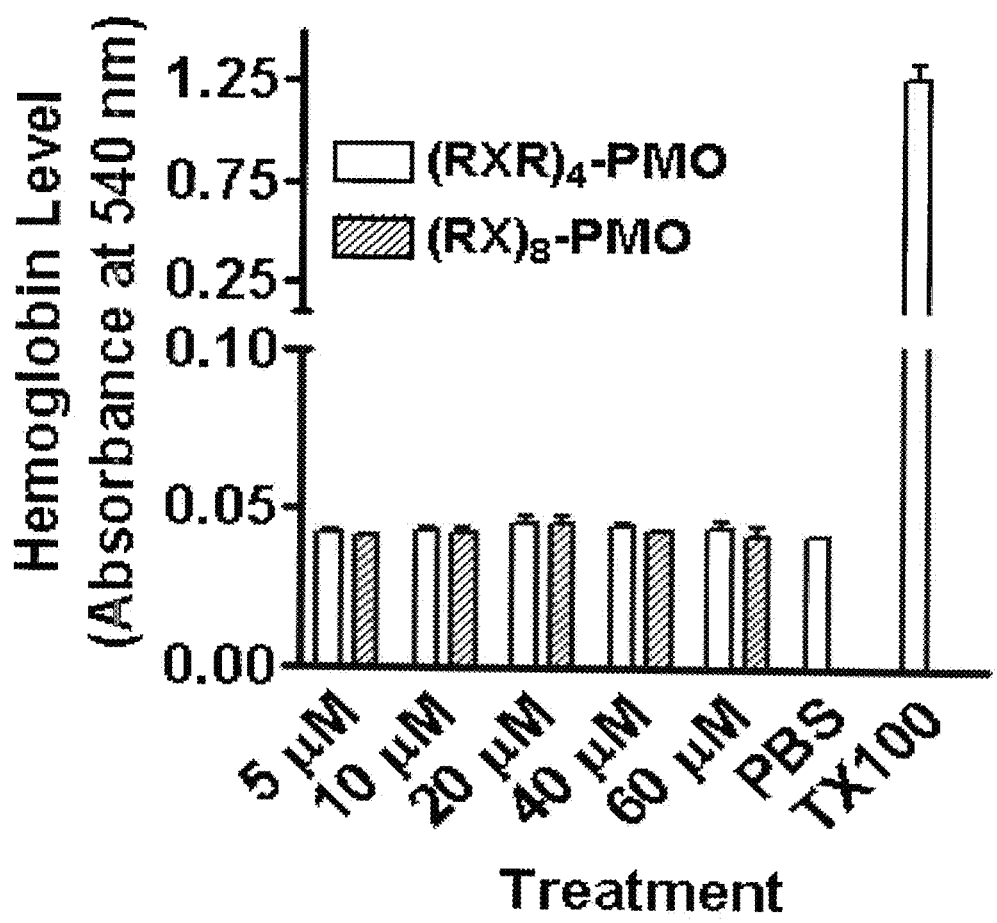

Hemolysis assay. The (RXR)$_4$- and (RX)$_8$-PMO conjugates were tested in a hemolysis assay and found to be compatible with red blood cells. Fresh rat red blood cells were treated with the conjugates at 60 µM, PBS (background) or 0.005% TX-100 (positive control). The supernatants of conjugate- and PBS-treated samples had small and similar amounts of free hemoglobin released, far lower than that of the TX-100-treated samples (FIG. 6D).

Animal studies on compounds containing both (RXRRXR)$_2$XB (SEQ ID NO: 11) and (RXRRBR)$_2$XB (SEQ ID NO: 19) peptides show that the conjugate compounds are well tolerated, with little or no observable toxicity effects at therapeutically effective doses, and with the (RXRRBR)$_2$XB (SEQ ID NO: 19) peptide showing lower toxicity than the (RXRRXR)$_2$XB (SEQ ID NO: 11) peptide at elevated compound doses.

VII. Therapeutic Applications

The carrier peptides and conjugate compounds of the present invention are useful for targeting and delivering an antisense oligomer, such as a PMO, across both the cell and nuclear membranes to the nucleus of muscle cells in skeletal and heart muscle tissue, by exposing the cell to a conjugate comprising the oligomer covalently linked to a carrier peptide as described above.

(A1) Treatment of Duchenne muscular dystrophy. In one embodiment, an antisense oligomer conjugated to a muscle-specific carrier peptide as described herein is used in an improved method for treating Duchenne muscular dystrophy (DMD). Mutations in the human dystrophin gene can be removed from the processed mRNA by antisense oligomers that cause exon skipping of the exon containing the mutation. The resulting processed dystrophin mRNA can encode a functional dystrophin protein. An exemplary antisense oligomer targeted to exon 51 of the human dystrophin gene (SEQ ID NO: 38) induces skipping of exon 51. Other suitable antisense oligomers include those having SEQ ID NOs: 28-36 for human treatment and SEQ ID NO:37 used in the mouse MDX model.

This therapeutic strategy can benefit greatly from the use of muscle-specific carrier peptides (RXRR(B/X)R)$_2$XB, as detailed in Examples 2-4 below. Treatment of the MDX mouse using the M23d-CP06062 PPMO (SEQ ID NO 37 conjugated to SEQ ID NO: 19) compound demonstrated superior delivery of the PPMO to all muscle tissues including cardiac tissues as described in Example 3 and shown in FIGS. 9-12.

Treatment of DMD, in accordance with the invention, comprises:

(i) administering to the subject, an antisense compound comprising a therapeutic oligonucleotide of the type indicated above for restoring the normal reading frame in a mutated dystrophin mRNA, and conjugated to the oligonucleotide, a cell-penetrating peptide having the sequence (RXRR(B/X)R)$_2$XB, where R is arginine; B is β-alanine; and each X is —C(O)—(CH$_2$)$_n$—NH—, where n is 4-6, and (ii) repeating compound administration at least once every one week to once every three months or longer.

Exemplary oligonucleotide sequences include SEQ ID NOs: 28-38. The compound is preferably administered by intravenous or subcutaneous injection to the subject, at a dose between 1-5 mg/kg body weight antisense compound, at a dosing schedule of once a month to once every 2-3 months. For subQ administration, the dose required may be roughly twice that for IV administration. During the course of treatment, the patient is monitored for improvement or stabilization of muscle performance and heart function, according to established procedures. Because muscular dystrophy is a chronic disease, the treatment method will be applied over the subject's lifetime, with dose adjustments being made during the treatment period to achieve a desired level of muscle function and to accommodate patient growth.

As can be seen from the findings in Examples 3 and 4, the treatment method offers a number of important advantages over earlier proposed antisense methods of treating DMD. First, targeting, uptake and antisense activity of the antisense compound into and in both skeletal and heart muscle is efficient, leading to a high percentage of muscle fibers in skeletal and heart muscle showing dystrophin expression. This allows effective treatment with relatively modest compound doses, e.g., in the range 1-5 mg/kg subject weight. Secondly, little or no compound toxicity is observed, as evidenced by no observable increases in muscle damage, inflammatory cellular infiltrates, or necrotic fibers were observed microscopically in the muscles injected with any of the PPMOs and PMO. Finally, the effect of a single dose may be effective for up to three months or more, allowing the patient to be effectively treated by dosing at intervals of no less than one month, and up to 3 months or more between successive treatments.

(A2) Treatment of Myotonic Dystrophy. As the name of the disorder implies the characteristic clinical manifestation in DM is myotonia (muscle hyperexcitability) and muscle degeneration. Affected individuals will also develop insulin resistance, cataracts, heart conduction defects, testicular atrophy, hypogammaglobulinemia and sleep disorders. Symptoms of DM can manifest in the adult or in childhood. The childhood onset form of the disease is often associated with mental retardation. In addition, there is a form of the disease referred to as congenital myotonic dystrophy. This latter form of the disease is frequently fatal and is seen almost exclusively in children born of mothers who themselves are mildly affected by the disease. In congenital DM the facial manifestations are distinctive due to bilateral facial palsy and marked jaw weakness. Many infants with congenital DM die due to respiratory insufficiency before a proper diagnosis of the disease is made.

DM1 initially involves the distal muscles of the extremities and only as the disease progresses do proximal muscles become affected. In addition, muscles of the head and neck are affected early in the course of the disease. Weakness in eyelid closure, limited extraocular movement and ptosis results from involvement of the extraocular muscles. Many individuals with DM1 exhibit a characteristic "haggard" appearance that is the result of atrophy of the masseters (large muscles that raise and lower the jaw), sternocleidomastoids (large, thick muscles that pass obliquely across each side of the neck and contribute to arm movement) and the temporalis muscle (muscle involved in chewing).

Treatment of MD1 comprises or MD2, in accordance with the invention:

(i) administering to the subject, an antisense compound comprising an antisense oligonucleotide having 8-30 bases, with at least 8 contiguous bases being complementary to the polyCUG or polyCCUG repeats in the 3'UTR region of dystrophia myotonica protein kinase (DMPK) mRNA in DM1 or DM2, respectively, and conjugated to the oligonucleotide, a cell-penetrating peptide having the sequence (RXRR(B/X)R)$_2$XB, where R is arginine; B is β-alanine; and each X is —C(O)—(CH$_2$)$_n$—NH—, where n is 4-6, and (ii) repeating the compound administration at least once every one week to once every three months or longer.

As with DMD treatment, the compound is preferably administered by intravenous or subcutaneous injection to the subject, at a dose between 1-5 mg/kg body weight antisense compound, at a dosing schedule of once a month to once every 2-3 months. For subQ administration, the dose required may be roughly twice that for IV administration. During the course of treatment, the patient is monitored for improvement or stabilization of muscle performance, improvement in heart conduction properties and/or reduction in serum reduction in serum creatine kinase. Because myotonic dystrophy is a chronic disease, the treatment method will be applied over the subject's lifetime, with dose adjustments being made during the treatment period to achieve a desired level of muscle function and to accommodate patient growth.

As discussed above for DMD treatment, the treatment method offers a number of important advantages over earlier proposed antisense methods of treating MD1 or MD2. First, targeting, uptake and antisense activity of the antisense compound into and in both skeletal and heart muscle is efficient, as demonstrated for antisense oligonucleotide targeted against muscle dystrophin protein. This allows effective treatment with relatively modest compound doses, e.g., in the range 1-5 mg/kg subject weight. Secondly, little or no compound toxicity is observed, as evidenced by no observable increases in muscle damage, inflammatory cellular infiltrates, or necrotic fibers were observed microscopically in the muscles injected with any of the PPMOs and PMO. Finally, as in the DMD treatment method, the effect of a single dose may be effective for up to three months or more, allowing the patient to be effectively treated by dosing at intervals of no less than one month, and up to 3 months or more between successive treatments.

(A3) Treatment of muscle atrophy. In another embodiment, an antisense oligomer as described herein can be used in a method for treating loss of skeletal muscle mass in a human subject. The steps in the method entail:

(a) measuring blood or tissue levels of myostatin in the subject, (b) administering to the subject, a myostatin-expression-inhibiting amount of an oligomer as described herein, conjugated to (RXRR(B/X)R)$_2$XB, where R is arginine; B is β-alanine; and each X is —C(O)—(CH$_2$)$_n$—NH—, where n is 4-6, and having a base sequence effective to hybridize to an expression-sensitive region of processed or preprocessed human myostatin RNA transcript;

(c) by this administering, forming within target muscle cells in the subject, a base-paired heteroduplex structure composed of human myostatin RNA transcript and the antisense compound and having a Tm of dissociation of at least 45° C., thereby inhibiting expression of myostatin in said cells;

(d) at a selected time following administering the antisense compound, measuring a blood or tissue level of myostatin in the subject; and (e) repeating the administering, using the myostatin levels measured in (d) to adjust the dose or dosing schedule of the amount of antisense compound administered, if necessary, so as to reduce measured levels of myostatin over those initially measured and maintain such levels of myostatin measured in step (d) within a range determined for normal, healthy individuals.

Where the antisense oligomer is effective to hybridize to a splice site of preprocessed human myostatin transcript, it has a base sequence that is complementary to at least 12 contiguous bases of a splice site in a preprocessed human myostatin transcript, and formation of the heteroduplex in step (c) is effective to block processing of a preprocessed myostatin transcript to produce a full-length, processed myostatin transcript. Exemplary antisense sequences are those identified by SEQ ID NOs: 39-43.

Compound doses and dose schedules are similar to those described above for DMD treatment and MD treatment, as are the advantages achievable by the treatment method.

VIII. Combination with Homing Peptides

The oligonucleotide-(RXRR(B/X)R)$_2$XB conjugate compounds of the invention may be used in conjunction with homing peptides selective for the target tissue, to further enhance muscle-specific delivery. An example of this approach can be found in the application of muscle-binding peptides (Samoylova and Smith, 1999; Vodyanoy et al., U.S. Appn. Pubn. No. 20030640466) coupled to antisense oligomers designed to be therapeutic treatments for Duchenne muscular dystrophy (DMD) (Gebski, Mann et al. 2003; Alter, Lou et al. 2006) (PCT Pubn. No. WO2006000057). The heptapeptide sequence ASSLNIA has enhanced in vivo skeletal and cardiac muscle binding properties, as described by Samoylova and Smith. As a further example, a pancreas-homing peptide, CRVASVLPC (SEQ ID NO: 72), mimics the natural prolactin receptor ligand (Kolonin, Sun et al. 2006).

An exemplary dual peptide molecule has a cell penetrating peptide to one terminus, e.g. at the 5' end of the antisense oligomer, as described herein, and a homing peptide coupled to the other terminus, i.e. the 3' terminus. The homing peptide localizes the peptide-conjugated PMO to the target tissue, where the cell-penetrating peptide moiety effects transport into the cells of the tissue.

Alternatively, a preferred exemplary dual peptide molecule would have both a homing peptide (HP) and cell-penetrating peptide (CPP) conjugated to one end, e.g. the 5' terminus of the antisense oligomer, in either a HP-CPP-PMO configuration or, more preferably, a CPP-HP-PMO configuration.

For example, a PMO designed to induce therapeutic exon skipping of the dystrophin gene, as described by Wilton et al. (PCT Publication WO2006/000057), conjugated at the 3' terminus to the muscle-binding peptide ASSLNIA (SEQ ID NO: 51), and further coupled at the 5' terminus to a cell penetrating peptide of the present invention, preferably having enhanced selectivity for muscle tissue, will provide enhanced therapeutic potential in the treatment of DMD. This is exemplified in Example 2, below.

TABLE 3

Examples of Muscle-specific Homing Peptides (HP)

| Target Tissue | Peptide Sequence (NH$_2$ to COOH) | SEQ ID NO. |
|---|---|---|
| Skeletal Muscle-SMP1 | ASSLNIA | 51 |
| SMP2 | SLGSFP | 52 |
| SMP3 | SGASAV | 53 |
| SMP4 | GRSGAR | 54 |
| SMP5 | TARGEHKEEELI | 55 |
| Cardiac Muscle-CMP1 | WLSEAGPVVTVRALRGTGSW | 56 |
| CMP2 | VTVRALRGTSW | 57 |
| CMP3 | VVTVRALRGTGSW | 58 |
| CMP4 | CRPPR | 59 |
| CMP5 | SKTFNTHPQSTP | 60 |

IX. Peptide-Antisense Oligomer Conjugate Compositions

A. Conjugates for Specific Muscle Treatments

Therapeutic conjugates comprising selected transport peptide sequences are also provided by the invention. These include conjugates comprising a carrier peptide (RXRR(B/X)R)$_2$XB, as described herein, conjugated to an oligonucleotide, e.g., PMO, designed for therapeutic action within muscle tissue.

The conjugates may further comprise a targeting moiety effective to bind to tissue specific receptors of a target tissue type, linked to the therapeutic compound or, preferably, to another terminus of the carrier peptide. In particularly preferred embodiments, a homing peptide such as described above is conjugated to therapeutic compound or to the cell-penetrating peptide.

For use in treating Duchenne muscular dystrophy, the conjugate compound comprises a (RXRR(B/X)R)$_2$XB, and conjugated to a terminus of the peptide, an antisense oligonucleotide capable of producing exon skipping in the DMD protein, such as a PMO having SEQ ID NO: 44, to restore partial activity of the DMD protein.

For use in treating myotonic dystrophy DM1 or DM2, the conjugate compound comprises an antisense oligonucleotide having 8-30 bases, with at least 8 contiguous bases being complementary to the polyCUG or polyCCUG repeats in the 3'UTR region of dystrophia myotonica protein kinase (DMPK) mRNA in DM1 or DM2, respectively, and conjugated to the oligonucleotide, a cell-penetrating peptide having the sequence (RXRR(B/X)R)$_2$XB, where R is arginine; B is β-alanine; and each X is —C(O)—(CH$_2$)$_n$—NH—, where n is 4-6. The compound is effective to selectively block the sequestration of muscleblind-like 1 protein (MBNL1) and/or CUGBP in heart and quadricep muscle in a myotonic dystrophy animal model.

For use in treating muscle atrophy, the conjugate compound comprises an antisense oligonucleotide effective to inhibit myostatin expression in a subject, and conjugated to the oligonucleotide, a cell-penetrating peptide having the sequence (RXRR(B/X)R)$_2$XB, where R is arginine; B is β-alanine; and each X is —C(O)—(CH$_2$)$_n$—NH—, where n is 4-6. The compound is effective to inhibit myostatin expression in muscle tissues.

B. Morpholino Oligomers Having Cationic Intersubunit Linkages

In preferred embodiments, as noted above, the antisense oligomer is a phosphorodiamidate morpholino oligonucleotide (PMO). The PMO may include between about 20-50% positively charged backbone linkages, as described below and further in PCT Pubn. No. WO 2008036127, which is incorporated herein by reference.

Figure 1B:
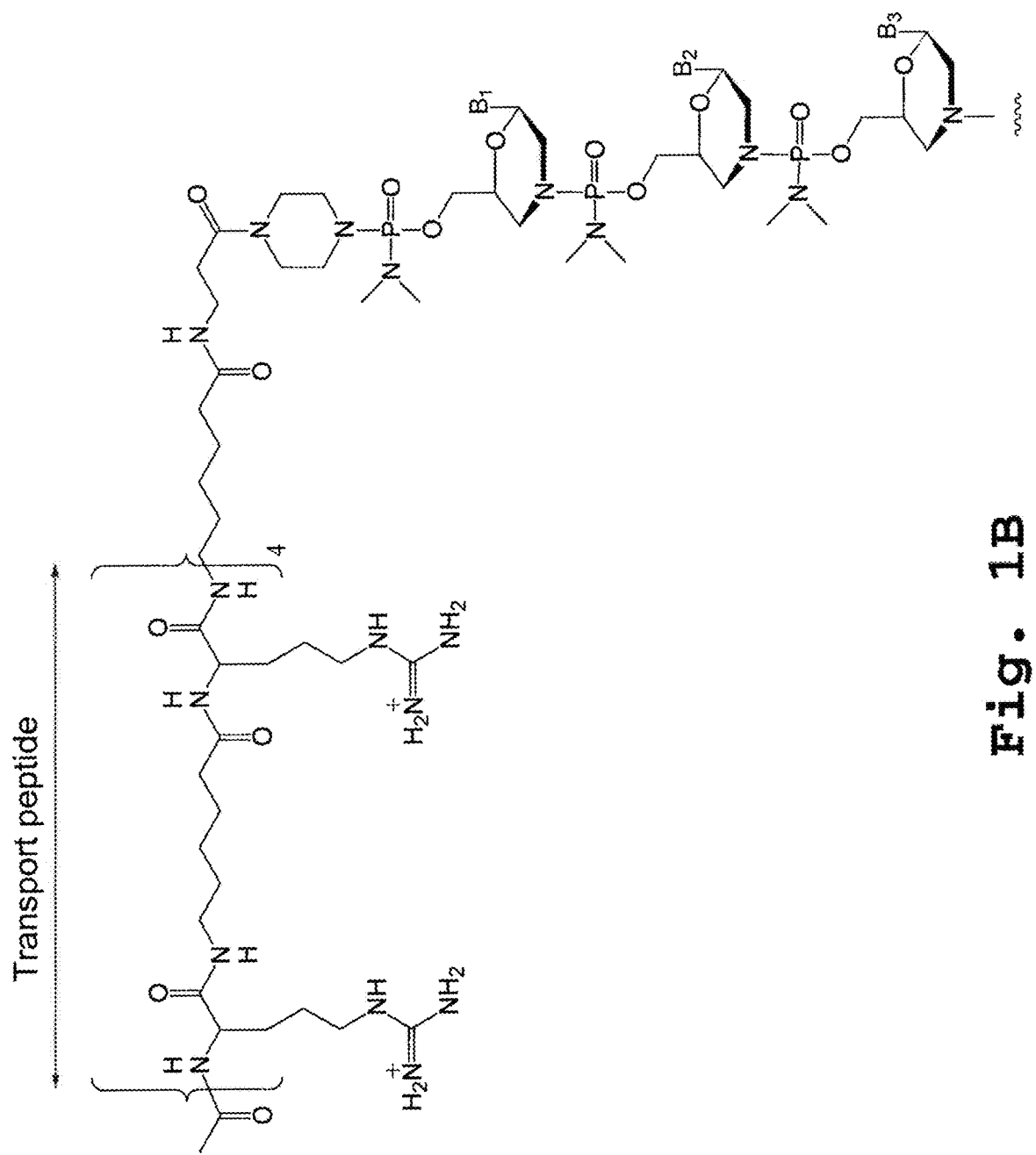
Figure 1C:
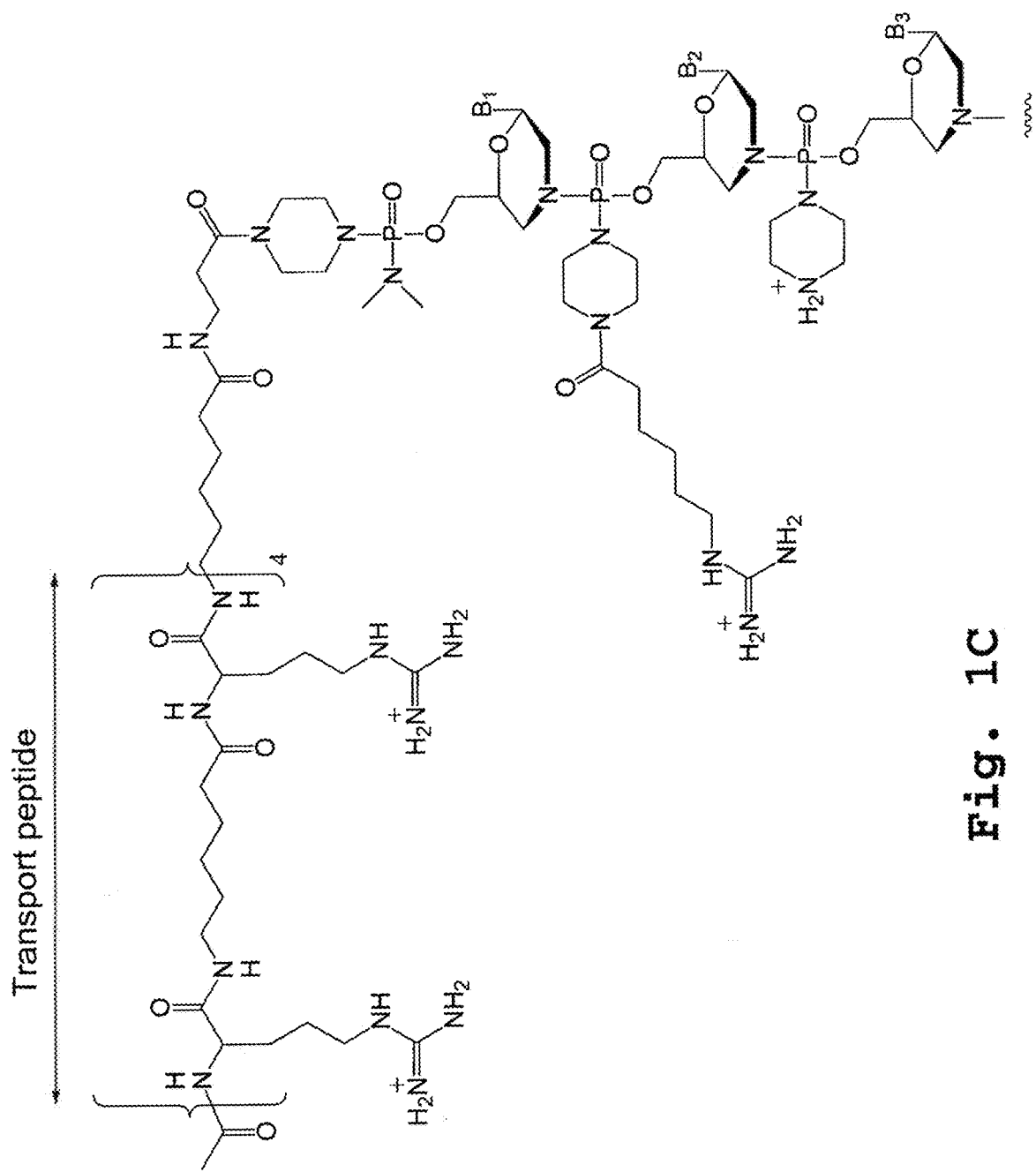

The cationic PMOs (PMO+) are morpholino oligomers in which at least one intersubunit linkage between two consecutive morpholino ring structures contains a pendant cationic group. The pendant group bears a distal nitrogen atom that can bear a positive charge at neutral or near-neutral (e.g. physiological) pH. Examples are shown in FIGS. 1B-C.

The intersubunit linkages in these oligomers are preferably phosphorus-containing linkages, having the structure:

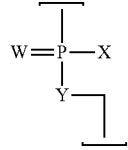

where
W is S or O, and is preferably O,
X=NR$^1$R$^2$ or OR$^6$,
Y=O or NR$^7$,
and each said linkage in the oligomer is selected from:
(a) uncharged linkage (a), where each of R$^1$, R$^2$, R$^6$ and R$^7$ is independently selected from hydrogen and lower alkyl;
(b1) cationic linkage (b1), where X=NR$^1$R$^2$ and Y=O, and NR$^1$R$^2$ represents an optionally substituted piperazino group, such that R$^1$R$^2$ =—CHRCHRN(R$^3$)(R$^4$)CHRCHR—, where
each R is independently H or CH$_3$,
R$^4$ is H, CH$_3$, or an electron pair, and
R$^3$ is selected from H, lower alkyl, e.g. CH$_3$, C(=NH)NH$_2$, Z-L-NHC(=NH)NH$_2$, and {C(O)CHR'NH}$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where X=NR$^1$R$^2$ and Y=O, R$^1$=H or CH$_3$, and R$^2$=LNR$^3$R$^4$R$^5$, where L, R$^3$, and R$^4$ are as defined above, and R$^5$ is H, lower alkyl, or lower (alkoxy)alkyl; and
(b3) cationic linkage (b3), where Y=NR$^7$ and X=OR$^6$, and R$^7$=LNR$^3$R$^4$R$^5$, where L, R$^3$, R$^4$ and R$^5$ are as defined above, and R$^6$ is H or lower alkyl;

and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 80%, 10% to 50%, or 10% to 35% of the linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g. $CH_3$, $C(=NH)NH_2$, and $C(O)$-L-NHC$(=NH)NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g. —$CH_2$—$CH_2$—), alkoxy (—C—O—), and alkylamino (e.g. —$CH_2$—NH—), with the proviso that the terminal atoms in L (e.g., those adjacent to carbonyl or nitrogen) are carbon atoms. Although branched linkages (e.g. —$CH_2$—$CHCH_3$—) are possible, the linker is preferably unbranched. In one embodiment, the linker is a hydrocarbon linker. Such a linker may have the structure —$(CH_2)_n$—, where n is 1-12, preferably 2-8, and more preferably 2-6.

The use of embodiments of linkage types (b1), (b2) and (b3) above to link morpholino subunits may be illustrated graphically as follows:

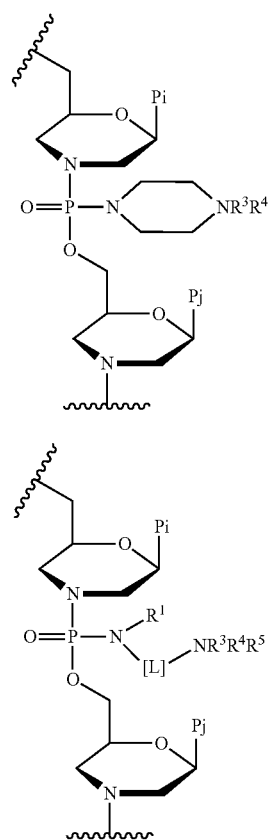

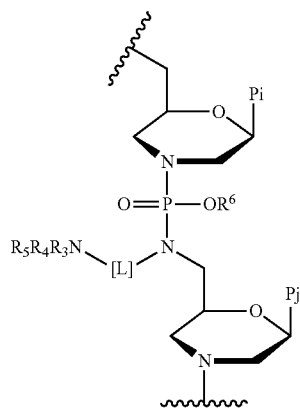

Preferably, all cationic linkages in the oligomer are of the same type; i.e. all of type (b1), all of type (b2), or all of type (b3). The base-pairing moieties Pi may be the same or different, and are generally designed to provide a sequence which binds to a target nucleic acid.

In further embodiments, the cationic linkages are selected from linkages (b1') and (b1") as shown below, where (b1') is referred to herein as a "Pip" linkage and (b1") is referred to herein as a "GuX" linkage:

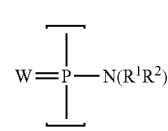

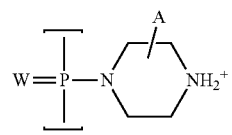

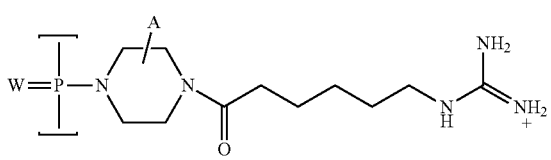

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 20% to 80%, 20% to 50%, or 20% to 30% of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

Oligomers having any number of cationic linkages can be used, including fully cationic-linked oligomers. Preferably, however, the oligomers are partially charged, having, for example, 5, 10, 20, 30, 40, 50, 60, 70, 80 or 90 percent cationic linkages. In selected embodiments, about 10 to 80, 20 to 80, 20 to 60, 20 to 50, 20 to 40, or about 20 to 35 percent of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 15 to 25 subunits. For example, a cationic oligomer having 19-20 subunits, a useful length for an antisense oligomer, may ideally have two to seven, e.g. four to six, or three to five, cationic linkages, and the remainder uncharged linkages. An oligomer having 14-15 subunits may ideally have two to five, e.g. 3 or 4, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

As noted above, the substantially uncharged oligonucleotide may be modified to include one or more charged linkages, e.g. up to about 1 per every 2-5 uncharged linkages, typically 3-5 per every 10 uncharged linkages. Optimal improvement in antisense activity is seen where up to about half of the backbone linkages are cationic. Some, but not maximum enhancement is typically seen with a small number e.g., 10-20% cationic linkages; where the number of cationic linkages exceeds 50-60%, the sequence specificity of the antisense binding to its target may be compromised or lost.

The enhancement seen with added cationic backbone charges may, in some case, be further enhanced by distributing the bulk of the charges close of the "center-region" backbone linkages of the antisense oligonucleotide, e.g., in a 20-mer oligonucleotide with 8 cationic backbone linkages, having 70%-100% of these charged linkages localized in the 10 centermost linkages.

C. Other Oligomer Types

Delivery of alternative antisense chemistries can also benefit from the disclosed carrier peptide. Specific examples of other antisense compounds useful in this invention include those in which at least one, or all, of the internucleotide bridging phosphate residues are modified phosphates, such as methyl phosphonates, phosphorothioates, or phosphoramidates. Also included are molecules wherein at least one, or all, of the nucleotides contains a 2' lower alkyl moiety (e.g., C1-C4, linear or branched, saturated or unsaturated alkyl, such as methyl, ethyl, ethenyl, propyl, 1-propenyl, 2-propenyl, or isopropyl).

In other oligonucleotide mimetics, both the sugar and the internucleoside linkage, i.e., the backbone, of the nucleotide units are modified. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-phosphate backbone of an oligonucleotide is replaced with an amide containing backbone, in particular an aminoethylglycine backbone.

Modified oligonucleotides may be classified as "chimeric", e.g. containing at least one region wherein the oligonucleotide is modified so as to confer increased resistance to nuclease degradation or increased cellular uptake, and an additional region for increased binding affinity for the target nucleic acid.

EXAMPLES

The following examples are intended to illustrate but not to limit the invention.

Materials and Methods

In Vitro and In Vivo Assays

Nuclear Activity Assay. The effectiveness of each P-PMO conjugate was determined in a splice-correction assay to assess nuclear activity which utilizes a P-PMO targeted splice site in a plasmid created by an interruption in the luciferase coding sequence by the human β-globin thalassemic intron 2 which carries a mutated splice site at nucleotide 705 (pLuc705). The plasmid is stably transfected in HeLa S3 cells, allowing for easy comparison of the relative efficiency of various carrier peptides to deliver PMO (705; 5'-CCT CTT ACC TCA GTT ACA-3'; SEQ ID NO: 1) capable of restoring splice-correction in cell nuclei. Cells were cultured in RPMI 1640 medium supplemented with 2 mM L-Glutamine, 100 U/mL penicillin, and 10% fetal bovine serum (FBS) at 37° C. in a humidified atmosphere containing 5% $CO_2$, and seeded for 20 hours prior to 2 μM P-PMO treatment. All cell treatments with P-PMO were carried out in OptiMEM medium with or without FBS for 24 hours. After cell treatment, restoration of correct splice-correction was measured by positive readout of luciferase expression in cell lysates on an Flx 800 microplate fluorescence-luminescence reader with excitation at 485 nm and emission at 524 nm.

Cell Uptake Assay. The cellular uptake of P-PMO in HeLa pLuc705 cells was determined using 3'-carboxyfluorescein-tagged P-PMO (P-PMOF) and flow cytometry. Cells were seeded for 20 hours prior to 2 μM P-PMOF treatment. After treatment, cells were trypsinized to remove any cell membrane-bound P-PMOF, and washed and resuspended in PBS (Hyclone, Ogden, Utah) containing 1% FBS and 0.2% $NaN_3$. Cell uptake of P-PMOF was then determined by flow cytometry on a FC-500 Beckman Coulter (Fullerton, Calif.) cytometer and data was processed using FCS Express 2 software (De Novo Software, Thornhill, Ontario, Canada).

RNA Extraction. Tissue RNA was extracted using Qiagen's RNeasy Mini Kit (Qiagen USA, Valencia, Calif.) per manufacturer's protocol. All isolated RNA was stored at −80° C.

RT-PCR. Restoration of splice-correction was determined by RT-PCR amplification of EGFP mRNA extracted from tissues harvested from P-PMO treated EGFP-654 transgenic mice using the Invitrogen SuperScript™ III One-Step RT-PCR System.

Toxicity Assays

The cellular toxicity of P-PMOs was determined by methylthiazoletetrazolium-survival (MTT), propidium iodine (PI) exclusion, and hemolysis assays, which measured the effects of the P-PMOs on cellular metabolic activity, membrane integrity, and red blood cell compatibility, respectively.

MTT Analysis. For MTT analysis, cells were seeded at a concentration of 9000 cells/well in 96 well plates for 20 hours then treated with P-PMO ranging in concentration from 2-60 µM. MTT solution was then added to the cells for 4 hours and cellular metabolic activity was measured by reading the absorbance of the treatment medium and normalizing the absorbance of the P-PMO treated samples to the absorbance mean of untreated samples. Microscopic images of P-PMO treated cells were visualized on a Nikon Diaphot inverted microscope (Melville, N.Y.) and processed by Magnafire software (Optronics, Goleta, Calif.) for correlation with MTT results. All assays were done using HeLa pLuc705 cells. Microscopic images of P-PMO treated cells were visualized on a Nikon Diaphot inverted microscope (Melville, N.Y.) and processed by Magnafire software (Optronics, Goleta, Calif.) for correlation with MTT results. All assays were done using HeLa pLuc705 cells.

Propidium Iodine-Exclusion. For PI-exclusion analysis, cells were seeded at a concentration of 100,000 cells/well in 12-well plates for 20 hours then treated with P-PMO ranging in concentration from 2-60 µM. Cells were then trypsinized, washed in PBS, and resuspended in PBS containing PI for 15 minutes. Detection of unhealthy or damaged cellular membranes was done by analyzing cells for PI uptake by flow cytometry.

Red Blood Cell Compatibility. Hemolytic activities in red blood cells exposed to P-PMO ranging in concentration from 2-60 µM was determined using fresh rat blood according to an established method (Fischer, Li et al. 2003).

MDXMouse Experiments. Experiments using the MDX mouse strain were performed essentially as described by Jearawiriyapaisarn, Moulton et al., 2008.

Example 1. Evaluation of Cell Penetrating Peptide Conjugated PMOs in the EGFP-654 Transgenic Mouse Model A PMO (designated 654; 5'-GCT ATT ACC TTA ACC CAG-3'; SEQ ID NO: 2) designed to restore correct splicing in the enhanced green fluorescent protein (EGFP) gene was conjugated to various cell penetrating peptides (SEQ ID NOs: 2, 3, 6, 11, 13-14, 19, 20-27) to produce P-PMOs (peptide-conjugated PMOs), which were evaluated in vivo for their splice-correction activity and toxicity in the EGFP-654 transgenic mouse model (Sazani, Gemignani et al. 2002). In this model, the EGFP-654 gene encoding for functional EGFP is interrupted by an aberrantly-spliced mutated intron, and cellular uptake of EGFP-654 targeted P-PMOs can be evaluated by RT-PCR detection of the restored EGFP-654 splice product in tissues.

Female EGFP-654 transgenic mice were injected IP once daily for 4 consecutive days with saline or a 12.5 mg/kg dose of P-PMO. Post treatment on day 4, the heart, muscles, liver, kidney, lungs, small intestine, colon, stomach, mammary gland, thymus, spleen, ovary, skin, bone marrow, and brain were harvested, and extracted RNA was evaluated by RT-PCR and densitometry of PCR products to determine % correction. Toxicity of P-PMOs was evaluated by measurement of mouse weights over the course of treatments and immediately prior to necropsy.

Restoration of functional EGFP splice products post treatment with various P-PMOs based on RT-PCR analysis of tissues is shown in FIGS. 7A-P. Analysis of toxicity based on weights from P-PMO treated mice indicated minimal toxicity (not shown). Optimal carrier peptide uptake for each tissue (indicated by a *) based on these results is summarized in Table 2 (see above).

Example 2. Evaluation of PMOs Conjugated to a Cell Penetrating Peptide (CPP) and/or a Muscle Specific Homing Peptide (HP) in the MDX Murine Model of Duchenne Muscular Dystrophy MDX mice were treated with a series of P-PMO (peptide-conjugated PMOs) containing various combinations of muscle-specific CPPs and HPs conjugated to the M23d antisense PMO. The muscle specific CPP used was the "B peptide", also designated CP06062 (SEQ ID NO: 19), and the muscle specific homing peptide, designated SMP1, was SEQ ID NO: 51. Four combinations were tested including CP06062-PMO, MSP-PMO, CP06062-MSP-PMO and MSP-CP06062-PMO, whose compositions are shown in the appended Sequence Table. The M23d antisense PMO (SEQ ID NO: 37) has a sequence targeted to induce an exon 23 skip in the murine dystrophin gene and restores functional dystrophin.

The mice received six weekly intravenous injections of a 3 mg/kg dose. The treated mice were sacrificed and various muscle tissues were removed and stained for full-length dystrophin using a dystrophin-specific fluorescent antibody stain.

The results for the CP06062-PMO, MSP-CP06062-PMO and CP06062-MSP-PMO conjugates in five different muscle tissues are shown in FIG. 8. As can be seen, the dystrophin-specific stain is in much greater evidence for the MSP-CP06062-PMO compound than for the other two conjugates, with the exception of heart muscle, where the CP06062-MSP-PMO conjugate appeared to have the greatest activity. The observation that the CP06062-MSP-PMO compound was more effective than the CP06062-PMO conjugate was confirmed by immunoblot and PCR assays (data not shown). In separate experiments (data not shown), an MSP-PMO conjugate induced full-length dystrophin at a level less than the CP06062-PMO conjugate.

Additional examples of muscle-specific delivery of the CP06062-M23d conjugate to tissues of the MDX mouse can be found in Jearawiriyapaisarn, Moulton et al., 2008, cited above, which is incorporated herein by reference.

In summary, the combination of the muscle specific homing peptide and muscle specific cell penetrating peptide significantly improved the delivery of the M23d antisense peptide as measured in this in vivo system. The MSP-CP06062-PMO ordering of the peptide moieties was observed to induce the highest level of full-length dystrophin and is a preferred embodiment.

Example 3. Improved Cardiac Function in Dystrophin-Deficient Mice by a (RXRRBR)$_2$XB-Conjugated PMO It has been demonstrated that a PMO (M23d; SEQ ID NO: 37) targeting the junction of exon 23 and intron 23 of mouse dystrophin (referred to as M23d hereafter), was able to induce up to functional levels of dystrophin expression in some skeletal muscles by regular i.v. injections in mdx mice (Alter, J., F. Lou et al. (2006)). However, dystrophin expression induced by PMO required high doses and was highly variable between muscles and myofibers in terms of observed efficacy. Of greater concern, cardiac muscle seemed to be refractory to the antisense therapy, failing to produce detectable dystrophin even after repeated treatment (seven times at ≈60 mg/kg PMO per injection; Alter, J., F. Lou et al. (2006)). Both potency and cardiac delivery represent major limitations to antisense therapy as an effective treatment for muscle-specific diseases such like DMD, DM1 and DM2. Because DMD patients live longer owing to improved multidisciplinary patient care, rescuing dystrophin expression in cardiac muscle becomes more critical for their longevity and quality of life. More importantly, restoration of dystrophin only in skeletal muscles may exacerbate the failure of heart function if dystrophin expression cannot be effectively restored in cardiac muscle. It is not understood why PMO does not induce dystrophin expression effectively in cardiac muscle even at high doses but low delivery efficiency seems to be the most important contributing factor (Alter, J., F. Lou et al. (2006)). This example describes experiments using a cell-penetrating peptide-conjugated PMO (SEQ ID NO: 62, M23d-CP06062 (SEQ ID NO:37, SEQ ID NO:19); in the MDX mouse model. The results demonstrate the restoration of almost normal levels of dystrophin in cardiac and other types of muscles bodywide in dystrophic mdx mice, with improvement in muscle strength and cardiac function. The latter prevents heart failure under increased workload conditions induced by dobutamine. Repeated treatment maintains levels of dystrophin and ameliorates pathology, with significant reduction in levels of serum creatine kinase without immune response.

To improve the efficiency of exon skipping in muscles, particularly in cardiac muscle, several arginine-rich cell-penetrating peptides conjugated to the same M23d PMO (SEQ ID NO: 62) were tested in the MDX mouse model. The M23d-PMO conjugated to the (RXRRBR)$_2$XB (SEQ ID NO: 19) (also referred to herein as CP06062 peptide) showed the highest efficiency for skipping exon 23 by i.m. injection in the adult (age 4-5 weeks) MDX mouse (FIG. 9).

Strong dystrophin expression was induced in 85% of the fibers in the entire tibialis anterior (TA) muscle after injection of 2 micrograms of M23d-CP06062 PPMO (FIG. 9). The same amount of unconjugated M23d PMO produced only 14% dystrophin-positive fibers. A sequence-scrambled PPMO (with the antisense oligomer sequence not complementary to the dystrophin gene but the same base composition as M23d) showed no effect on dystrophin production (not shown). Specific skipping of exon 23 was confirmed by RT-PCR and subsequent sequencing. No increases in muscle damage, inflammatory cellular infiltrates, or necrotic fibers were observed microscopically in the muscles injected with any of the PPMOs and PMO.

Systemic treatment was investigated by administration of a single dose of 30 mg/kg of M23d-CP06062 PPMO i.v. into adult MDX mice. Administration of this amount of unmodified M23d PMO induced dystrophin expression in 5% or less of muscle fibers of all skeletal muscles and no detectable dystrophin in cardiac muscle when examined 2 weeks after injection (Alter, J., F. Lou et al. (2006)). In striking contrast, treatment with M23d-CP06062 PPMO produced strong dystrophin expression in 100% of fibers of all skeletal muscles examined, including the TA, quadriceps, gastrocnemius, abdominal, intercostals, diaphragm, and biceps (FIG. 10, B-D). Expression of dystrophin was highly homogeneous throughout the entire length of the muscles (from tendon to tendon). In fact, the levels of dystrophin expression in the muscles of the M23d-CP06062 PPMO-treated mice were difficult to distinguish from that in the muscles of normal C57BL mice by immunohistochemical analysis (FIG. 10, B-D). However, variation in fiber size and specifically the presence of central nucleation in most muscle fibers were the unmistakable remaining pathology of the mdx mouse. Consistently, near-normal levels (91-100%) of dystrophin were detected by Western blot (FIG. 10, E). The size of the M23d-CP06062 PPMO-induced dystrophin was indistinguishable from that of the normal dystrophin. Similarly, dystrophin mRNA skipped with exon 23 accounted for 80-86% of RT-PCR products in all skeletal muscles (FIG. 10, G). No off-target skipping of the neighboring exons was observed. Precise skipping of exon 23 was confirmed by sequencing (FIG. 10, H). Restoration of dystrophin expression also restored the α dystroglycan, α sarcoglycan, and β sarcoglycan on fiber membrane (not shown). Dystrophin expression was not observed in the muscles of the mdx mice treated with scrambled PPMO (FIG. 10, B-G).

Importantly, immunohistochemistry demonstrated membrane-localized dystrophin in 94% of cardiac muscle fibers of mdx mice treated with the single dose of M23d-CP06062 PPMO, although the levels of dystrophin varied (FIG. 10, D). Dystrophin was expressed at near-normal levels in most areas of the cardiac muscle. A 58% normal dystrophin level was demonstrated by Western blot (FIG. 10, E). Consistently, dystrophin mRNA with exon 23 skipped accounted for 63% of the dystrophin transcript by RT-PCR (FIG. 10, G).

Regular injections of the arginine-rich peptide to maintain or further enhance dystrophin expression was investigated. A group of five adult mdx mice received a 3-month treatment with repeated (six times) i.v. injections of 30 mg/kg of M23d-CP06062 PPMO at biweekly intervals. Two weeks after the last injection, dystrophin expression remained in 100% of muscle fibers in all skeletal muscles, including the diaphragm and smooth muscles in the small intestine (FIGS. 11, A-C, FIG. 12). The levels of dystrophin expression detected by both immunohistochemistry and Western blot in the M23d-CP06062 PPMO-treated mdx mice were again indistinguishable from those in normal C57BL mouse (FIG. 11, D). The dystrophin mRNA with exon 23 skipped accounted for nearly 90% (85-92%) of total dystrophin mRNA by RT-PCR in all skeletal muscles (FIG. 11, F).

Figure 13A:
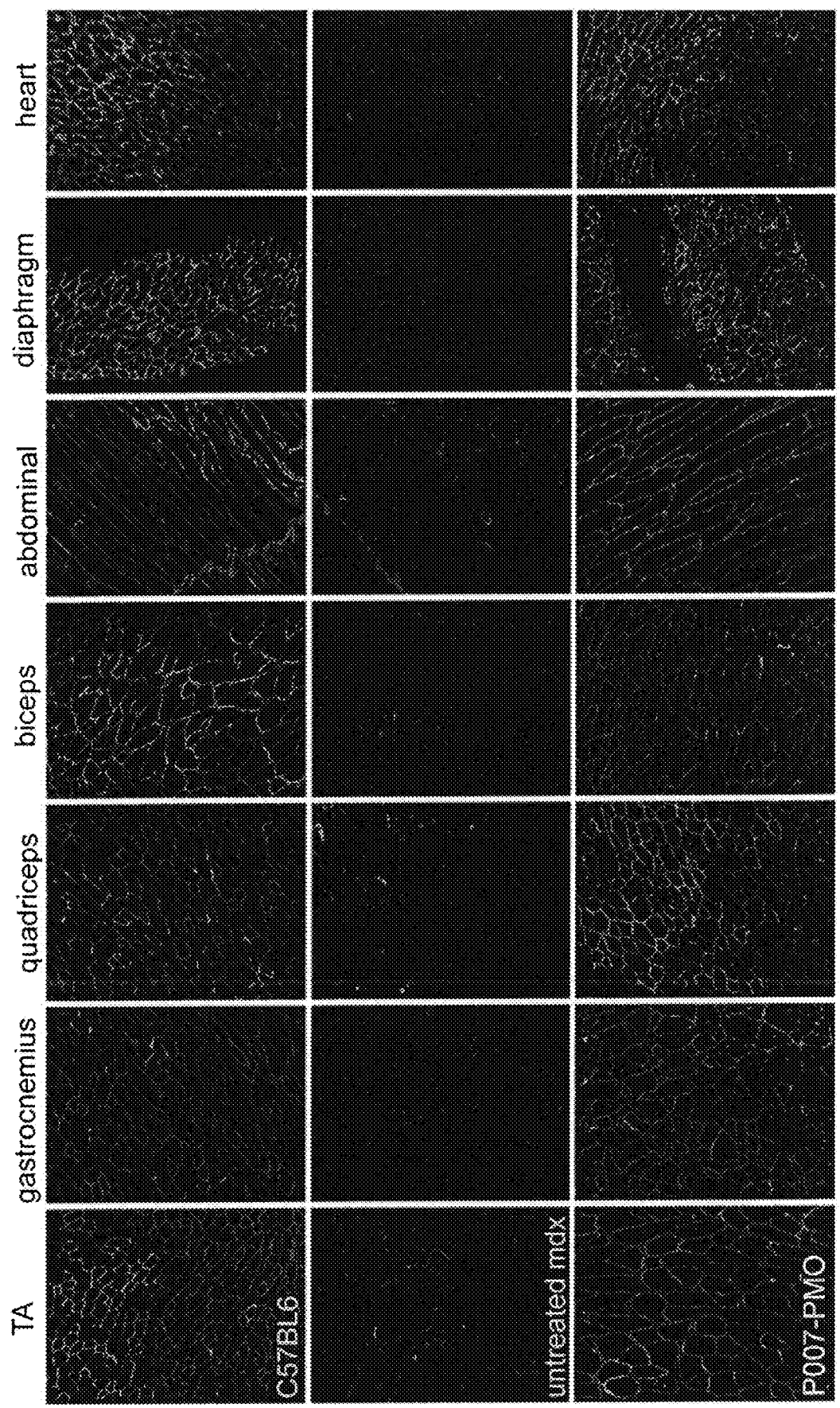

Example 4. Single Low-Dose (RXRRXR)$_2$XB PPMO Conjugates Restore Dystrophin Expression in Muscle and Cardiac Tissue Single intravenous injections of PPMO conjugates to restore dystrophin expression systemically was investigated. A 25 mg/kg single injection administration protocol was tested with the (RXRRXR)$_2$XB-M23d PPMO conjugate (SEQ ID NO: 37 conjugated to SEQ ID NO: 11) administered via the mouse tail vein. Three weeks following single injections, all skeletal muscle fibres immunostained positive for sarcolemmal dystrophin. The intensity of dystrophin expression was near normal in most skeletal muscle groups analysed, although slightly lower in biceps as shown (FIG. 13A). Widespread, uniform expression of dystrophin protein over multiple tissue sections within each muscle group was detected in hind limb, fore limb, abdominal wall and diaphragm muscles. Surprisingly, no obvious area-to-area variation was found within individual muscle groups as previously reported with the systemic delivery of naked PMO AOs (Alter, J., F. Lou et al. (2006)). RT-PCR results revealed almost total exon skipping of the mutated transcript with highly effective skipping of mdx dystrophin exon 23 (FIG. 13B) in all skeletal muscles analysed including the diaphragm. Less efficient molecular correction was observed in heart, where 50% of the mutated transcript was found to be exon skipped by RT-PCR. A shorter band was also detected in the RT-PCR assay in many analysed tissues, which was likely to correspond to a skipped transcript lacking exons 22 and 23. Subsequent sequencing of this PCR fragment confirmed that the minor transcript product contained exon 22 and 23 deletions.

To quantify the levels of dystrophin protein restored, western blot analysis was undertaken, using total protein extracted from all muscle groups including heart, and from normal C57 TA and heart muscle tissues as positive controls. This indicated that between 25 and 100% of normal dystrophin protein levels had been restored in body-wide skeletal muscles following the single systemic AO injection. Of particular significance were the levels approaching 100% restoration of dystrophin protein that were detected in distal muscle groups, i.e. TA and biceps, while even in the diaphragm almost 25% of normal dystrophin protein was restored (FIG. 13C).

Although the invention has been described with respect to certain embodiments and examples, it will be appreciated that various changes, modifications, and additions may be made without departing from the claimed invention.

Sequence Table

| Designation(s) | Sequence | SEQ ID NO.[a] |
|---|---|---|
| Antisense Oligomers | | |
| 705 | 5'-CCT CTT ACC TCA GTT ACA-3' | 1 |
| 654 | 5'-GCT ATT ACC TTA ACC CAG-3' | 2 |
| Cell-Penetrating Peptides (CPP) | | |
| $R_8$ | RRRRRRRR-XB | 3 |
| $r_8$ | rrrrrrrr-XB | 4 |
| $R_9$ | RRRRRRRRR-XB | 5 |
| $(RX)_8$ | RXRXRXRXRXRXRXRX-B | 6 |
| $(rX)_8$ | rXrXrXrXrXrXrXrX-B | 7 |
| $(RX)_7$ | RXRXRXRXRXRXRX-B | 8 |
| $(RX)_5$ | RXRXRXRXRX-B | 9 |
| $(RX)_3$ | RXRXRX-B | 10 |
| $(RXR)_4$ | RXRRXRRXRRXR-B | 11 |
| $(rXR)_4$ | rXRrXRrXRrXR-B | 12 |
| $(rXr)_4$ | rXrrXrrXrrXr-XB | 13 |
| $(RB)_8$ | RBRBRBRBRBRBRBRB-B | 14 |
| $(rB)_8$ | rBrBrBrBrBrBrBrB-B | 15 |
| $(RB)_7$ | RBRBRBRBRBRBRB-B | 16 |
| $(RB)_5$ | RBRBRBRBRB-B | 17 |
| $(RB)_3$ | RBRBRB-B | 18 |
| B(3b); CP06062; $(RXRRBR)_2XB$ | RXRRBRRXRRBR-XB | 19 |
| D(2); $(RB)_5RXRBRX-B$ | RBRBRBRBRBRXBRX-B | 20 |
| E(3c); $(RBRBRBRX)_2X$ | RBRBRBRXRBRBRBRX-X | 21 |
| F(3a); X-$RB)_3RX(RB)_3RX$ | X-RBRBRBRXRBRBRBRX | 22 |
| G(4b); $(RBRX)_4B$ | RBRXRBRXRBRXRBRX-B | 23 |
| H(4a); $(RB)_4(RX)_4B$ | RBRBRBRBRXRXRXRX-B | 24 |
| I(3d); $RX(RB)_2RX(RB)_3RX-X$ | RXRBRBRXRBRBRBRX-X | 25 |
| C(4c); $(RXR)_3RBR-XB$ | RXRRXRRXRRBR-XB | 26 |
| $(RB)_7RX-B$ | RBRBRBRBRBRBRBRX-B | 27 |
| Oligonucleotide sequences | | |
| H53A(+39 +69) | CATTCAACTGTTGCCTCCGGTTCTGAAGGTG | 28 |
| H53A(+39 +62) | CTGTTGCCTCCGGTTCTGAAGGTG | 29 |
| H53A(+45 +69) | CATTCAACTGTTGCCTCCGGTTCTG | 30 |
| H44A(+85 +104) | TTTGTGTCTTTCTGAGAAAC | 31 |
| H44A(-06 +14) | ATCTGTCAAATCGCCTGCAG | 32 |
| H44D(+10 -10) | AAAGACTTACCTTAAGATAC | 33 |
| AVI-4657 (hu-exon51) | CTT ACA GGC TCC AAT AGT GGT CAG T | 34 |
| Hu.DMD.Exon51.010 | ATT TCT AGT TTG GAG ATG GCA GTT TC | 35 |
| Hu.DMD.Exon51.012 | GAG CAG GTA CCT CCA ACA TCA AGG AA | 36 |
| M23d PMO | GGCCAAACCTCGGCTTACCTGAAAT | 37 |
| AVI-4658 (hu-exon 51) | CTCCAACATCAAGGAAGATGGCATTTCTAG | 38 |
| Human Myostatin SD1 | ACTCTGTAGGCATGGTAATG | 39 |
| Human Myostatin SD2 | CAGCCCATCTTCTCCTGG | 40 |
| Human Myostatin SA2 | CACTTGCATTAGAAAATCAG | 41 |
| Human Myostatin SA3 | CTTGACCTCTAAAAACGGATT | 42 |
| Human Myostatin-AUG | GAGTTGCAGTTTTTGCATG | 43 |
| CAG25 | AGCAGCAGCAGCAGCAGCAGCA | 44 |
| CAG22 | AGCAGCAGCAGCAGCAGCA | 45 |
| CAG19 | AGCAGCAGCAGCAGCA | 46 |
| CAG12 | AGCAGCAGCAGC | 47 |
| CCAG24 | AGCCAGCCAGCCAGCCAGCCAGCC | 48 |
| CUG39 | CUGCUGCUGCUGCUGCUGCUGCUGCUGCUGCUGCUGCUG | 49 |
| CCUG40 | CCUGCCUGCCUGCCUGCCUGCCUGCCUGCCUGCCUG | 50 |

Sequence Table

| Homing peptides | Peptide Sequence (NH₂ to COOH) | SEQ ID NO. |
| --- | --- | --- |
| Skeletal Muscle-SMP1 | ASSLNIA | 51 |
| SMP2 | SLGSFP | 52 |
| SMP3 | SGASAV | 53 |
| SMP4 | GRSGAR | 54 |
| SMP5 | TARGEHKEEELI | 55 |
| Cardiac Muscle-CMP1 | WLSEAGPVVTVRALRGTGSW | 56 |
| CMP2 | VTVRALRGTSW | 57 |
| CMP3 | VVTVRALRGTGSW | 58 |
| CMP4 | CRPPR | 59 |
| CMP5 | SKTFNTHPQSTP | 60 |

Conjugate compounds

| | | |
| --- | --- | --- |
| (RXRRBR)₂XB-4658 | RXRRBRRXRRBR-XB-GGCCAAACCTCGGCTTACCTGAAAT | 61 |
| (RXRRBR)₂XB-M23d PMO | RXRRBRRXRRBR-XB-GGCCAAACCTCGGCTTACCTGAAAT | 62 |
| (RXRR(B/X)R)₂X-B-myo | RXRRBRRXRRBR-B-GGCCAAACCTCGGCTTACCTGAAAT | 63 |
| (RXRR(B/X)R)₂X Bmyo | RXRRBRRXRRBR-XB-GGCCAAACCTCGGCTTACCTGAAAT | 64 |
| (RXRR(B/X)R)₂X B CAG25 | RXRRBRRXRRBR-XB-AGCAGCAGCAGCAGCAGCAGCA | 65 |
| (RXRR(B/X)R)₂X B CCAG24 | RXRRBRRXRRBR-XB-AGCCAGCCAGCCAGCCAGCCAGCC | 66 |

$^a$In SEQ ID Nos. 3-27, sequences assigned to SEQ ID NO. do not include the linkage portion (X, B, or XB).

It is claimed:

1. A peptide-antisense conjugate comprising a cell-penetrating peptide (CPP) covalently linked to a morpholino antisense oligomer, wherein:
   the morpholino antisense oligomer comprises 12 to 30 morpholino subunits linked by phosphorus-containing linkages, wherein each morpholino ring supports a base pairing moiety, and wherein at least 12 contiguous base pairing moieties are complementary to a target muscle protein mRNA;
   the target muscle protein is selected from the group consisting of dystrophin and dystrophia myotonica protein kinase;
   the CPP is of the formula (RXRRBR)$_2$ (SEQ ID NO: 71) wherein R is arginine, X is 6-aminohexanoic acid, and B is 3-aminopropionic acid; and
   the CPP is covalently linked to the 3' or 5' terminal morpholino subunit of the morpholino antisense oligomer at the CPP carboxy terminus by an XB linker.

2. The peptide-antisense conjugate of claim 1, wherein the CPP is linked to the 3' terminal morpholino subunit.

3. The peptide-antisense conjugate of claim 1, wherein the CPP and linker taken together are of the formula:

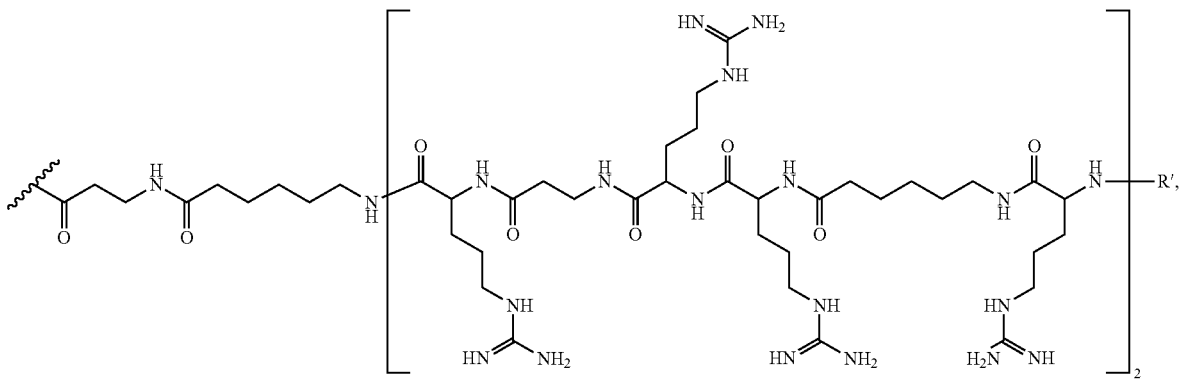

wherein R' is selected from H and acetyl.

4. The peptide-antisense conjugate of claim 3, wherein the CPP is conjugated to the 5' terminal morpholino subunit of the morpholino antisense oligomer, wherein the 5' terminal morpholino subunit, CPP, and linker taken together are of the formula:

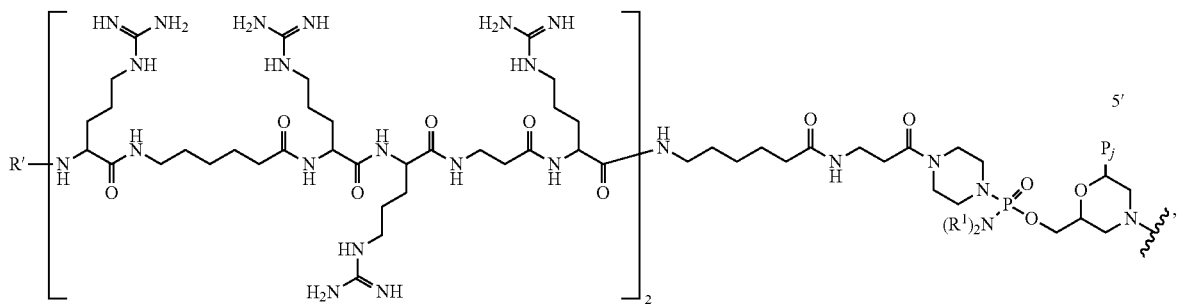

wherein:
   $R^1$ is $C_1$-$C_6$ alkyl, and
   $P_j$ is a purine or pyrimidine base-pairing moiety.

5. The peptide-antisense conjugate of claim 4, wherein $R^1$ is selected from methyl, ethyl, isopropyl, n-butyl, isobutyl, and t-butyl.

6. The peptide-antisense conjugate of claim 4, wherein $R^1$ is methyl.

7. The peptide-antisense conjugate of claim 4, wherein $P_j$ is selected from adenine, cytosine, guanine, uracil, thymine, inosine, hypoxanthine, and 5-methyl cytosine.

8. A peptide-antisense conjugate of formula:

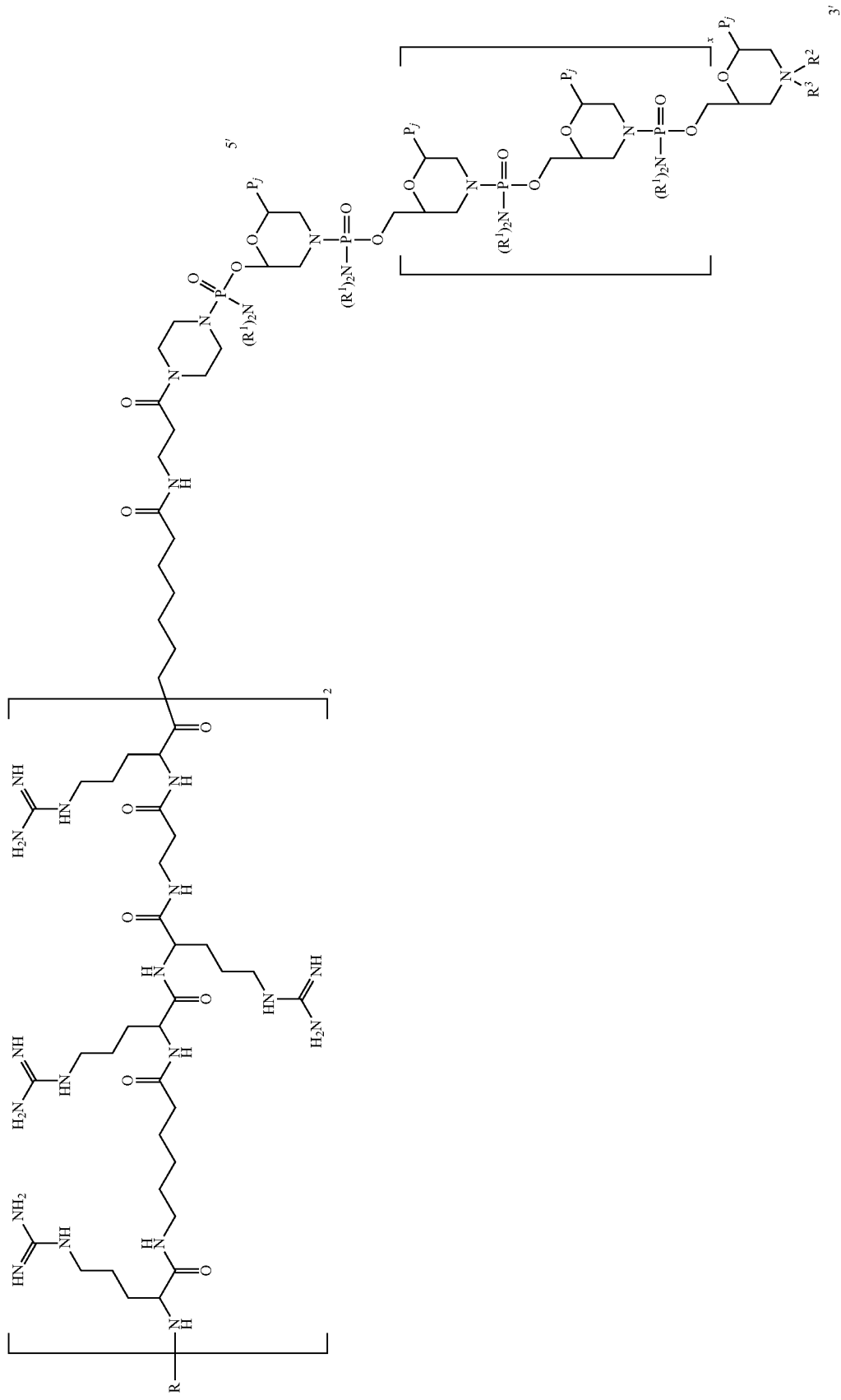

or a pharmaceutically acceptable salt thereof, wherein:
R is selected from H and acetyl;
each $R^1$ is independently a $C_1$-$C_6$ alkyl;
X is an integer from 3 to 19;
each $P_j$ is independently a purine or pyrimidine base-pairing moiety, wherein, taken together, the $P_j$'s comprise a targeting sequence;
$R^2$ is selected from H and acetyl;
$R^3$ is selected from an electron pair and H;
the targeting sequence is complementary to a target skeletal muscle protein mRNA and/or a target cardiac muscle protein mRNA; and
the target muscle protein is selected from the group consisting of dystrophin and dystrophia myotonica protein kinase.

9. The peptide-antisense conjugate of claim 8, wherein each $R^1$ is independently selected from methyl, ethyl, isopropyl, n-butyl, isobutyl, and t-butyl.

10. The peptide-antisense conjugate of claim 8, wherein each $R^1$ is methyl.

11. The peptide-antisense conjugate of claim 8, wherein each $P_j$ is independently selected from adenine, cytosine, guanine, uracil, thymine, inosine, hypoxanthine, and 5-methyl cytosine.

* * * * *

SEQUENCE LISTING

```
<160> NUMBER OF SEQ ID NOS: 72

<210> SEQ ID NO 1
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 1
cctcttacct cagttaca                                                18

<210> SEQ ID NO 2
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 2
gctattacct taacccag                                                18

<210> SEQ ID NO 3
<211> LENGTH: 10
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = beta-alanine

<400> SEQUENCE: 3

Arg Arg Arg Arg Arg Arg Arg Arg Xaa Xaa
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (1)...(8)
<223> OTHER INFORMATION: Xaa = D-arginine
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = beta-alanine

<400> SEQUENCE: 4

Xaa Xaa Xaa Xaa Xaa Xaa Xaa Xaa Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = beta-alanine

<400> SEQUENCE: 5

Arg Arg Arg Arg Arg Arg Arg Arg Arg Xaa Xaa
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(16)
<223> OTHER INFORMATION: Xaa = 6-aminohexanoic acid
<220> FEATURE:
<221> NAME/KEY: MOD_RES
<222> LOCATION: (17)...(17)
<223> OTHER INFORMATION: Xaa = beta-alanine

<400> SEQUENCE: 6

Arg Xaa Arg Xaa Arg Xaa Arg Xaa Arg Xaa Arg Xaa Arg Xaa Arg Xaa Xaa
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (1), (3), (5), (7), (9), (11), (13), (15)
<223> OTHER INFORMATION: Xaa = D-arginine
<220> FEATURE:
```

```
<221> NAME/KEY: MOD_RES
<222> LOCATION: (2), (4), (6), (8), (10), (12), (14), (16)
<223> OTHER INFORMATION: Xaa = 6-aminohexanoic acid
<220> FEATURE:
<221> NAME/KEY: MOD_RES
<222> LOCATION: (17)...(17)
<223> OTHER INFORMATION: Xaa = beta-alanine

<400> SEQUENCE: 7

Xaa Xaa Xaa Xaa Xaa Xaa Xaa Xaa Xaa Xaa Xaa Xaa Xaa Xaa Xaa Xaa Xaa
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(14)
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = beta-alanine

<400> SEQUENCE: 8

Arg Xaa Arg Xaa Arg Xaa Arg Xaa Arg Xaa Arg Xaa Arg Xaa Xaa
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(10)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = beta-alanine

<400> SEQUENCE: 9

Arg Xaa Arg Xaa Arg Xaa Arg Xaa Arg Xaa Xaa
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(6)
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = beta-alanine

<400> SEQUENCE: 10

Arg Xaa Arg Xaa Arg Xaa Xaa
1               5

<210> SEQ ID NO 11
<211> LENGTH: 14
```

-continued

```
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(13)
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = beta-alanine

<400> SEQUENCE: 11

Arg Xaa Arg Arg Xaa Arg Arg Xaa Arg Arg Xaa Arg Xaa Xaa
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (1), (4), (7), (10)
<223> OTHER INFORMATION: Xaa = D-arginine
<220> FEATURE:
<221> NAME/KEY: MOD_RES
<222> LOCATION: (2), (5), (8), (11)
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = beta-alanine

<400> SEQUENCE: 12

Xaa Xaa Arg Xaa Xaa Arg Xaa Xaa Arg Xaa Xaa Arg Xaa
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (1), (3), (4), (6), (7), (9), (10), (12)
<223> OTHER INFORMATION: Xaa = D-arginine
<220> FEATURE:
<221> NAME/KEY: MOD_RES
<222> LOCATION: (2), (5), (8), (11), (13)
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = beta-alanine

<400> SEQUENCE: 13

Xaa Xaa Xaa Xaa Xaa Xaa Xaa Xaa Xaa Xaa Xaa Xaa Xaa Xaa
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(17)
<223> OTHER INFORMATION: Xaa = beta-alanine
```

<400> SEQUENCE: 14

Arg Xaa Arg Xaa Arg Xaa Arg Xaa Arg Xaa Arg Xaa Arg Xaa Arg Xaa Xaa
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (1), (3), (5), (7), (9), (11), (13), (15)
<223> OTHER INFORMATION: Xaa = D-arginine
<220> FEATURE:
<221> NAME/KEY: MOD_RES
<222> LOCATION: (2), (4), (6), (8), (10), (12), (14), (16), (17)
<223> OTHER INFORMATION: Xaa = beta-alanine

<400> SEQUENCE: 15

Xaa Xaa Xaa Xaa Xaa Xaa Xaa Xaa Xaa Xaa Xaa Xaa Xaa Xaa Xaa Xaa Xaa
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(15)
<223> OTHER INFORMATION: Xaa = beta-alanine

<400> SEQUENCE: 16

Arg Xaa Arg Xaa Arg Xaa Arg Xaa Arg Xaa Arg Xaa Arg Xaa Xaa
1               5                   10                  15

<210> SEQ ID NO 17
<211> LENGTH: 11
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(11)
<223> OTHER INFORMATION: Xaa = beta-alanine

<400> SEQUENCE: 17

Arg Xaa Arg Xaa Arg Xaa Arg Xaa Arg Xaa Xaa
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2)...(7)
<223> OTHER INFORMATION: Xaa = beta-alanine

<400> SEQUENCE: 18

Arg Xaa Arg Xaa Arg Xaa Xaa
1               5

```
<210> SEQ ID NO 19
<211> LENGTH: 14
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (8), (13)
<223> OTHER INFORMATION: Xaa = 6-aminohexanoic acid
<220> FEATURE:
<221> NAME/KEY: MOD_RES
<222> LOCATION: (5), (11), (14)
<223> OTHER INFORMATION: Xaa = beta-alanine

<400> SEQUENCE: 19

Arg Xaa Arg Arg Xaa Arg Arg Xaa Arg Arg Xaa Arg Xaa Xaa
 1               5                  10

<210> SEQ ID NO 20
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (4), (6), (8), (10), (14), (17)
<223> OTHER INFORMATION: Xaa = beta-alanine
<220> FEATURE:
<221> NAME/KEY: MOD_RES
<222> LOCATION: (12), (16)
<223> OTHER INFORMATION: Xaa = 6-aminohexanoic acid

<400> SEQUENCE: 20

Arg Xaa Arg Xaa Arg Xaa Arg Xaa Arg Xaa Arg Xaa Arg Xaa Arg Xaa Xaa
 1               5                  10                  15

<210> SEQ ID NO 21
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (4), (6), (10), (12), (14)
<223> OTHER INFORMATION: Xaa = beta-alanine
<220> FEATURE:
<221> NAME/KEY: MOD_RES
<222> LOCATION: (8), (16), (17)
<223> OTHER INFORMATION: Xaa = 6-aminohexanoic acid

<400> SEQUENCE: 21

Arg Xaa Arg Xaa Arg Xaa Arg Xaa Arg Xaa Arg Xaa Arg Xaa Arg Xaa Xaa
 1               5                  10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (1), (9), (17)
<223> OTHER INFORMATION: Xaa = 6-aminohexanoic acid
<220> FEATURE:
<221> NAME/KEY: MOD_RES
<222> LOCATION: (3), (5), (7), (11), (13), (15)
<223> OTHER INFORMATION: Xaa = beta-alanine

<400> SEQUENCE: 22
```

```
Xaa Arg Xaa Arg Xaa Arg Xaa Arg Xaa Arg Xaa Arg Xaa Arg Xaa
1               5                   10                  15
```

<210> SEQ ID NO 23
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (6), (10), (14), (17)
<223> OTHER INFORMATION: Xaa = beta-alanine
<220> FEATURE:
<221> NAME/KEY: MOD_RES
<222> LOCATION: (4), (8), (12), (16)
<223> OTHER INFORMATION: Xaa = 6-aminohexanoic acid

<400> SEQUENCE: 23

```
Arg Xaa Arg Xaa Arg Xaa Arg Xaa Arg Xaa Arg Xaa Arg Xaa Arg Xaa Xaa
1               5                   10                  15
```

<210> SEQ ID NO 24
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (4), (6), (8), (17)
<223> OTHER INFORMATION: Xaa = beta-alanine
<220> FEATURE:
<221> NAME/KEY: MOD_RES
<222> LOCATION: (10), (12), (14), (16)
<223> OTHER INFORMATION: Xaa = 6-aminohexanoic acid

<400> SEQUENCE: 24

```
Arg Xaa Arg Xaa Arg Xaa Arg Xaa Arg Xaa Arg Xaa Arg Xaa Arg Xaa Xaa
1               5                   10                  15
```

<210> SEQ ID NO 25
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (8), (16), (17)
<223> OTHER INFORMATION: Xaa = 6-aminohexanoic acid
<220> FEATURE:
<221> NAME/KEY: MOD_RES
<222> LOCATION: (4), (6), (10), (12), (14)
<223> OTHER INFORMATION: Xaa = beta-alanine

<400> SEQUENCE: 25

```
Arg Xaa Arg Xaa Arg Xaa Arg Xaa Arg Xaa Arg Xaa Arg Xaa Arg Xaa Xaa
1               5                   10                  15
```

<210> SEQ ID NO 26
<211> LENGTH: 14
<212> TYPE: PRT
<213> ORGANISM: Artificial Sequence
<220> FEATURE:
<223> OTHER INFORMATION: Synthetic cell penetrating peptide
      220>
<221> NAME/KEY: MOD_RES
<222> LOCATION: (2), (5), (8), (13)
<223> OTHER INFORMATION: Xaa = 6-aminohexanoic acid
<220> FEATURE:

```
<221> NAME/KEY: MOD_RES
<222> LOCATION: (11), (14)
<223> OTHER INFORMATION: Xaa = beta-alanine

<400> SEQUENCE: 26

Arg Xaa Arg Arg Xaa Arg Arg Xaa Arg Arg Xaa Arg Xaa Xaa
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (4), (6), (8), (10), (12), (14), (17)
<223> OTHER INFORMATION: Xaa = beta-alanine
<220> FEATURE:
<221> NAME/KEY: MOD_RES
<222> LOCATION: (16)
<223> OTHER INFORMATION: Xaa = 6-aminohexanoic acid

<400> SEQUENCE: 27

Arg Xaa Arg Xaa Arg Xaa Arg Xaa Arg Xaa Arg Xaa Arg Xaa Arg Xaa Xaa
1               5                   10                  15

<210> SEQ ID NO 28
<211> LENGTH: 31
<212> TYPE: DNA
<213> ORGANISM: Artificial Sequence
<220> FEATURE:
<223> OTHER INFORMATION: Synthetic antisense oligomer

<400> SEQUENCE: 28
cattcaactg ttgcctccgg ttctgaaggt g                              31

<210> SEQ ID NO 29
<211> LENGTH: 24
<212> TYPE: DNA
<213> ORGANISM: Artificial Sequence
<220> FEATURE:
<223> OTHER INFORMATION: Synthetic antisense oligomer

<400> SEQUENCE: 29
ctgttgcctc cggttctgaa ggtg                                      24

<210> SEQ ID NO 30
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 30
cattcaactg ttgcctccgg ttctg                                     25

<210> SEQ ID NO 31
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 31
tttgtgtctt tctgagaaac                                           20
```

```
<210> SEQ ID NO 32
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 32
atctgtcaaa tcgcctgcag                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 33
aaagacttac cttaagatac                                                   20

<210> SEQ ID NO 34
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 34
cttacaggct ccaatagtgg tcagt                                             25

<210> SEQ ID NO 35
<211> LENGTH: 26
<212> TYPE: DNA
<213> ORGANISM: Artificial Sequence
<220> FEATURE:
<223> OTHER INFORMATION: Synthetic antisense oligomer

<400> SEQUENCE: 35
atttctagtt tggagatggc agtttc                                            26

<210> SEQ ID NO 36
<211> LENGTH: 26
<212> TYPE: DNA
<213> ORGANISM: Artificial Sequence
<220> FEATURE:
<223> OTHER INFORMATION: Synthetic antisense oligomer

<400> SEQUENCE: 36
gagcaggtac ctccaacatc aaggaa                                            26

<210> SEQ ID NO 37
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 37
ggccaaacct cggcttacct gaaat                                             25

<210> SEQ ID NO 38
<211> LENGTH: 30
<212> TYPE: DNA
<213> ORGANISM: Artificial Sequence
<220> FEATURE:
<223> OTHER INFORMATION: Synthetic antisense oligomer
```

```
<400> SEQUENCE: 38
ctccaacatc aaggaagatg gcatttctag                                    30

<210> SEQ ID NO 39
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 39
actctgtagg catggtaatg                                               20

<210> SEQ ID NO 40
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 40
cagcccatct tctcctgg                                                 18

<210> SEQ ID NO 41
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 41
cacttgcatt agaaaatcag                                               20

<210> SEQ ID NO 42
<211> LENGTH: 21
<212> TYPE: DNA
<213> ORGANISM: Artificial Sequence
<220> FEATURE:
<223> OTHER INFORMATION: Synthetic antisense oligomer

<400> SEQUENCE: 42
cttgacctct aaaaacggat t                                             21

<210> SEQ ID NO 43
<211> LENGTH: 19
<212> TYPE: DNA
<213> ORGANISM: Artificial Sequence
<220> FEATURE:
<223> OTHER INFORMATION: Synthetic antisense oligomer

<400> SEQUENCE: 43
gagttgcagt ttttgcatg                                                19

<210> SEQ ID NO 44
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 44
agcagcagca gcagcagcag cagca                                         25

<210> SEQ ID NO 45
<211> LENGTH: 22
```

```
<212> TYPE: DNA
<213> ORGANISM: Artificial Sequence
<220> FEATURE:
<223> OTHER INFORMATION: Synthetic antisense oligomer

<400> SEQUENCE: 45
agcagcagca gcagcagcag ca                                              22

<210> SEQ ID NO 46
<211> LENGTH: 19
<212> TYPE: DNA
<213> ORGANISM: Artificial Sequence
<220> FEATURE:
<223> OTHER INFORMATION: Synthetic antisense oligomer

<400> SEQUENCE: 46
agcagcagca gcagcagca                                                  19

<210> SEQ ID NO 47
<211> LENGTH: 12
<212> TYPE: DNA
<213> ORGANISM: Artificial Sequence
<220> FEATURE:
<223> OTHER INFORMATION: Synthetic antisense oligomer

<400> SEQUENCE: 47
agcagcagca gc                                                         12

<210> SEQ ID NO 48
<211> LENGTH: 24
<212> TYPE: DNA
<213> ORGANISM: Artificial Sequence
<220> FEATURE:
<223> OTHER INFORMATION: Synthetic antisense oligomer

<400> SEQUENCE: 48
agccagccag ccagccagcc agcc                                            24

<210> SEQ ID NO 49
<211> LENGTH: 39
<212> TYPE: DNA
<213> ORGANISM: Artificial Sequence
<220> FEATURE:
<223> OTHER INFORMATION: Synthetic antisense oligomer

<400> SEQUENCE: 49
cugcugcugc ugcugcugcu gcugcugcug cugcugcug                            39

<210> SEQ ID NO 50
<211> LENGTH: 40
<212> TYPE: DNA
<213> ORGANISM: Artificial Sequence
<220> FEATURE:
<223> OTHER INFORMATION: Synthetic antisense oligomer

<400> SEQUENCE: 50
ccugccugcc ugccugccug ccugccugcc ugccugccug                           40

<210> SEQ ID NO 51
<211> LENGTH: 7
<212> TYPE: PRT
<213> ORGANISM: Artificial Sequence
<220> FEATURE:
<223> OTHER INFORMATION: Synthetic homing peptides

<400> SEQUENCE: 51
```

```
Ala Ser Ser Leu Asn Ile Ala
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic homing peptide

<400> SEQUENCE: 52

Ser Leu Gly Ser Phe Pro
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic homing peptide

<400> SEQUENCE: 53

Ser Gly Ala Ser Ala Val
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic homing peptides

<400> SEQUENCE: 54

Gly Arg Ser Gly Ala Arg
1               5

<210> SEQ ID NO 55
<211> LENGTH: 12
<212> TYPE: PRT
<213> ORGANISM: Artificial Sequence
<220> FEATURE:
<223> OTHER INFORMATION: Synthetic homing peptide

<400> SEQUENCE: 55

Thr Ala Arg Gly Glu His Lys Glu Glu Glu Leu Ile
1               5                   10

<210> SEQ ID NO 56
<211> LENGTH: 20
<212> TYPE: PRT
<213> ORGANISM: Artificial Sequence
<220> FEATURE:
<223> OTHER INFORMATION: Synthetic homing peptide

<400> SEQUENCE: 56

Trp Leu Ser Glu Ala Gly Pro Val Val Thr Val Arg Ala Leu Arg Gly
1               5                   10                  15

Thr Gly Ser Trp
            20

<210> SEQ ID NO 57
<211> LENGTH: 11
<212> TYPE: PRT
<213> ORGANISM: Artificial Sequence
<220> FEATURE:
<223> OTHER INFORMATION: Synthetic homing peptide
```

```
<400> SEQUENCE: 57

Val Thr Val Arg Ala Leu Arg Gly Thr Ser Trp
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic homing peptide

<400> SEQUENCE: 58

Val Val Thr Val Arg Ala Leu Arg Gly Thr Gly Ser Trp
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Synthetic homing peptide

<400> SEQUENCE: 59

Cys Arg Pro Pro Arg
1               5

<210> SEQ ID NO 60
<211> LENGTH: 12
<212> TYPE: PRT
<213> ORGANISM: Artificial Sequence
<220> FEATURE:
<223> OTHER INFORMATION: Synthetic homing peptide

<400> SEQUENCE: 60

Ser Lys Thr Phe Asn Thr His Pro Gln Ser Thr Pro
1               5                   10

<210> SEQ ID NO 61
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 61
ggccaaacct cggcttacct gaaat                                             25

<210> SEQ ID NO 62
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 62
ggccaaacct cggcttacct gaaat                                             25

<210> SEQ ID NO 63
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 63
ggccaaacct cggcttacct gaaat                                             25
```

<210> SEQ ID NO 64
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 64
ggccaaacct cggcttacct gaaat                                          25

<210> SEQ ID NO 65
<211> LENGTH: 25
<212> TYPE: DNA
<213> ORGANISM: Artificial Sequence
<220> FEATURE:
<223> OTHER INFORMATION: Synthetic antisense oligomer

<400> SEQUENCE: 65
agcagcagca gcagcagcag cagca                                          25

<210> SEQ ID NO 66
<211> LENGTH: 24
<212> TYPE: DNA
<213> ORGANISM: Artificial Sequence
<220> FEATURE:
<223> OTHER INFORMATION: Synthetic antisense oligomer

<400> SEQUENCE: 66
agccagccag ccagccagcc agcc                                           24

<210> SEQ ID NO 67
<211> LENGTH: 14
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (8), (13)
<223> OTHER INFORMATION: Xaa = 6-aminohexanoic acid, 5-aminopentanoic
      acid or 4-aminobutanoic acid
<220> FEATURE:
<221> NAME/KEY: MOD_RES
<222> LOCATION: (5), (11), (14)
<223> OTHER INFORMATION: Xaa = beta-alanine

<400> SEQUENCE: 67

Arg Xaa Arg Arg Xaa Arg Arg Xaa Arg Arg Xaa Arg Xaa Xaa
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (8), (13)
<223> OTHER INFORMATION: Xaa = 6-aminohexanoic acid, 5-aminopentanoic
      acid or 4-aminobutanoic acid
<220> FEATURE:
<221> NAME/KEY: MOD_RES
<222> LOCATION: (5), (11)
<223> OTHER INFORMATION: Xaa = beta-alanine, 6-aminohexanoic acid,
      5-aminopentanoic acid or 4-aminobutanoic acid
<220> FEATURE:
<221> NAME/KEY: MOD_RES
<222> LOCATION: (14)

```
<223> OTHER INFORMATION: Xaa = beta-alanine

<400> SEQUENCE: 68

Arg Xaa Arg Arg Xaa Arg Arg Xaa Arg Arg Xaa Arg Xaa Xaa
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (4), (6), (8), (10), (12), (14), (16)
<223> OTHER INFORMATION: Xaa = 6-aminohexanoic acid

<400> SEQUENCE: 69

Arg Xaa Arg Xaa Arg Xaa Arg Xaa Arg Xaa Arg Xaa Arg Xaa Arg Xaa
1               5                   10                  15

<210> SEQ ID NO 70
<211> LENGTH: 12
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (5), (8), (11)
<223> OTHER INFORMATION: Xaa = 6-aminohexanoic acid

<400> SEQUENCE: 70

Arg Xaa Arg Arg Xaa Arg Arg Xaa Arg Arg Xaa Arg
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: MOD_RES
<222> LOCATION: (2), (8)
<223> OTHER INFORMATION: Xaa = 6-aminohexanoic acid
<220> FEATURE:
<221> NAME/KEY: MOD_RES
<222> LOCATION: (5), (11)
<223> OTHER INFORMATION: Xaa = beta-alanine

<400> SEQUENCE: 71

Arg Xaa Arg Arg Xaa Arg Arg Xaa Arg Arg Xaa Arg
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Synthetic cell penetrating peptide

<400> SEQUENCE: 72

Cys Arg Val Ala Ser Val Leu Pro Cys
1               5
```